US011707737B2

(12) United States Patent
Gray

(10) Patent No.: US 11,707,737 B2
(45) Date of Patent: Jul. 25, 2023

(54) QUANT PRODUCTION AND DOSING

(71) Applicant: Mark A. Gray, Avalon, CA (US)

(72) Inventor: Mark A. Gray, Avalon, CA (US)

(*) Notice: Subject to any disclaimer, the term of this patent is extended or adjusted under 35 U.S.C. 154(b) by 520 days.

(21) Appl. No.: 16/865,062

(22) Filed: May 1, 2020

(65) Prior Publication Data

US 2020/0254453 A1    Aug. 13, 2020

Related U.S. Application Data

(63) Continuation of application No. PCT/US2018/058938, filed on Nov. 2, 2018.
(Continued)

(51) Int. Cl.
*B01L 3/00* (2006.01)

(52) U.S. Cl.
CPC . *B01L 3/502715* (2013.01); *B01L 2200/0652* (2013.01); *B01L 2300/0867* (2013.01); *B01L 2300/14* (2013.01)

(58) Field of Classification Search
CPC ......... B01L 3/502784; B01L 2200/027; B01L 2200/0636; B01L 2200/0652;
(Continued)

(56) References Cited

U.S. PATENT DOCUMENTS

| 6,190,870 B1 | 2/2001 | Schmitz et al. |
| 9,757,726 B2 | 9/2017 | Sharpe et al. |

(Continued)

FOREIGN PATENT DOCUMENTS

| JP | 2009061382 A | 3/2009 |
| WO | 2016149625 A1 | 9/2016 |
| WO | WO-2019090062 A1 | 5/2019 |

OTHER PUBLICATIONS

International Preliminary Report on Patentability for PCT/US2018/058938 dated May 5, 2020.
(Continued)

*Primary Examiner* — Sharon Pregler
(74) *Attorney, Agent, or Firm* — Acuity IP, LLC; Nathan S. Cassell

(57) ABSTRACT

Engineered nanoscale multicomponent particles are introduced and are called "quants." Methods and apparatuses for producing such multicomponent nanoparticles are provided. A single quant can be manufactured to contain a variety of different internal component molecules. Likewise, a plurality of such quants may be manufactured wherein the plurality of quants are suspended in an aqueous solution. Typically, quants are produced in quantity and concentration adequate to support human scale therapeutics. In some embodiments, millions or billions of quants are suspended in a volume of aqueous solution for delivery to a patient. When manufactured to the same specification, the plurality of quants are uniform in size, uniform in chemical composition, and therefore uniform in functionality. Functional uniformity is an essential aspect of quants, manifested in design and production. By controlling the variables of manufacture, such as particle size and composition, and by redefining a drug dose as the measured number of quants delivered (as opposed to measuring a drug dose by the mass of its active ingredient), the performance of these nanoparticle-based drugs introduce significant efficiencies and much higher value products to the expanding therapeutics market.

20 Claims, 29 Drawing Sheets

Related U.S. Application Data

(60) Provisional application No. 62/581,548, filed on Nov. 3, 2017.

(58) Field of Classification Search
CPC ....... B01L 2200/143; B01L 2300/0645; B01L 2300/0864; B01L 2300/0867; B01L 2300/14; B01L 2400/0487; B01L 3/0293; G01N 15/1459; G01N 15/1031; G01N 15/1463; G01N 1/44; G01N 21/66; G01N 21/714; G01N 21/73; G01N 27/622; G01N 33/54326; G01N 33/574; G01N 35/08; G01N 35/085
See application file for complete search history.

(56) References Cited

U.S. PATENT DOCUMENTS

| | | |
|---|---|---|
| 2006/0181557 A1 | 8/2006 | Hoisington et al. |
| 2007/0035597 A1 | 2/2007 | Ready et al. |
| 2007/0215528 A1 | 9/2007 | Hayenga et al. |
| 2008/0171077 A1* | 7/2008 | Gray .................. A61K 31/7105 264/4.1 |
| 2010/0203142 A1 | 8/2010 | Zhang et al. |
| 2011/0129941 A1* | 6/2011 | Kumacheva ........ B01F 25/4331 436/180 |
| 2014/0220350 A1 | 8/2014 | Kim et al. |
| 2016/0037802 A1 | 2/2016 | Willcocks et al. |
| 2016/0172178 A1 | 6/2016 | Apffel et al. |

OTHER PUBLICATIONS

Loscertales, I.G., et al., "Micro/Nano Encapsulation via Electrified Coaxial Liquid Jets," Science, vol. 295, pp. 1695-1698 (2002).
Supplementary European Search Report from EP Application No. 18872079 dated Nov. 12, 2021, 2 pages.

* cited by examiner

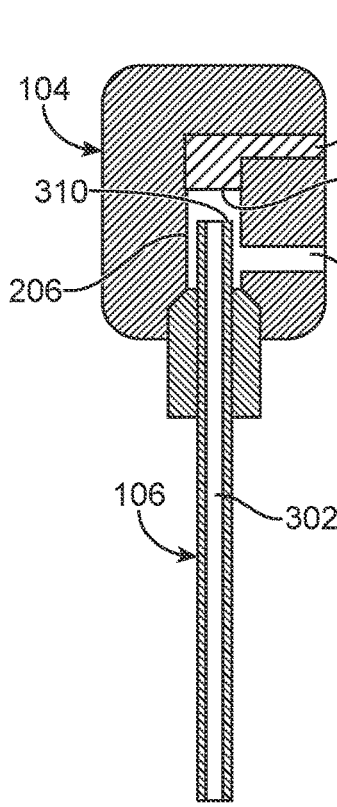
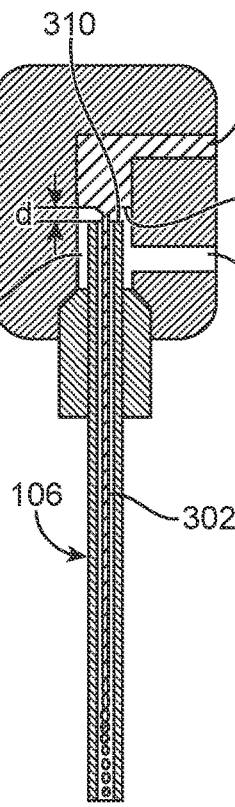
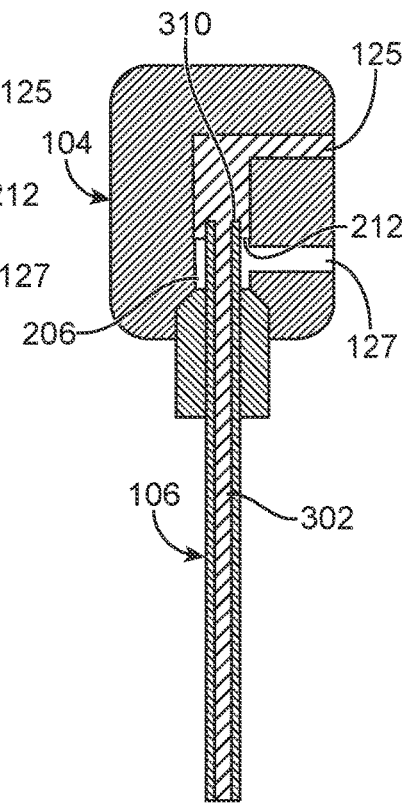
FIG. 18A  FIG. 18B  FIG. 18C
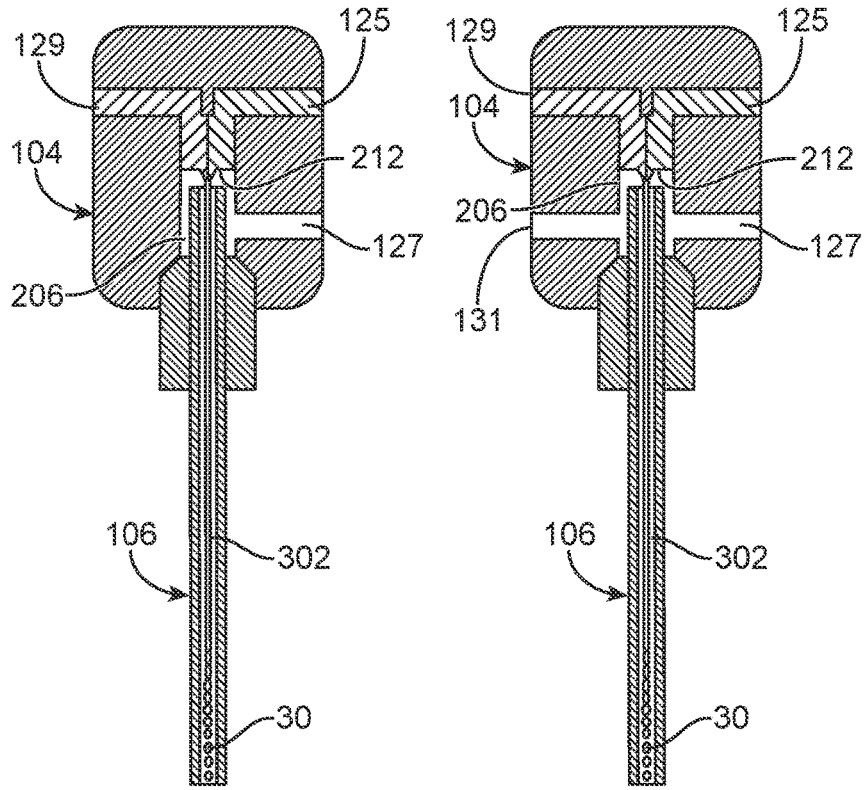
FIG. 19  FIG. 20

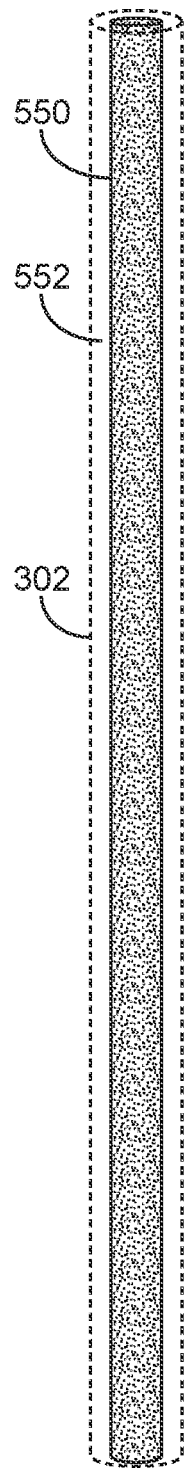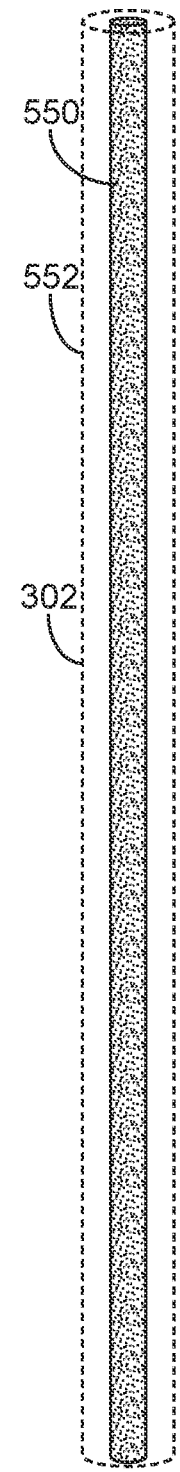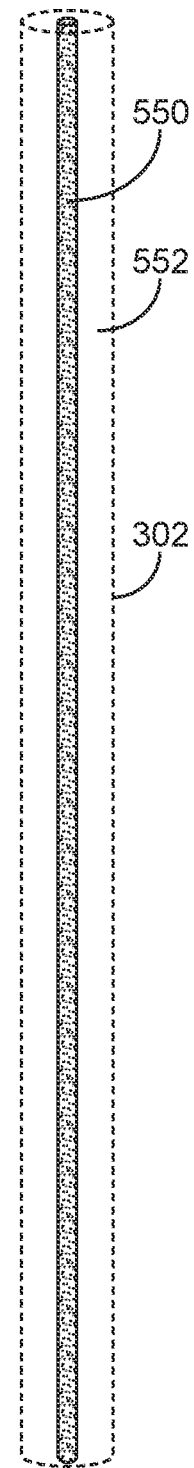
FIG. 29D  FIG. 29E  FE. 29F

QUANT PRODUCTION AND DOSING

CROSS-REFERENCE

This application is a continuation of PCT Application No. PCT/US2018/058938, filed Nov. 2, 2018, which claims the benefit of U.S. Provisional Application No. 62/581,548 filed on Nov. 3, 2017, the entire disclosure of which is incorporated herein by reference for all purposes.

BACKGROUND OF THE INVENTION

Drug therapy, also called pharmacotherapy, is a general term for using medication to treat disease. In general, drugs are molecules that interact with and alter cellular function to promote healthy functioning or reduce illness. The method of delivering drugs to their site of action varies depending on the patient and condition being treated. For example, medications may be taken orally in pill, capsule or liquid form, or may be injected into specific tissues, muscles or blood stream. Many medications are delivered via continuous or intermittent intravenous (IV) infusion, particularly for the treatment of cancer. This involves adding the medication to sterile IV solution and then delivering the IV solution as a primary infusion. The infusion of parenteral drug can occur over several hours or days.

One key determinant of the effectivity of a drug is its solubility in water or blood. Drugs must be present in the form of an aqueous solution at the site of absorption. When considered in the traditional paradigm of pharmacokinetics, solubility determines the concentration of drug in systemic circulation required for a desired pharmacological response. However, many therapeutic molecules are either weakly acidic or weakly basic, having poor aqueous solubility. Poorly soluble drugs often require high doses in order to reach therapeutic plasma concentrations. Low aqueous solubility is a major problem encountered with formulation development of new chemical entities as well as generic development. More than 40% of new chemical entities (NCEs) developed by the pharmaceutical industry are practically insoluble in water. Solubility is thus a major challenge for the formulation scientist.

IUPAC defines solubility as the analytical composition of a saturated solution expressed as a proportion of a designated solute in a designated solvent. Solubility may be stated in units of concentration, molality, mole fraction, mole ratio, and other units. Table 1 provides a framework of the solubility criteria as set out by United States Pharmacopeia and the British Pharmacopeia. The term insoluble is often applied to poorly or very poorly soluble compounds.

TABLE 1

| USP and BP solubility criteria | |
|---|---|
| Descriptive term | Part of solvent required per part of solute |
| Very soluble | Less than 1 |
| Freely soluble | From 1 to 10 |
| Soluble | From 10 to 30 |
| Sparingly soluble | From 30 to 100 |
| Slightly soluble | From 100 to 1000 |
| Very slightly soluble | From 1000 to 10,000 |
| Practically insoluble | 10,000 and over |

The negative effect of compounds with low solubility include poor absorption and bioavailability, insufficient solubility for IV dosing, development challenges leading to increasing the development cost and time, and burden shifted to patient (e.g. frequent high-dose administration), to name a few.

A few insoluble drugs have been made soluble. However, this has been very limited due to currently available techniques. One such example is Paclitaxel. Although Paclitaxel is a very potent antineoplastic agent when tested in vitro, it is practically insoluble in blood plasma and is therefore not suitable for systemic delivery without excipients. One commercial formula (Taxol) comprises Paclitaxel in a 1:1 (v/v) mixture of ethanol and Cremophor EL. But while this composition improves the solubility and thus bioavailability of paclitaxel by partitioning the paclitaxel into a non-uniform nanoscale emulsion, the excipients can cause serious negative side effects.

An improved composition of paclitaxel (Abraxane) has been made water-soluble by non-covalently binding paclitaxel with albumin to form a non-uniform nanoscale emulsion. To manufacture this product, Paclitaxel is dissolved in ethanol, then added to an aqueous solution of human serum albumin and precipitated. Albumin-bound paclitaxel is removed by ultrafiltration. The result of this process is the formation of nanoparticles comprised of paclitaxel within a coating of non-covalently bonded albumin. However, the process of creating albumin-coated nanoparticles in a bulk process is not broadly applicable; it leverages the unique characteristics of paclitaxel and albumin to form nanoparticles that happen to perform well as a therapeutic within the complex milieu of the human body. Seemingly similar combinations of molecules do not automatically yield stable particles.

There are no universal fixes for resolving the practical delivery problems of NCEs with low solubility. Likewise, there are few answers for delivering combinations of molecules that perform therapeutic actions together. There are a number of drugs that are only effective in combination with other components yet these drugs and components are unable to be combined for delivery. Therefore, there is currently no way to utilize a whole class of promising new drugs or combinations thereof.

The improved clinical performance of Abraxane, a simple combination of albumin and paclitaxel, over its predecessor, Taxol, suggests that delivering drugs as nanoparticles improves performance, and numerous independent studies support this conclusion. Unfortunately, similar combinations of drugs and excipients do not readily form nanoparticles in bulk. In fact, anticipating which chemistries will form nanoparticles upon mixing is a difficult challenge, let alone finding a combination of molecules that will also act as a therapeutic. The problem of designing drug particles using bulk processes can be thought of as a statistical challenge, where adding more than two molecules together further reduces the chances that they will spontaneously form a nanoparticle. Drug designers often want to combine specific molecules together to act in concert with one another, and bulk condensation reactions, when viewed simply as a statistical problem, cannot possibly be the path forward.

Like other engineered products, drug designers have long desired to create nanoscale particle assemblies, comprised of combinations of different molecules, each with a specific purpose, that are optimized to perform a unique action at a specific moment in the course of events between delivery into the patient until the moment that the intended therapeutic adjustment has been made to a targeted cell. Repeating the success of Abraxane by coating a prospective therapeutic molecule with albumin, or simply fixing the limited solubility aspect of an NDE does not necessarily create a viable therapeutic product. It may require the addition of more than excipients, but combinations of active molecules with complementary actions. For some classes of drugs, most notably anticancer drugs that are designed to trigger cell death, effective targeting is an important attribute of the drug that allow for a lower dose to be administered. A lack of selectivity requires large quantities to be delivered so that at least some of the drug reaches the intended target.

More precise targeting has been achieved by delivering therapeutic molecules with natural viruses. Viruses are extremely efficient at targeting and delivering components to cells. However, the manufacturing process for non-replicating virus particles is typically expensive and cumbersome, often involving human cell culture.

Thus, it is desired to develop improved methods and mechanisms for the production of nanoparticles for the delivery of drugs, particularly insoluble drugs and drug combinations, to patients suffering from conditions and diseases that are out of the reach for the current therapeutics. Many diseases have been characterized at the molecular level creating exciting opportunities to design highly targeted drugs. Modern methods, such as gene expression analysis, have parsed even the most intractable diseases—and their corresponding patient populations—into ever-smaller groups based upon shared markers. It is desired that such targetability and knowledge of patient cohorts with shared biomarkers be utilized for improved patient experiences and outcomes. These methods and mechanisms should be efficient and cost-effective, allowing for new types of treatment to be achieved. At least some of these objectives will be met by the present invention.

SUMMARY OF THE INVENTION

The present invention generally relates to medical systems, devices and methods, and more particularly relates to nanoparticle production with therapeutic application. Likewise, the present invention relates to the following numbered clauses:

1. A system of quants deliverable to a patient having one or more target cells, the system comprising:
a plurality of quants, wherein each quant comprises
one or more component molecules wherein at least one of the one or more component molecules is at least partially hydrophobic; and
a plurality of interface molecules wherein each of the interface molecules has a hydrophilic portion, wherein the plurality of interface molecules are self-arranged having the hydrophilic portions aligned in a shape at least partially surrounding the one or more component molecules, and
wherein each quant in the plurality of quants has the same number and combination of one or more component molecules, and
wherein each quant in the plurality of quants is configured to deliver at least its one or more components molecules to a single target cell of the one or more target cells.

2. A system as in claim 1, wherein the one or more component molecules include drugs, lipids, proteins, antibodies, isotopes, radioactive isotopes, nucleic acid sequences, or any combination of these.

3. A system as in claim 1, wherein the one or more component molecules comprise two or more different component molecules.

4. A system as in claim 1, wherein the one or more component molecules comprise three or more component molecules.

5. A system as in claim 1, wherein the plurality of interface molecules are heterogenous.

6. A system as in claim 1, wherein at least one of the one or more component molecules has a solubility defined as from 1000 to 10,000 parts of solvent required per part of solute.

7. A system as in claim 1, wherein each of the plurality of interface molecules comprises a lipid, a protein, a polymer, or an at least partially amphiphilic molecule.

8. A system as in claim 1, wherein the quants of the plurality of quants are uniform in size with a population coefficient of standard deviation of less than 20%.

9. A system as in claim 1, wherein each quant has a mean diameter of 20 to 300 nanometers.

10. A system as in claim 1, wherein the plurality of quants includes 1 million to 1 billion quants.

11. A system as in claim 1, wherein the one or more component molecules act as a composite assembly on the single target cell in a manner which is unachievable by the one or more component molecules independently.

12. A system as in claim 1, wherein the one or more component molecules are not covalently bound to each other.

13. A system as in claim 1, wherein each quant has at least one molecular recognition motif utilized in recognition by the single target cell.

14. A system as in claim 1, wherein each quant has a net charge.

15. A system as in claim 1, further comprising a second plurality of quants, wherein each quant of the second plurality of quants comprises
one or more component molecules wherein at least one of the one or more component molecules is hydrophobic; and
a plurality of interface molecules wherein each of the interface molecules has a hydrophilic portion, wherein the plurality of interface molecules are self-arranged having the hydrophilic portions aligned in a shape at least partially surrounding the one or more component molecules, and
wherein each quant in the second plurality of quants has the same number and combination of one or more components as each other in the second plurality of quants, and
wherein each quant in the second plurality of quants is configured to deliver its one or more component molecules to a single target cell of one or more target cells.

16. A system as in claim 15, wherein the plurality of quants and the second plurality of quants each have different activity upon the one or more target cells.

17. A system as in claim 15, wherein the one or more component molecules of the plurality of quants differs from the one or more component molecules of the second plurality of quants.

18. A system as in claim 15, wherein the plurality of interface molecules of the plurality of quants differs from the plurality of interface molecules of the second plurality of quants.

19. A system as in claim 15, wherein quants of the plurality of quants have a first mean diameter and quants of the second plurality of quants have a second mean diameter which differs from the first mean diameter.

20. A system as in claim 15, wherein the second plurality of quants includes at least 1 million quants.

21. A system as in claim 15, wherein each quant of the plurality of quants has a first net charge and each quant of the second plurality of quants has a second net charge which differs from the first net charge.

22. A system as in claim 15, wherein the plurality of quants and the second plurality of quants are combined to form a dose deliverable to a patient.

23. A quant deliverable to a single target cell within a patient, wherein the quant comprises: one or more component molecules wherein at least one of the one or more component molecules is at least partially hydrophobic; and a plurality of interface molecules, wherein each of the interface molecules has a hydrophilic portion, wherein the plurality of interface molecules are self-arranged having the hydrophilic portions aligned in a shape at least partially encapsulating the one or more component molecules, and wherein the quant is configured to deliver at least its one or more component molecules to the single target cell.

24. A microfluidic partitioning system comprising:
a base station superstructure comprising
a first fluid inlet for receiving a first fluid,
a second fluid inlet for receiving a second fluid,
an indexer configured to receive the first and second fluids and generate a coaxial flow along a longitudinal axis having a core flow comprised of the first fluid surrounded by a sheath flow comprised of the second fluid; and
an extruder connected with the indexer so as to receive the coaxial flow, wherein the extruder includes at least one microfluidic channel configured receive the coaxial flow and to allow the core flow to form droplets within the sheath flow at a linear flow rate of one meter per second.

25. A system as in claim 24, wherein the base station superstructure further comprises at least one mechanism for transporting the first and second fluids to the indexer so that pressure within the indexer is at least 100 psi.

26. A system as in claim 24, further comprising the first fluid wherein the first fluid comprises a plurality of hydrophobic component molecules and a plurality of interface molecules each interface molecule having a hydrophilic portion, and further comprising the second fluid, wherein the second fluid comprises an aqueous solution, and wherein each droplet comprises one or more of the plurality of hydrophobic component molecules and a portion of the plurality of interface molecules so that the hydrophilic portions of the interface molecules are able to self-arrange in a shape at least partially encapsulating the one or more of the plurality of component molecules.

27. A system as in claim 24, further comprising a mechanism configured to extract a quantity of the first fluid from each droplet so that each droplet forms a quant which is substantially solid.

28. A system as in claim 27, wherein each quant has a diameter of 20 to 300 nanometers.

29. A system as in claim 27, wherein each quant is of the same size so that any grouping of quants are uniform in size with a population coefficient of standard deviation of less than 20%.

30. A system as in claim 27, wherein the mechanism comprises a membrane.

31. A system as in claim 27, wherein the extruder comprises an attachment feature that seals the extruder to a reservoir so as to allow transfer of each quant to the reservoir.

32. A system as in claim 31, wherein the reservoir comprises a bottle, a vial, a syringe or an IV drip bag.

33. A system as in claim 24, wherein the microfluidic channel has length of between 5 and 100 millimeters.

34. A system as in claim 24, wherein a linear flow rate of the coaxial flow in the microfluidic channel is approximately 1-20 meters per second.

35. A system as in claim 24, wherein the core flow is not more than 2 micrometers in diameter.

36. A system as in claim 24, wherein the sheath flow is approximately 3-40 micrometers in outer diameter.

37. A system as in claim 24, wherein the ratio of the core flow to the sheath flow is approximately 1:1000.

38. A system as in claim 24, wherein the first and second fluids form a fluid interface within the indexer which is perpendicular to the longitudinal axis.

39. A system as in claim 38, wherein the first fluid inlet is disposed above the second fluid inlet and wherein the fluid interface is disposed between the first and second fluid inlets.

40. A system as in claim 24, wherein the extruder is removable from the indexer.

41. A system as in claim 40, wherein the extruder is connected to the indexer by a reversible interlocking seal.

42. A system as in claim 40, further comprising another extruder which is attachable to the indexer in place of the extruder.

43. A system as in claim 42, wherein the extruder and the another extruder are comprised of different materials.

44. A system as in claim 42, wherein the extruder and the another extruder have at least one differing microfluidic channel from each other.

45. A system as in claim 40, wherein the extruder has an identifier which is readable by the base station superstructure.

46. A system as in claim 24, wherein the base station superstructure includes a computer control unit which controls at least the at least one mechanism for transporting the first and second fluids to the indexer.

47. A system as in claim 46, wherein the at least one microfluidic channel comprises a single microfluidic channel having a first end and a second end, the system further comprising a first electrode disposed near the first end of the microfluidic channel and a second electrode disposed near the second end of the microfluidic channel, wherein the computer control unit monitors an electronic signal generated by an electric current passing between the first and second electrodes.

48. A system as in claim 46, wherein the computer control system is able to reprogram at least the at least one mechanism for transporting the first and second fluids to the indexer based on the electronic signal.

49. A system as in claim 24, wherein the base station superstructure further comprises a third fluid inlet for receiving a third fluid so as to combine the third fluid within the first fluid, wherein the third fluid is miscible with the first fluid so that the core flow is comprised of the first and third fluids.

50. A system as in claim 24, wherein the indexer further comprises a waste line configured to allow removal of fluids from the indexer.

51. A system as in claim 24, wherein the indexer further comprises a pulsed energy source configured to introduce controlled perturbations to the coaxial flow.

52. A system as in claim 51, wherein the pulsed energy source comprises a laser diode, a piezo ceramic, and/or a voltage source.

53. A microfluidic extruder comprising:
an elongate body having proximal end, a distal end and a longitudinal axis, wherein the proximal end is configured to removably attach to an indexer and the distal end is configured to removably attach to a collection reservoir; and
a microfluidic channel extending along the longitudinal axis from the proximal end to the distal end, wherein the microfluidic channel is configured to receive coaxial flow along the longitudinal axis from the indexer, wherein pressure within the indexer is at least 100 psi and the coaxial flow in the microfluidic channel is approximately 1-20 meters per second, and wherein the microfluidic channel has a length configured to allow the coaxial flow to form droplets therein.

54. A microfluidic extruder as in claim 53, wherein the microfluidic channel has a length of between 5 and 100 millimeters.

55. A microfluidic extruder as in claim 53, wherein the microfluidic channel has a cross-sectional area of between 0.1 square micrometers and 10,000 square micrometers.

56. A microfluidic extruder as in claim 53, wherein the microfluidic channel has a cross-sectional area which is larger near the distal end than near the proximal end.

57. A microfluidic extruder as in claim 53, wherein the proximal end includes an interlocking feature configured to mate with an outlet port of the indexer.

58. A microfluidic extruder as in claim 57, wherein the proximal end has a tip and the interlocking feature is configured to mate with the outlet port so that the tip of the proximal end is disposed within an indexing chamber of the indexer.

59. A microfluidic extruder as in claim 58, wherein the interlocking feature is configured to mate with the outlet port so that the tip of the proximal end is disposed within 1 mm of a fluid interface within the indexing chamber, wherein the fluid interface is formed between fluids which form the coaxial flow.

60. A microfluidic extruder as in claim 57, wherein the interlocking feature has a conical mating surface.

61. A microfluidic extruder as in claim 53, wherein the microfluidic channel has a first end and a second end, the extruder further comprising a first electrode disposed near the first end of the microfluidic channel and a second electrode disposed near the second end of the microfluidic channel, wherein electric current passing between the first and second electrodes generates an electronic signal characterizing the coaxial flow.

62. A microfluidic extruder as in claim 53, further comprising an identifier which is readable by using a bar code reader or RF tag reader.

63. A microfluidic extruder as in claim 53, wherein the reservoir comprises a bottle, a vial, a syringe or an IV drip bag.

64. A microfluidic system comprising:
a microfluidic channel having a first end and a second end, wherein the microfluid channel is configured to pass a coaxial flow, wherein the coaxial flow comprises a core flow of a first fluid and a surrounding sheath flow of a second fluid, wherein one of the first and second fluids is conductive while the other of the first and second fluids is non-conductive;
a first conductor disposed along the microfluidic channel;
a second conductor spaced apart from the first conductor disposed along the microfluidic channel;
a controller bus joining the conductor and the another conductor, wherein the controller bus is configured to generate an electrical measurement of the coaxial flow between the conductor and another conductor; and
a computer electrically connected with the controller bus and configured to analyze the electrical measurement in real time.

65. A microfluidic system as in claim 64, wherein the electrical measurement is a value of voltage, current, resistance, conductance, capacitance, charge, inductance, power, impedance, and/or frequency.

66. A microfluidic system as in claim 65, wherein the computer compares the electrical measurement to a database of control electrical measurements and provides an output if the electrical measurement corresponds to a control electrical measurement in the database of control electrical measurements.

67. A microfluidic system as in claim 65, wherein the computer compares the electrical measurement to a database of control electrical measurements and provides an output if the electrical measurement does not correspond to a control electrical measurement in the database of control electrical measurements.

68. A microfluidic system as in claim 66 or 67, wherein the output comprises an auditory signal.

69. A microfluidic system as in claim 66 or 67, wherein the output comprises a visual signal or readout.

70. A microfluidic system as in claim 66 or 67, wherein the controller bus changes the coaxial flow in response to the output.

71. A microfluidic system as in claim 64, further comprising a pulsed energy source configured to introduce controlled perturbations to the coaxial flow.

72. A microfluidic system as in claim 71, wherein the pulsed energy source comprises a laser diode, a piezo ceramic, and/or a voltage source.

73. A method of generating a quant comprising: inputting a first fluid and a second fluid into an indexer chamber so that pressure within the indexing chamber is at least 100 psi and so that the first and second fluids form a coaxial flow through an outlet of the indexing chamber and into a microfluidic channel of an extruder wherein droplets of the first fluid form at a rate of at least 100 kHz; and
extracting at least a portion of the first fluid from each droplet so that each droplet forms a quant which is substantially solid.

74. A method as in claim 73, wherein the first fluid comprises one or more component molecules and a plurality of interface molecules, wherein at least one of the one or more component molecules is hydrophobic and each of the interface molecules has a hydrophilic portion.

75. A method as in claim 74, wherein each quant is comprised of interface molecules arranged so that their hydrophilic portions form a sphere surrounding one or more component molecules wherein at least one of the component molecules is hydrophobic.

76. A method as in claim 75, wherein the one or more component molecules comprise drugs, lipids, proteins, antibodies, isotopes, radioactive isotopes, nucleic acid sequences or any combination of these.

77. A method as in claim 75, wherein the one or more component molecules comprise two or more different component molecules.

78. A method as in claim 75, wherein the component molecules comprise three or more component molecules.

79. A method as in claim 73, wherein each quant has a mean diameter of 20 to 300 nanometers.

80. A method as in claim 73, further comprising adjusting the inputting step to cause the droplets to form at a different rate.

81. A method as in claim 73, further comprising generating an electrical measurement of the coaxial flow, wherein the electrical measurement is a value of voltage, current, resistance, conductance, capacitance, charge, inductance, power, impedance, and/or frequency.

82. A method as in claim 81, further comprising adjusting the inputting step based on the electrical measurement.

83. A method as in claim 73, further comprising collecting at least some quants into a reservoir configured for delivery to a patient.

84. A method as in claim 73, further comprising removing the extruder from the outlet of the indexer and replacing with the same extruder or a different extruder.

85. A method as in claim 84, further comprising unclogging the microfluidic channel of the extruder after removing the extruder from the outlet of the indexer and before replacing with the same extruder or a different extruder.

86. A method as in claim 73, further comprising introducing controlled perturbations to the coaxial flow.

87. A system for the initiation of a microfluidic coaxial flow of at least two fluids comprising: an indexer comprising an indexing chamber, at least two fluid inlets in fluid communication with the indexing chamber and an outlet in fluid communication with the indexing chamber; and
an extruder comprising an elongate body having proximal end, a distal end and a longitudinal axis, wherein the proximal end is configured to attach to the outlet of the indexer, wherein the extruder includes at least one microfluidic channel that is open at both ends forming an inlet at the proximal end and an outlet at the distal end, and wherein the indexer is configured receive the least two fluids and initiate coaxial flow of the least two fluids which passes through at least a portion of the microfluidic channel 88. A system as in claim 87, wherein the indexer and extruder are separate components that are reversibly connected by means of an interlocking feature and pressure seal.

89. A system as in claim 88, wherein the interlocking feature comprises a threaded port.

90. A system as in claim 88, wherein the interlocking feature comprises a conical port.

91. A system as in claim 88, wherein the interlocking feature is secured by finger-tightening alone.

92. A system as in claim 87, wherein the at least two fluids comprise a first fluid and a second fluid that are immiscible.

93. A system as in claim 87, further comprising a pulsed energy source configured to introduce controlled perturbations to the coaxial flow and/or a fluid interface.

94. A system as in claim 93, wherein the pulsed energy source comprises a laser diode, piezo element, voltage source, or a combination of these.

95. A system as in claim 87, wherein the outlet has a conical mating surface and the proximal end of the extruder is configured to form a fluid tight seal against the conical mating surface in an arrangement so that the longitudinal axis of the extruder is aligned with a central axis of the indexing chamber.

96. A system as in claim 87, wherein an indexer retains and positions a fluid interface substantially perpendicular to the longitudinal axis of the extruder.

97. A system as in claim 87, wherein the indexer retains a fluid interface at a distance not more than 1 millimeter from the proximal end of the extruder.

98. A system as in claim 87, wherein the indexing chamber is cylindrical with a diameter of between 100 and 3,000 micrometers 99. A system as in claim 87, wherein the diameter is between 200 and 1000 micrometers.

100. A system as in claim 87, wherein the indexing chamber is comprised of a chemically inert material, stainless steel, titanium, aluminium, Polyphenelyene Sulphide (PPS), Polytetrafluoroethylene (PTFE), Polyetherether, Ketone (PEEK), Polyoxymethylene (POM), Ethylene Propylene Diene (EPDM), Ethylene Tetrafluoroethylene (ETFE), Polypropylene (PP), Chlorotrifluoroethylene (PCTFE/CTFE) or any combination of these.

101. A system as in claim 87, wherein the microfluidic flow channel has a length of between 5 and 100 millimeters.

102. A system as in claim 87, wherein the microfluidic flow channel has a cross-sectional area of between 0.1 square micrometers and 10,000 square micrometers.

103. A system as in claim 87, wherein the cross-sectional area of the microfluidic flow channel is larger at the distal end of the extruder than it is at the proximal end of the extruder.

104. A system as in claim 87, wherein the indexer includes mounting features configured to attach the indexer to a non-disposable structure, wherein the mounting features comprise through holes or threaded ports.

105. A system as in claim 87, wherein the indexer further comprises a port connected to a waste line.

106. A system as in claim 87, wherein the indexer comprises at least three fluid inlets in fluid communication with the indexing chamber, and wherein each of the at least three fluid inlets is configured to receive a different fluid.

107. A system as in claim 87, further comprising at least one fluid containing dissolved or suspended solids.

108. A system as in claim 87, wherein the indexing chamber has a fluid pressure of at least 100 psi (~689 kPa).

109. A system as in claim 108, wherein the indexing chamber has a fluid pressure of at least 1000 psi (~6,890 kPa).

110. A system as in claim 109, wherein the indexing chamber has a fluid pressure of at least 10,000 psi (~68,900 kPa).

111. A system as in claim 87, wherein at least one of the at least two fluid inlets is coupled to at least one positive displacement pump.

112. A system as in claim 87, wherein at least one of the at least two fluid inlets is coupled to a fluid supply system having at least one fluid reservoir, at least one filter, at least one positive displacement pump and at least one pulse dampener.

113. An apparatus for the measurement and control of a coaxial fluid flow of at least two fluids flowing along a microfluidic pathway of a microfluidic circuit, wherein an outer sheath fluid of the coaxial fluid flow is conductive, comprising
a mechanism for initiating and directing the coaxial fluid flow into one end of the microfluidic pathway;
a mechanism for establishing an electrical current flow along a length of the microfluidic pathway;
a mechanism for detecting an electrical signal across the length of the microfluidic pathway;
a mechanism for characterizing the coaxial fluid flow by identifying corresponding changes in a circuit signal.

114. An apparatus as in claim 113, wherein the microfluidic circuit is comprised of a separable microfluidic initiator and an extruder having at least one microfluidic channel enclosing the coaxial flow of the at least two fluids, wherein the microfluidic initiator comprises an indexer body and a distal end of the extruder providing a conductive pathway between incoming and outflowing fluids respectively.

115. An apparatus as in claim 114, wherein the indexer body is grounded, and the distal end of the extruder is connected to a computer-controlled voltage source.

116. An apparatus as in claim 113, wherein the outer sheath fluid comprises an aqueous buffer.

117. An apparatus as in claim 113, wherein an inner fluid of the coaxial flow comprises a solvent system containing at least one dissolved molecular species.

118. An apparatus as in claim 113, wherein the mechanism for detecting the electrical signal across the length of the microfluidic pathway comprises a mechanism to measure one or more of voltage (Volt), current (Ampere), resistance (Ohm), conductance (Siemen), capacitance (Farad), charge (Coulomb), inductance (Henry), power (Watt), impedance (Ohm), and frequency (Hertz).

119. An apparatus as in claim 113, wherein the mechanism of detecting the electrical signal across the length of the microfluidic pathway further comprises a computer with data storage and a reference.

120. An apparatus as in claim 113, further comprising a user input interface.

121. An apparatus as in claim 113, further comprising a mechanism for tracking microfluidic circuit measurements and user inputs related to device troubleshooting, maintenance, and/or billing on a per-particle basis.

122. An apparatus as in claim 113, further comprising a mechanism to control hardware affecting fluid flow conditions along the microfluidic pathway, wherein the flow conditions comprise pressure, temperature or flow rate, and wherein the mechanism controls the hardware in response to the electrical signal across the length of same microfluidic pathway.

123. An apparatus as in claim 113, further comprising a mechanism to control a pulsed energy source affecting breakup of the coaxial flow within a microfluidic channel into meaningfully uniform droplets based on the electrical signal across the length of same microfluidic pathway.

124. An apparatus for the measurement and control of a coaxial fluid breakup into meaningfully uniform droplets comprising:
a mechanism for initiating and directing a coaxial fluid flow into one end of a microfluidic pathway;
a mechanism for establishing an electrical current flow along a length of the microfluidic pathway;
a mechanism for detecting an electrical signal across the length of the microfluidic pathway;
a mechanism for characterizing the coaxial fluid flow by identifying corresponding changes in a circuit signal;
a mechanism for coupling a pulsed energy source into a fluid interface or the coaxial fluid flow; and
a mechanism for driving said pulsed energy source.

125. A method for the measurement and control of a coaxial fluid flow and breakup into meaningfully uniform droplets, comprising changing pressure, temperature, flow rate, frequency, amplitude, or waveform of the coaxial fluid flow in reference to a measurement of an electrical circuit down a length of a microfluidic channel to adjust the physical dimensions of the coaxial flow and regular downstream breakup of the coaxial flow into meaningfully uniform droplets within the microfluidic channel 126. An apparatus for microfluidic partitioning comprising;
a separable microfluidic coaxial flow initiator comprised at least one indexer having at least a first fluid inlet port and a second fluid inlet port;
a microfluidic circuit comprising at least one extruder; and
a mechanism for supplying at least one first fluid into the first fluid inlet port and at least one second fluid into the second fluid inlet port,
wherein the at least one first fluid and the at least one second fluid are substantially immiscible,
wherein the at least one first fluid comprises a non-aqueous solvent system containing at least one dissolved molecular species and wherein the at least one second fluid comprises an aqueous solution, and
wherein a steady coaxial flow of the at least one first fluid and the at least one second fluid is sustained and caused to break into meaningfully uniform partitions while passing through the extruder.

127. An apparatus for microfluidic partitioning comprising;
a separable microfluidic coaxial flow initiator comprised of one indexer and one extruder in an assembled configuration, wherein the extruder comprises a microfluidic circuit; and
a mechanism for conducting a steady pressurized supply of a first fluid and a second fluid to the indexer via a first fluid inlet port and a second fluid inlet port, respectively,
wherein the first fluid and the second fluid are substantially immiscible,
wherein the first fluid comprises a non-aqueous solvent system containing at least one dissolved molecular species,
wherein the second fluid comprises an aqueous solution, and
wherein a steady coaxial flow of the first and second fluids is sustained and caused break into meaningfully uniform partitions while passing through the extruder.

128. An apparatus as in claim 127, further comprising a control system, wherein the control system further comprises a computer.

129. An apparatus as in claim 127, wherein the separable microfluidic coaxial flow initiator is reversibly separable into two separate segments by a single interlocking mechanism that connects the indexer and extruder.

130. An apparatus as in claim 129, wherein the interlocking mechanism comprises a mechanically interlocking interface, a seating surface, and at least one electrically conductive contact, or a combination thereof.

131. An apparatus as in claim 129, where extruder is attached and detached manually by rotation.

132. An apparatus as in claim 127, wherein the extruder includes a microfluidic channel having a variable mean diameter along its length.

133. An apparatus as in claim 132, wherein the microfluidic channel has a diameter which is smallest near its proximal end.

134. An apparatus as in claim 127, wherein the extruder contains an interlocking mechanism near its distal end that seals at least one of the first fluid inlet port and the second fluid inlet port to a fixture.

135. An apparatus as in claim 134, wherein the interlocking mechanism comprises a luer lock, threaded feature, mechanical, or interference fit port.

136. An apparatus as in claim 127, wherein a distal end of the extruder is mechanically, fluidly, or electrically attached to a reservoir or a mechanism for downstream processing of output fluid.

137. An apparatus as in claim 127, wherein the fluids flowing through the extruder are connected directly to a patient via an intravenous connection.

138. An apparatus as in claim 127, wherein the extruder is disposable.

139. An apparatus as in claim 127, wherein the extruder is identifiable to a control system using a bar code or RF tag.

140. An apparatus as in claim 127, wherein the extruder contains a semipermeable membrane.

141. An apparatus as in claim 127, wherein the extruder contains a solvent absorptive material.

142. An apparatus as in claim 127, wherein the extruder further comprises at least one reagent reservoir containing a fluid reagent having a type and volume corresponding a particular assay or function.

143. A method of generating a steady flow of meaningfully uniform partitions in an extruder comprising:
generating an unstable coaxial flow of two immiscible fluids in the extruder, wherein a first fluid of the two immiscible fluids is a solvent and a second fluid if the two immiscible fluids is an aqueous solution, wherein the extruder is installed into a base station comprising at least one indexer and at least one upstream fluid supply system.

144. A method as in claim 143, wherein the first fluid comprises an organic and/or halogenated solvent.

145. A method as in claim 143, wherein the second fluid comprises a buffered aqueous solution.

146. A method as in claim 143, wherein coaxial instability is controlled with a source of pulsed energy is coupled to the coaxial flow.

147. A system comprising a collection of at least 1 million separate multicomponent drug assemblies stably dispersed in an aqueous solution, wherein each molecular assembly
a) is functionally uniform,
b) is capable of uptake by a single cell of the type targeted,
c) is comprised of at least 3 molecular species, wherein at least one is a drug,
d) measures between 20 and 200 nanometers in mean diameter with a population coefficient of standard deviation (% CV) of less than 20%, and
e) is substantially uniform in terms of molecular composition such that proportions of each constituent molecule comprising molecular assembly varies by less than a population coefficient of standard deviation (% CV) of less than 20% CV.

148. A system as in claim 147, wherein a mean diameter population coefficient of standard deviation (% CV) is less than 10%.

149. A system as in claim 148, wherein the mean diameter population coefficient of standard deviation (% CV) is less than 5%.

150. A system as in claim 147, wherein the proportions of each constituent molecule comprising the molecular assembly varies by less than a population coefficient of standard deviation (% CV) of less than 10%.

151. A system as in claim 150, wherein the proportions of each constituent molecule comprising the molecular assembly varies by less than a population coefficient of standard deviation (% CV) of less than 5%.

152. A system as in claim 147, wherein each molecular assembly is arranged at a molecular level by constituent molecules gathered at a surface or interior to form particles with a distinct morphology characteristic of their molecular makeup.

153. A system as in claim 147, wherein the at least three molecular species includes at least one lipid or aliphatic molecular species.

154. A system as in claim 147, wherein the drug is comprised of RNAi and/or chemotherapeutics.

155. A system as in claim 147, wherein each molecular assembly carries a net charge.

156. A system as in claim 147, wherein the at least three molecular species includes at least one nucleic acid.

157. A system as in claim 147, wherein the at least three molecular species includes at least one CRISPR-related protein.

158. A method of producing a collection of at least one million meaningfully uniform multicomponent particles comprising:
mixing at least three molecular species with a solvent system to create a hydrophobic reagent fluid; flowing the hydrophobic reagent fluid within a sheath of an aqueous fluid to create a laminar coaxial flow in a microfluidic channel, wherein the hydrophobic reagent fluid is divided into uniform partitions while still in laminar coaxial flow;
leaching the solvent system from the uniform microdroplets into the surrounding aqueous sheath fluid at a rate so that the solutes remain entrapped in a collection of shrinking partitions, wherein each partition forms a multicomponent particle; and
collecting the multicomponent particles and aqueous fluid in an injectable particle suspension.

159. A method in claim 158, wherein at least one of the at least three molecular species comprises a drug or has a therapeutic effect.

160. A method as in claim 158, wherein the microfluidic channel is disposed within an extruder of a separable coaxial flow generator.

161. A method as in claim 158, wherein the flowing the hydrophobic reagent fluid is not more than 2 micrometers in diameter.

162. A method as in claim 158, wherein a linear flow rate of the coaxial flow is at least 1.5 meters per second.

163. A method as in claim 158, wherein a ratio of the flowing the hydrophobic reagent fluid to the sheath of aqueous fluid while in coaxial flow is approximately 1:1000.

164. A method as in claim 158, wherein a diameter of the flowing the hydrophobic reagent fluid while in coaxial flow is approximately 1 micrometer.

165. A method as in claim 158, wherein an outer diameter of the sheath of aqueous fluid while in coaxial flow is approximately 30 micrometers.

166. A method as in claim 158, wherein flowing the hydrophobic reagent fluid within a sheath of an aqueous fluid occurs within an indexer at a pressure of at least 1000 psi.

167. A method as in claim 166, wherein flowing the hydrophobic reagent fluid within a sheath of an aqueous fluid occurs within an indexer at a pressure of at least 10,000 psi.

168. A method as in claim 167, wherein flowing the hydrophobic reagent fluid within a sheath of an aqueous fluid occurs within an indexer at a pressure at least 20,000 psi.

169. A method as in claim 158, wherein a frequency of droplet production is at least 500 kHz.

170. A method as in claim 169, wherein a frequency of droplet production is at least 1 MHz.

171. A method as in claim 158, wherein each multicomponent particle has a diameter between 5 nanometers and 300 nanometers.

172. A method as in claim 171, wherein each multicomponent particle has a diameter of about 100 nanometers.

173. A method as in claim 158, wherein the microdroplets are produced with a mean diameter as measured as a population coefficient of standard deviation (% CV) of not more than 50%.

174. A method as in claim 173, wherein the microdroplets are produced with a mean diameter as measured as a population coefficient of standard deviation (% CV) of not more than 40%.

175. A method as in claim 174, wherein the microdroplets are produced with a mean diameter as measured as a population coefficient of standard deviation (% CV) of not more than 30%.

176. A method as in claim 175, wherein the microdroplets are produced with a mean diameter as measured as a population coefficient of standard deviation (% CV) of not more than 20%.

177. A method as in claim 176, wherein the microdroplets are produced with a mean diameter as measured as a population coefficient of standard deviation (% CV) of not more than 10%.

178. A method as in claim 158, wherein flowing the hydrophobic reagent fluid within the sheath of the aqueous fluid is achieved with the use of a volumetric positive displacement pump.

179. A method as in claim 158, further comprising a microfluidic control circuit.

180. A method as in claim 158, further comprising a pulsed energy source coupled into the coaxial fluid flow such that droplet separation occurs at a set rate.

181. A method as in claim 158, wherein collecting the multicomponent particles and aqueous fluid in an injectable particle suspension.generates a known quantity and concentration due to their digital manufacture.

182. A system comprising a first plurality of at least one million separate molecular assemblies stably dispersed in an aqueous solution, wherein each molecular assembly
a) is functionally uniform,
b) is capable of uptake by a targeted cell,
c) is comprised of at least 3 molecular species,
d) measures between 20 and 200 nanometers in mean diameter with a population coefficient of standard deviation of less than 20%, and
e) is substantially uniform in terms of molecular composition such that the proportions of each constituent molecular species varies between molecular assemblies by a population coefficient of standard deviation of less than 20%.

183. A system as in claim 182, further comprising a second plurality of at least one million molecular assemblies, wherein each of the second plurality is distinct from each of the first plurality.

184. A system as in claim 182, wherein each molecular assembly further comprises a mechanism of delivering a genomic sequence into a targeted cell.

185. A system as in claim 182, wherein each molecular assembly further comprises a mechanism of delivering nucleic acids that enable gene editing into a targeted cell.

186. A system as in claim 182, wherein each molecular assembly further comprises a mechanism of delivering a genomic sequence and protein that enable gene editing as consistent with CRISPR.

187. A system as in claim 182, wherein at least one of the at least three molecular species is cytotoxic or a poison.

188. A method of delivering quants, wherein each quant is administered intravenously.

189. A method of dosing quants, wherein a number of particles comprising a single dose is determined by estimating a number of target cells relative to a number of non-target cells.

190. A method for determining a number (Q) of quants, comprising a therapeutic dose based on an equation:

$$T - C = \sum_{n=1}^{Q} \left[ \left( \frac{T}{M} \right) KE \right]_n$$

Where: T=target cells
C=cumulative target cells treated
Q=number of quants
M=number of non-target cells in patient
E=effectivity
K=number of cells encountered per second 191. A method of producing a spectrum of quants directed to a single targeted cell type whereby at least one of a constituent nucleic acid is modified.

192. A method as in claim 191, wherein the modifications are designed to interact with specific genomic sequences present in target cells.

193. A method of preparing a personalized medicine, wherein at least one species of quant is prepared from a mixture of reagents to include at least one molecule chosen or created in response to genomic data acquired from a single patient.

194. A method of preparing a personalized medicine, wherein a collection of quant species are prepared, each to include at least one molecule from a database of nucleic acid sequences chosen or created in response to the clinical success of other patients with a similar profile.

195. A method of determining a dose of quants sufficient to treat a patient, the method comprising:
determining a quantity of target cells within the patient;
estimating a statistical likelihood of a single quant in reaching one of the quantity of target cells; and
calculating the dose of quants that is sufficient to treat the quantity of target cells within the patient based on the determined quantity of target cells and the estimated statistical likelihood of the single quant in reaching one of the quantity of target cells.

196. A method as in claim 195, wherein the quantity of target cells comprises a quantity of tumor cells within a tumor.

197. A method as in claim 195, wherein the estimating step comprises estimating a number of cells that a single quant will encounter while in the patient.

198. A method as in claim 195, wherein the estimating step comprises estimating an effectivity value for the single quant, wherein the effectivity value corresponds to a statistical likelihood that the single quant will effectively enter one of the quantity of target cells.

199. A method as in claim 195, wherein the estimating step comprises calculating a quantity of non-target cells within the patient.

200. A method as in claim 195, wherein the calculating step utilizes the following formula:

$$T - C = \sum_{n=1}^{Q} \left[ \left( \frac{T}{M} \right) KE \right]_n$$

Where: T=target cells
C=cumulative target cells treated
Q=number of quants
M=number of non-target cells in patient
E=effectivity
K=number of cells encountered per second 201. A method as in claim 195, wherein each quant comprises
one or more component molecules wherein at least one of the one or more component molecules is at least partially hydrophobic; and a plurality of interface molecules, wherein each of the interface molecules has a hydrophilic portion, wherein the plurality of interface molecules are self-arranged having the hydrophilic portions aligned in a shape at least partially encapsulating the one or more component molecules, and wherein the quant is configured to deliver at least its one or more component molecules to the single target cell.

Some aspects of the invention involve a method of generating a steady flow of meaningfully uniform partitions in a disposable extruder by first generating an unstable coaxial flow of two immiscible fluids, wherein the first fluid is a solvent, and the second fluid is an aqueous solution, and the disposable extruder is installed into a base station superstructure comprising at least one indexer and at least one upstream fluid supply system. Meaningfully uniform is typically considered to relate to a collection of items with a shared attribute that can be measured with a coefficient of variation of 20% or less. In some embodiments, the first fluid is selected from the group of organic and halogenated solvents and the second fluid is a buffered aqueous solution. In some embodiments, the base station superstructure further comprises the ability to modulate the coaxial instability by virtue of a source of pulsed energy that is coupled to the coaxial flow built into the indexer.

Many embodiments of the disclosed invention are directed toward personalized medicine by rational drug design, which will involve the high speed production of unique and complicated formulations, often comprising multiple distinct particle types.

Some embodiments described herein include a method and apparatus for assembling nanoscale multicomponent drug particles by sequestering drug particle constituents in droplets in a nearly immiscible solvent.

Some embodiments described herein include a means of assembling molecular components into uniform particles with specific and predetermined attributes. As the surface area of the enclosure is reduced, the molecules inside it are forced to interact with each other to find new conformations and stabilities.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 18A-18C are sectional views of an embodiment of an assembled indexer and extruder combination in three different states of fluid flow, demonstrating the variable position of the fluid interface within the indexer relative to the proximal end of the extruder, and its effect on coaxial fluid flow.

FIG. 19 is a sectional view of an embodiment of an assembled indexer and extruder combination with three fluid ports, demonstrating the flow of three fluids to form a collection of droplets.

FIG. 20 is a sectional view of an embodiment of an assembled indexer and extruder combination with four fluid ports, demonstrating the flow of four fluids to form a collection of droplets.

FIGS. 29A-29F illustrates various example fluid flow conditions that could occur in a microfluidic pathway, such as the microfluidic channel.

DETAILED DESCRIPTION OF THE INVENTION

Specific embodiments of the disclosed apparatuses, systems and methods will now be described with reference to the drawings. Nothing in this detailed description is intended to imply that any particular component, feature, or step is essential to the invention.

The apparatuses, systems and methods described herein relate to the field of Nanomedicine. Nanomedicine is the medical application of nanotechnology. Nanomedicine is typically concerned with partitioning a single drug dose into an emulsion of particles prior to delivery. A drug is typically considered a molecular species (i.e. a particular type of molecule) with a specific biological action delivered with intended effect. Producing nanoscale drug particles from bulk reagents has traditionally been considered a chemical challenge. Indeed, condensation reactions are the foundation of most nanodrug manufacturing efforts. Although familiar and ubiquitous, the method is limited, making it impossible to produce some molecular combinations. Simple combinations can be accommodated, e.g. Doxil, Abraxane, and Onivyde, but the most promising formulations are more complex associations of molecular combinations—highly structured synthetic virus-like nanoparticles—that are beyond the reach of current technologies.

Thus, methods and apparatuses for producing such virus-like nanoparticles are described herein. By considering each drug particle as a distinct therapeutic entity with well-defined physical and chemical characteristics, and providing the means to produce uniform drug particles with predefined characteristics, the concept of an engineered nanoscale multicomponent particle is introduced and called a "quant." By controlling the variables of manufacture, such as particle size and composition, and by redefining a drug dose as the measured number of quants delivered (as opposed to measuring a drug dose by the mass of its active ingredient), the performance of nanoparticle-based drugs can be better understood, measured, compared and improved. Whereas in the past medications comprised of soluble compositions or inadequately controlled emulsions have been developed successfully using mass as a convenient proxy measurement for the number of discrete molecules or particles delivered, the composite nature of nanoparticles dictates that we must transform the lexicon of drug dosing to accommodate a new class of drugs that are best described in terms of discrete units. After all, one milligram of a drug emulsion can equally represent one million or one billion discrete particles, depending on particle size. Likewise, measuring a dose of virus particles by mass alone would not make sense. This new class of precision medicines will introduce significant efficiencies and much higher value products to the expanding therapeutics market.

Concept of a Quant

Figure 1:
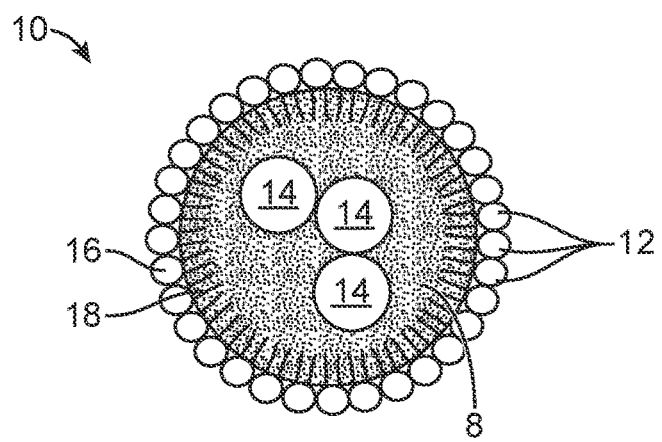
FIG. 1 provides a stylized cross-sectional illustration of an embodiment of a quant.

A quant is a functionally uniform drug particle characterized by a specific molecular composition and characteristic three-dimensional structure, or morphology. FIG. 1 provides a stylized cross-sectional illustration of an embodiment of a quant 10. In this embodiment, the quant 10 is comprised of a plurality of interface molecules 12 surrounding one or more component molecules 14 suspended in a carrier oil 8. Each interface molecule 12 is typically amphiphilic having a hydrophilic portion (such as a hydrophilic head 16) and a hydrophobic tail 18. The interface molecules 12 are arranged so that the hydrophilic heads 16 face outward forming a sphere while the hydrophobic tails 18 reside within the carrier oil 8. The one or more component molecules 14 reside within the sphere formed by the interface molecules 12. In this embodiment, three component molecules 14 are present, however, more complex molecular mixtures can be produced and may be desired. The component molecules 14 may include a variety of different types of molecules including drugs, lipids, proteins, antibodies, isotopes, radioactive isotopes and nucleic acid sequences, to name a few. Likewise, the interface molecules 12 may be homogeneous or heterogenous. In some embodiments, one or more of the component molecules 14 are hydrophobic. In such instances, the hydrophilic sphere of heads 16 surrounding the hydrophobic component molecules 14 allows the hydrophobic (water insoluble) component molecules 14 to be delivered to the body as if the component molecules 14 were soluble. Thus, the component molecules are able to provide the desired therapy.

In some embodiments, each quant 10 measures between 20 and 300 nanometers in mean diameter. Their small size and uniformity are significant; quants are typically designed to enter cells and in such instances must be scaled accordingly. Quants 10 are morphologically and functionally similar to natural viruses and may therefore be considered their synthetic counterparts. Moreover, quants 10 may be replication competent.

Each quant 10 is designed specifically for cellular uptake. Unlike other drugs, which are typically conceived as a single molecular species, quants 10 are multi-molecular assemblies designed specifically for cellular uptake. Quants 10 perform their intended function by gaining access to living cells. Conventional nanoparticles that are too large to enter targeted cells or conventional nanoparticles that do not contain the unique molecular compositions that are able to be provided by quants 10 simply cannot perform the tasks achievable by quants 10 for which they were designed. For example, quants 10 are able to deliver a plurality of component molecules 14 together to a cell at the same time. This allows component molecules 14 that could not act as a drug individually to now act as a drug that is a composite assembly. Complex actions requiring multiple components can be delivered to the same cell at the same time with the use of a quant 10.

Lipids, proteins, antibodies, isotopes, radioactive isotopes and nucleic acid sequences are ubiquitous in the modern laboratory, as are the platform technologies used to modify them. And for more complex tasks, such as evading the immune system, accessing a cell or a nucleus, or modifying a genome, multiple molecular species are required to act in concert. The totality of biologically significant molecular species that form our understanding of the composition of cells and drugs form a molecular toolbox from which the molecules comprising all elements of quants are drawn. Quants 10 can affect interventions (e.g. intentional manipulation of a biological system) using a variety of molecular species. For example, nucleic acids and proteins can be built into quants 10 to achieve nucleic acid manipulations, such as RNAi, CRISPR, and gene therapy. Such methodologies can be used to alter the natural state of a cell or condition, or to neutralize a disease state. A variety of therapeutic molecules can be transported by quants, including proteins, such as those associated with CRISPR; hydrophobic molecules, such as those associated with chemotherapeutics; and nucleic acids, as would be required for RNAi and gene therapy. However, the capacity to transport molecular species into cells is not limited to these molecular groups.

As described herein and above, a single quant 10 can be manufactured to contain a variety of different internal component molecules 14. Likewise, a plurality of such quants 10 may be manufactured wherein the plurality of quants 10 are suspended in an aqueous solution. Typically, quants 10 are produced in quantity and concentration adequate to support human scale therapeutics. In some embodiments, millions or billions of quants 10 are suspended in a volume of aqueous solution for delivery to a patient. For example, the suspended quants 10 may be provided in a drip bag for intravenous delivery. When manufactured to the same specification, the plurality of quants 10 are uniform in size, uniform in chemical composition, and therefore uniform in functionality. Functional uniformity is an essential aspect of quants 10, manifested in design and production. Functional uniformity can typically be described as at least a pair of items that are similar to the extent that they are swappable without an expected change in function, e.g., a mass-produced item, such as a collection of bolts made to the same specification. Uniformity among a collection of alike quants 10 requires that the same number of each molecular species is present in each quant 10 and should typically vary by less than a population coefficient of standard deviation (% CV) of 10%, and more preferably, less than 5%. Likewise, proportions of each molecular species comprising the particle should vary by less than a population coefficient of standard deviation (% CV) of 10%, and more preferably, less than 5%. This provides a unique aspect of predictability which allows for more precise dosing which will be described in detail in later sections.

It may be appreciated that although quants 10 manufactured to the same specification are alike and uniform, quants 10 produced to different specifications may be combined to create a heterogenous mixture of quants 10. For example, a first batch of 1 billion quants 10 may be manufactured wherein each of the quants 10 are of uniform size and contain three (A, B, C) component molecules 14. Likewise, a second batch of 1 billion quants 10 may be manufactured wherein each of the quants 10 has a slightly larger uniform size than those of the first batch, and wherein each quant contains four (D, E, F, G) component molecules. The first and second batches may then be combined to form 2 billion quarts of quants 10, each quant 10 having either three or four component molecules. This allows for innumerable combinations of quants 10, wherein each of the combinations is highly controllable, leading to highly controllable functionality.

It may be appreciated that quants 10 are stable in solution during storage and delivery. It may be desired to create quants 10 with a net charge. Quants 10 can be delivered with a net positive, negative, or neutral charge by virtue of the charges of their molecular composition. For example, the interface molecules 12 may be be selected with a more or less negative charge, and likewise the component molecules 14 can be selected or modified to achieve a more or less negative charge. Each molecule comprising the quant has certain charge characteristics, and the net charge of these component molecules 14 determines the net charge of the quant 10. Thus, the charge can be modified by modifying its constituent molecules.

Thus, it may be appreciated that in some embodiments quants 10 are considered separate molecular assemblies stably dispersed in an aqueous solution, wherein each molecular assembly is functionally uniform, capable of uptake by a targeted cell, comprised of one or more (such as at least 3) molecular species, measures between 20 and 200 nanometers in mean diameter with a population coefficient of standard deviation of less than 20%, and is substantially uniform in terms of molecular composition such that the proportions of each constituent molecule comprising the particle varies particle-to-particle by a population coefficient of standard deviation of less than 20%.

Overview of Quant Manufacturing Process

As mentioned previously, quants 10 function independently. However, quants 10 typically do not function in isolation. Quants 10 are often present in large numbers of functionally identical quants 10 working in parallel or amongst additional quants that are functionally different but compatible or coordinated for an overall therapy. In either case, quants 10 are produced and provided in large numbers and in concentrations adequate to support human scale therapeutics. Thus, in addition to extreme uniformity, quants are also produced in high numbers and in concentrations exceeding 1 million per milliliter.

Figure 2:
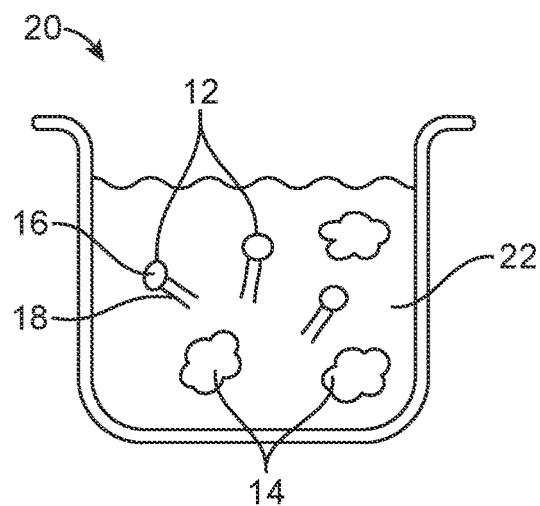
FIG. 2 illustrates a example reagent solution, wherein the reagent solution is comprised of a plurality of interface molecules, a plurality of component molecules, and a solvent system.
Figure 3:
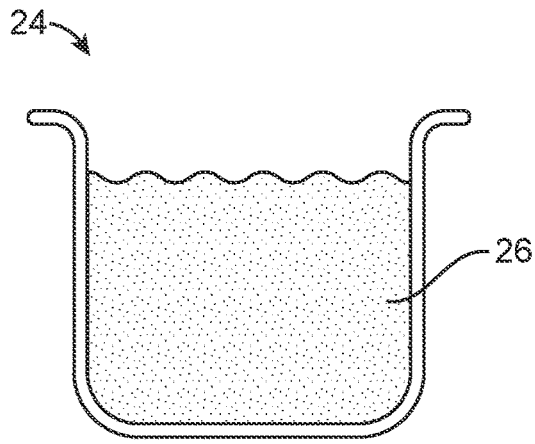
FIG. 3 illustrates a separate aqueous solution that is hydrophilic and compatible with the body.

FIGS. 2-6 illustrate an overview of an embodiment of the manufacturing process of a quant 10. Referring to FIG. 2 a reagent solution 20 is generated, wherein the reagent solution 20 is comprised of a plurality of interface molecules 12, a plurality of component molecules 14, and a solvent system 22. Typically the solvent system 22 comprises a fluid solvent (e.g., hexane) or a mixture of fluids (e.g., 50% hexane and 50% dichloromethane). As illustrated, each interface molecule 12 has a hydrophobic head 16 and a hydrophilic tail 18. In this embodiment, the plurality of component molecules 14 are uniform and hydrophobic, however it may be appreciated that the molecules 14 may be dissimilar and/or hydrophilic. It is the reagent solution 20 that creates the fluid partitions that ultimately form the quants 10. Therefore, it is crucial that the reagent solution 20 is prepared such that, when divided into millions or billions of uniform partitions, the correct concentration of each molecular species (component molecules 14 and interface molecules 12) for each quant 10 will be present in each partition. FIG. 3 illustrates a separate aqueous solution 24 that is hydrophilic and compatible with the body, such as aqueous buffer, saline, solutions with various acids or detergents, etc.). The aqueous solution 24 will ultimately carry the quants 10 into the body. In this embodiment, the aqueous solution 24 comprises aqueous buffer 26.

Figure 4:
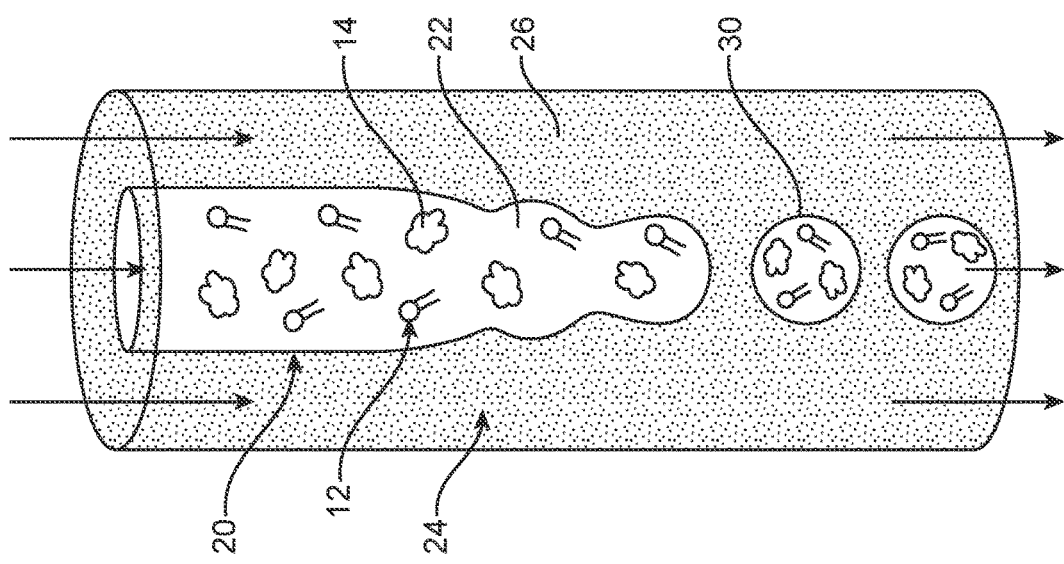
FIG. 4 is a schematic illustration of coaxial flow of the reagent solution and aqueous solution within a Microfluidic Partitioning System (MPS).

Referring to FIG. 4, the reagent solution 20 and aqueous solution 24 are input into a Microfluidic Partitioning System (MPS, described in more detail below) so that the fluids flow coaxially. FIG. 4 is a schematic illustration of the coaxial flow. As illustrated, the reagent solution 20 flows coaxially through a column or sheath of aqueous solution 24 flowing in the same direction (as indicated by arrows). Thus, the reagent solution 20 forms a central laminar flow that is surrounded by a flow of aqueous solution 24. During this process, the two fluids move together in the same direction and the inner flow of reagent solution 20 is divided into uniform partitions or droplets 30 while still in laminar flow. Each droplet 30, being formed at a rate of, for example, 1 million per second (1 MHz), contains the molecular mixture that will ultimately form a single quant 10. In some embodiments, the droplets are formed at a rate of at least 100 kHz. In other embodiments, the droplets are formed at a rate of 100 kHz to 10 MHz.

Figure 5:
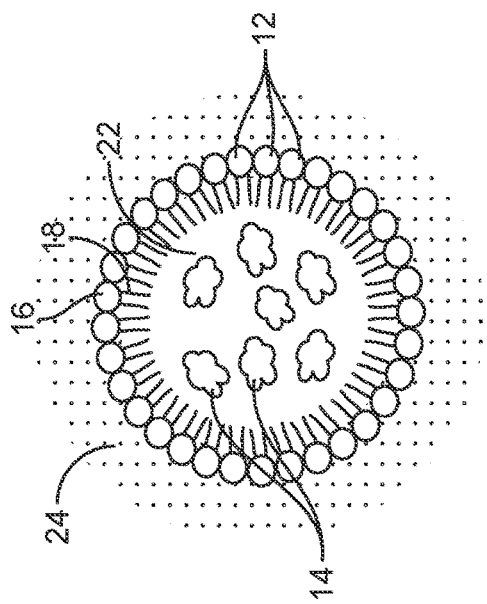
FIG. 5 illustrates the molecules of the droplet self-arranging wherein the hydrophilic heads of the interface molecules seek the aqueous solution and the hydrophobic tails face inwardly.
Figure 6:
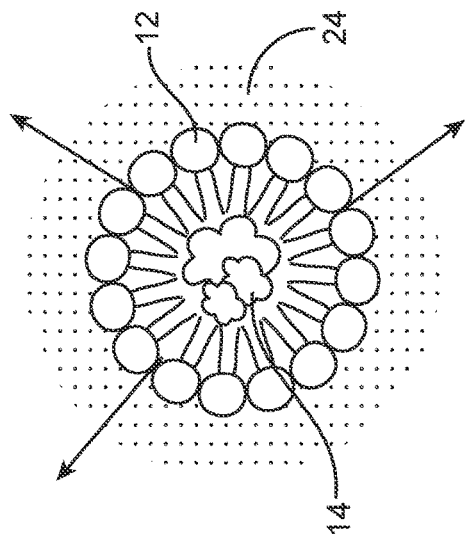
FIG. 6 illustrates the solvent system removed from the droplet.

Referring to FIG. 5, the molecules of the droplet 30 self-arrange. The hydrophilic heads 16 of the interface molecules 12 seek the aqueous solution 24 and the hydrophobic tails 18 face inwardly. This forms a sphere shape, a shape which naturally reduces the surface area to volume ratio. The component molecules 14 are now encapsulated in the droplet 30 by the interface molecules 12, appearing hydrophilic from the outside. Although small amounts of the solvent system 22 may remain in the droplet 30, the solvent system 22 is typically removed from the droplet 30, as illustrated in FIG. 6. As shown, this can be accomplished by leaching the solvent system 22 into the surrounding aqueous solution 24. This shrinks the size of the droplet 30 down and it is essentially a solid. When all of the solvent 22 has been leached out into the surrounding aqueous solution 24, or when the concentration of solvent 22 remaining in the droplet 30 is in equilibrium with the surrounding solution 24, then the quants 10 are said to have formed and can be delivered to the body via the aqueous solution 24. Further processing is possible, however, depending on the chemistries and applications chosen, particularly the solvent system 22, the quant-bearing solution 24 may be ready for delivery. For example, the resultant multicomponent drug particles and aqueous fluid can be collected for later use as an injectable drug particle suspension or delivered directly to a patient for a therapeutic purpose.

Figures 7A, 7B:
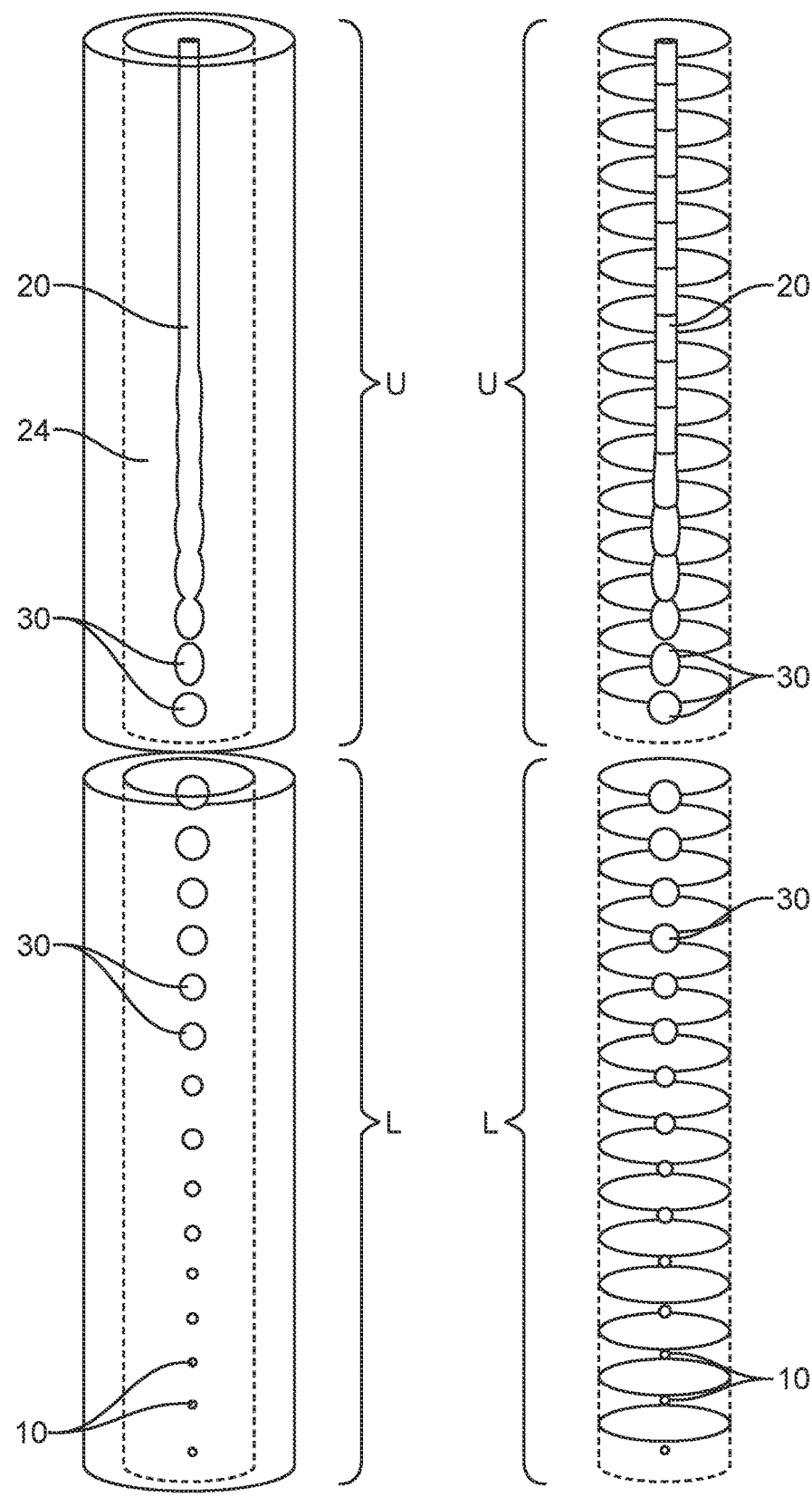
FIGS. 7A-7B schematically illustrate an embodiment of the stages of droplet generation.

FIGS. 7A-7B schematically illustrate an embodiment of the stages of droplet 30 generation. The same fluid flow, moving from top to bottom, is shown twice, in parallel, to illustrate the relationship between droplet production in terms of flow and timing. FIG. 7A shows continuous flow; FIG. 7B shows the same flow divided into segments corresponding with uniform segments of time, and with cylindrical sections of both fluids in coaxial flow. In the upper segment U of both FIGS. 7A-7B, a coaxial flow of reagent fluid 20 breaks into droplets 30 over time and distance travelled. In the lower segment L of both FIGS. 7A-7B, droplet volumes are reduced over time and distance travelled. In the upper segment U of FIG. 7A, reagent fluid 20 flows first as an unbroken coaxial flow, before breaking into uniform droplets 30. In the lower segment L of FIG. 7A, uniform droplets 30, are reduced in volume to form uniform particles or quants 10. In the upper segment U of FIG. 7B, the reagent fluid 20 is illustrated as flowing as an unbroken coaxial flow, before breaking into uniform droplets 30. In the lower segment L of FIG. 7B, uniform droplets 30 are reduced in volume to form uniform particles or quants 10. FIG. 7B illustrates the same fluid flow as in FIG. 7A but divided into cylindrical segments that depict the relative fluid position along the length of the flow path and the conformation and special relationship of those two fluids as they travel the length of the fluid column. The upper segment U of FIGS. 7A-7B illustrate the flow that takes place in a laminar flow condition, and where the two fluids change conformation, but not volume. The lower segment L of FIGS. 7A-7B depict a size reduction process that may take place in a non-laminar flow condition, and in this area only the size of the droplet is shown while the solvent molecules radiating from that droplet and into the surrounding fluid and accumulating therein is not shown.

Figure 8A:
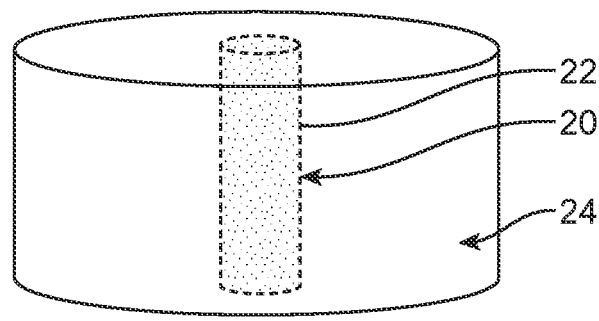
FIGS. 8A-8D schematically illustrate four key stages of quant generation.
Figure 8B:
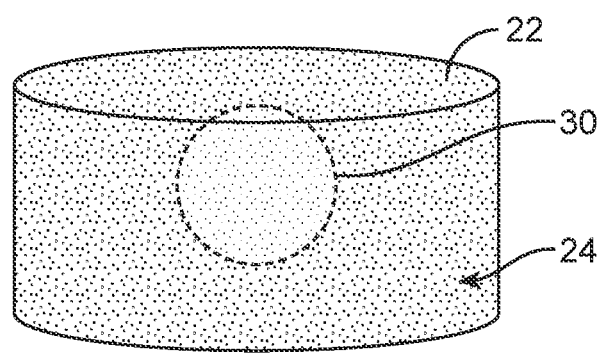
Figure 8C:
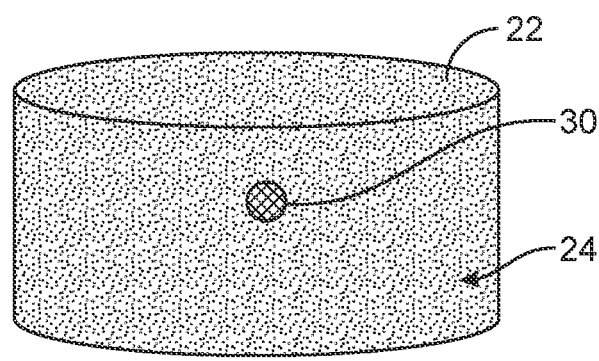
Figure 8D:
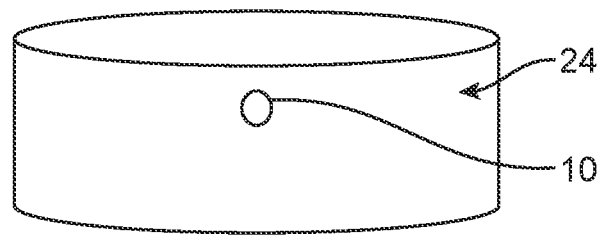

FIGS. 8A-8D schematically illustrate four key stages of quant 10 generation. Here, the solvent system 22 is shown as black and relative concentrations of solvent system 22 are darker and lighter. Referring to FIG. 8A, a cylindrical section of first fluid flow (e.g. reagent fluid 20) is illustrated and shown in black since it is comprised of solvent system 22. The cylindrical section of reagent fluid 20 is surrounded in coaxial flow by a second fluid (e.g. aqueous solution 24). FIG. 8B illustrates the next key stage wherein the first fluid droplet 30 has formed surrounded by a cylindrical section of flow. Here, a small amount of solvent system 22 has eluted into the surrounding flow. FIG. 8C illustrates the next key stage wherein the droplet 30 is shrinking toward a fluid particle or quant due to further elution of the solvent system 22 into the cylindrical section of flow (e.g. aqueous solution 24). FIG. 8D illustrates the final quant 10 surrounded by a cylindrical section of coaxial flow that has been stripped of solvent, reducing the total overall volume of the cylindrical fluid segment.

Figure 9:
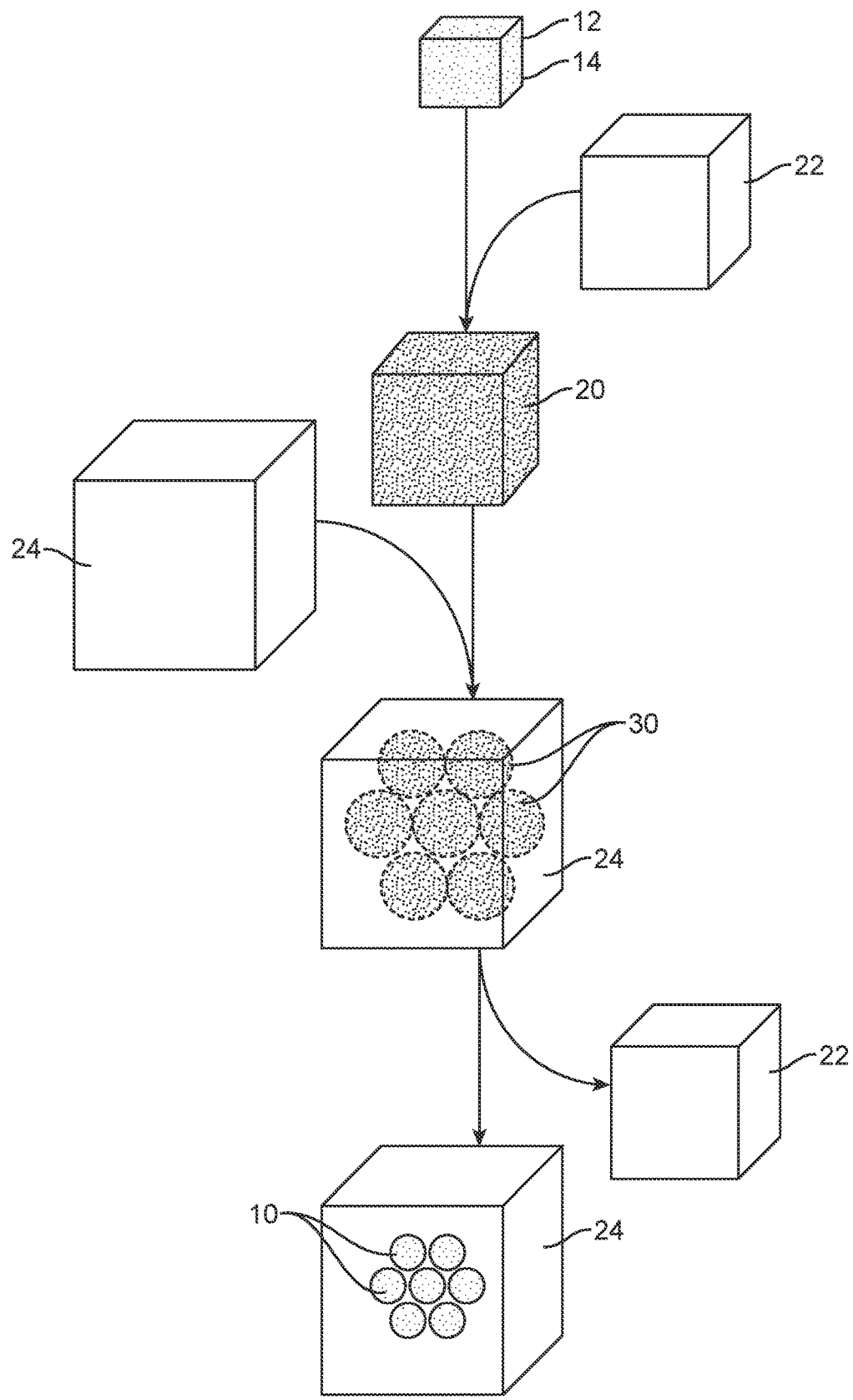
FIG. 9 schematically illustrates an embodiment of an overall production process showing the input materials from a volumetric standpoint.

FIG. 9 schematically illustrates an embodiment of an overall production process showing the input materials from a volumetric standpoint. Fluids are thus represented as cubic forms that are not to scale, but only suggest relative relationships between the reagents. In this embodiment, the volume of a molecular mix comprising the molecular components (e.g. interface molecules 12 and component molecules 14) is mixed with another, larger volume of fluid (e.g. a solvent system 22) to form a third volume of fluid (e.g. reagent solution 20). Another volume of fluid (e.g. an aqueous solution 24 or saline solution), is combined with the solvent and molecular mix (e.g. reagent solution 20) to form another volume of fluid. The process of combination (not shown here), provides that a coaxial flow is divided into a collection of uniform droplets 30 of solvent and molecular mix in aqueous solution 24. A separation process (not shown) causes the removal of solvent system 22 from the droplets 30 to form a final volume of aqueous solution 24 and particles or quants 10 comprised of molecular mix.

Figure 10A:
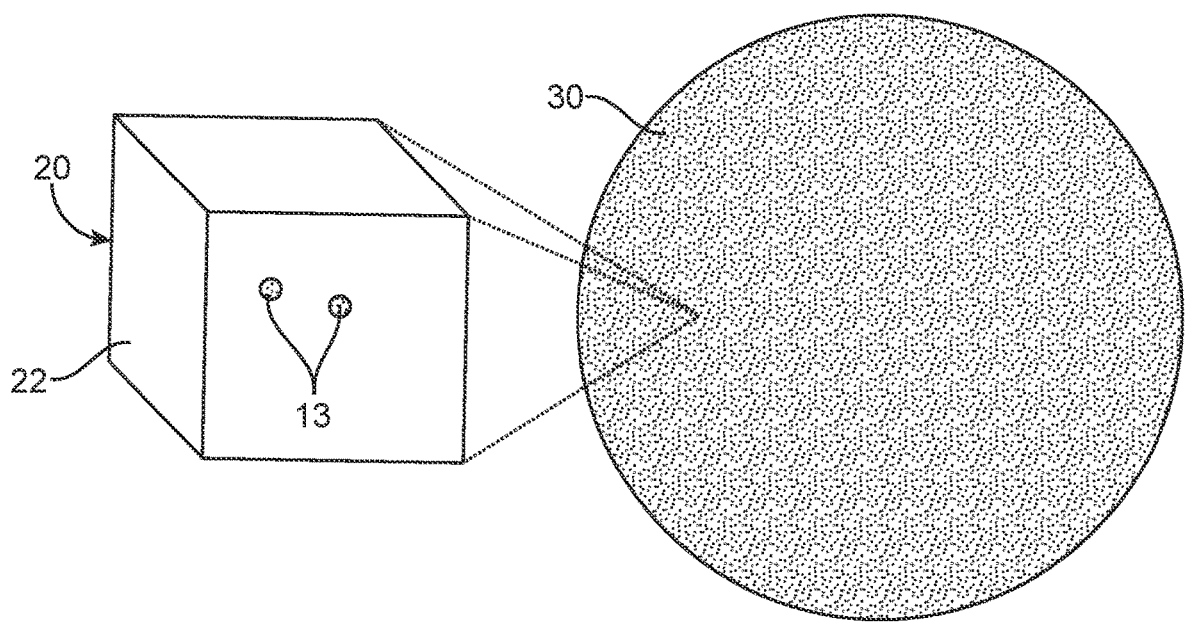
FIGS. 10A-10C illustrate the relative compositions of droplets to quants during the concentration process of nanoparticle manufacture in a single molecular species example
Figure 10B:
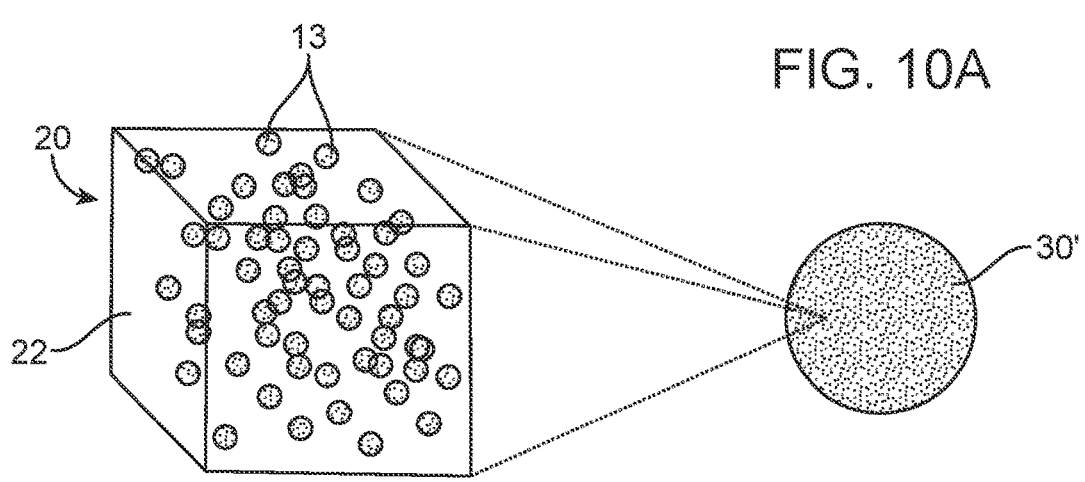
Figure 10C:
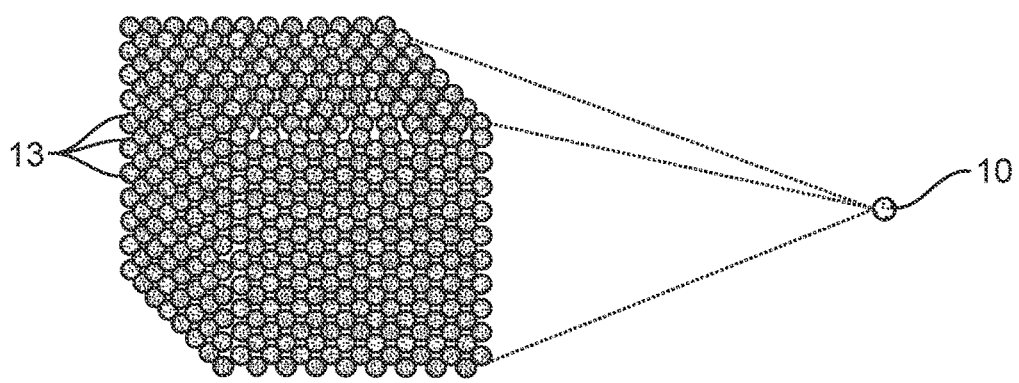

FIGS. 10A-10C illustrate the relative compositions of droplets 30 to quants 10 during the concentration process of nanoparticle manufacture in a single molecular species example. In this embodiment, a droplet 30 of a hydrophobic molecular mix (e.g. reagent solution 20) and solvent system 22 is shown (FIG. 10A) immediately after the production process. The large droplet 30 is comprised of solvent system 22 containing dissolved molecules 13 of the reagent solution 20. During the concentration process, the larger droplet 30 is reduced to an intermediate, smaller droplet 30' illustrated in FIG. 10B. The same number of dissolved molecules 13 remain in the smaller droplet 30' even as the smaller droplet 30' loses solvent 22 to its surroundings. A closer view of the smaller droplet 30' shows a higher concentration of molecules distributed throughout. The final stage of droplet concentration, FIG. 10C, occurs when the solvent 22 has left the droplet entirely, yielding a particle or quant 10 without solvent. A closer view of the quant surface and interior shows that it is a solid particle.

Figure 11A:
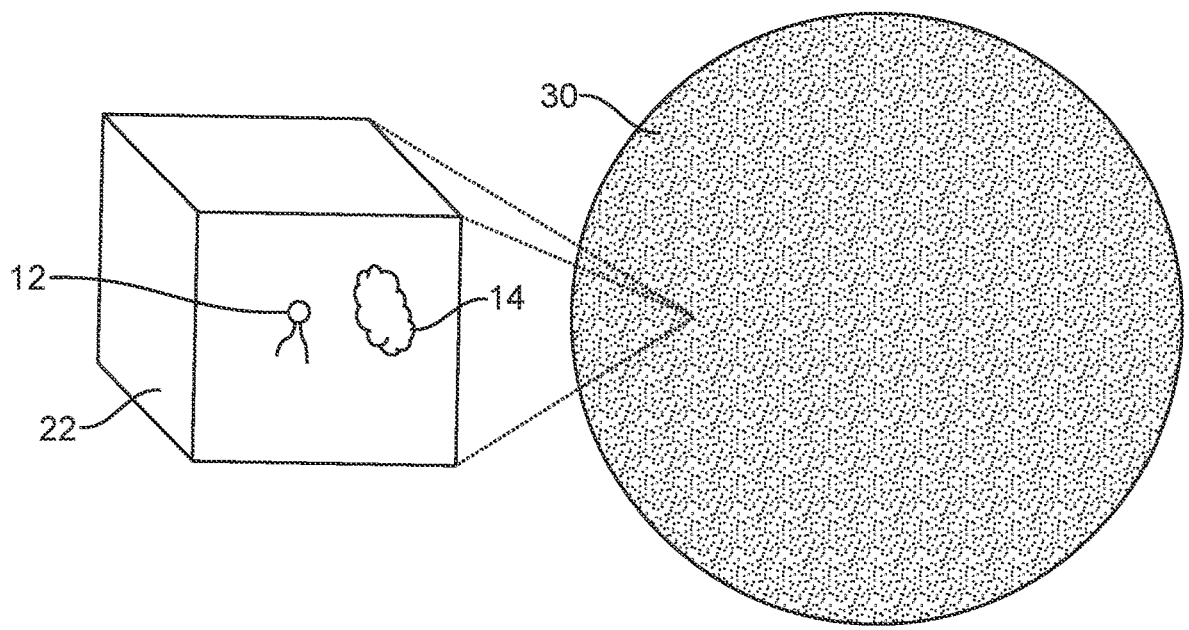
FIGS. 11A-11C illustrate the relative compositions of partitions or droplets during the concentration process of nanoparticle manufacture similar to FIGS. 10A-10C, but wherein two molecular species are shown.
Figure 11B:
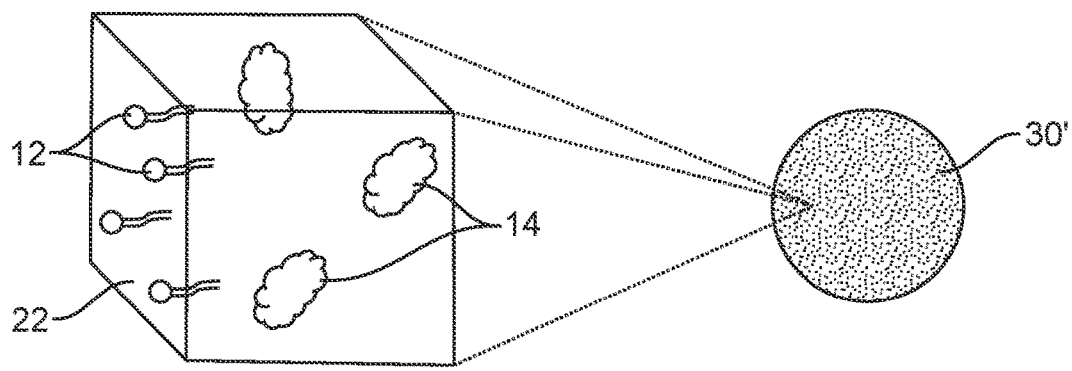
Figure 11C:
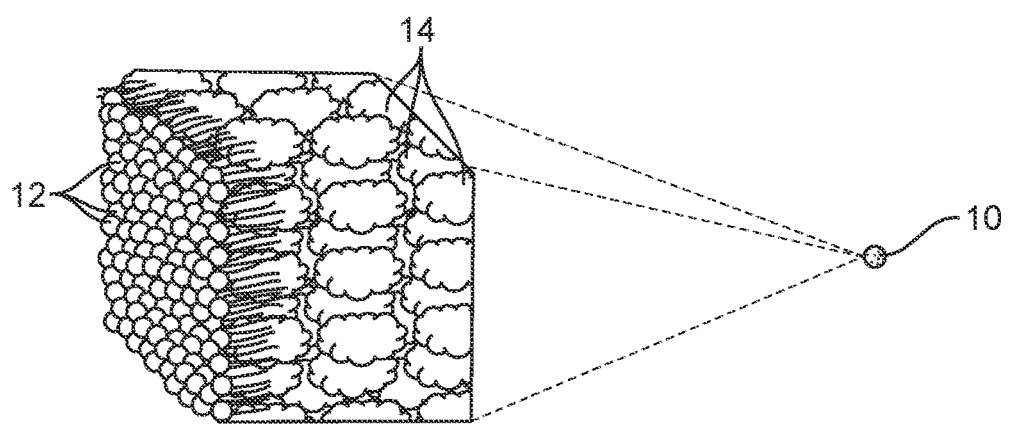

FIGS. 11A-11C illustrate the relative compositions of partitions or droplets 30 during the concentration process of nanoparticle manufacture similar to FIGS. 10A-10C, but wherein two molecular species are shown. This embodiment, a large droplet 30 is shown immediately after the production process with a small section of the surface and interior shown in detail to contain a mixture of hydrophobic component molecules 14 and amphiphilic interface molecules 12 mixed in a solvent system 22. That same droplet 30, over time, is reduced in volume as the solvent 22 escapes into the surrounding aqueous solution. A closer look at the smaller droplet 30', illustrated in FIG. 11B, shows that the concentration of molecules 12, 14 is increased relative to the solvent 22, and that some of the amphiphilic interface molecules 12 have arranged themselves on the outer surface of the smaller droplet 30'. The end result of this concentration process, illustrated in FIG. 11C, is a solid particle or quant 10 containing the same molecules 12, 14 as in earlier stages, but now as a particle comprised of molecular mix without solvent 22, as seen in a closer look at the surface and interior.

Thus, the nanodrug particles or quants 10 start out as microscale solvent droplets in an emulsion where the continuous fluid is aqueous. The solutes in either or both fluids may be comprised of any combination of molecular species in a specific proportion. As the solvent moves from the solvent droplets into the aqueous fluid in a process similar to evaporation, the solutes within each droplet are drawn closer together, and eventually collapse into each other to form particles. Those particles may be comprised of any number of chemical species, including lipids, and the ratios are important because the predetermined mixture is responsible for the assembly taking a particular configuration; the final configuration of the molecules in each quant reflects the lowest energy state of the molecules involved. The very size and function of each particle is based on this initial mixture, although the exterior may also contain some water-soluble molecules contributed from the aqueous fluid. The solvent: aqueous ratio is also important, since the solvent needs to be adsorbed into the continuous fluid in order for the particles to form.

Overview of Microfluidic Partitioning System

Figure 12:
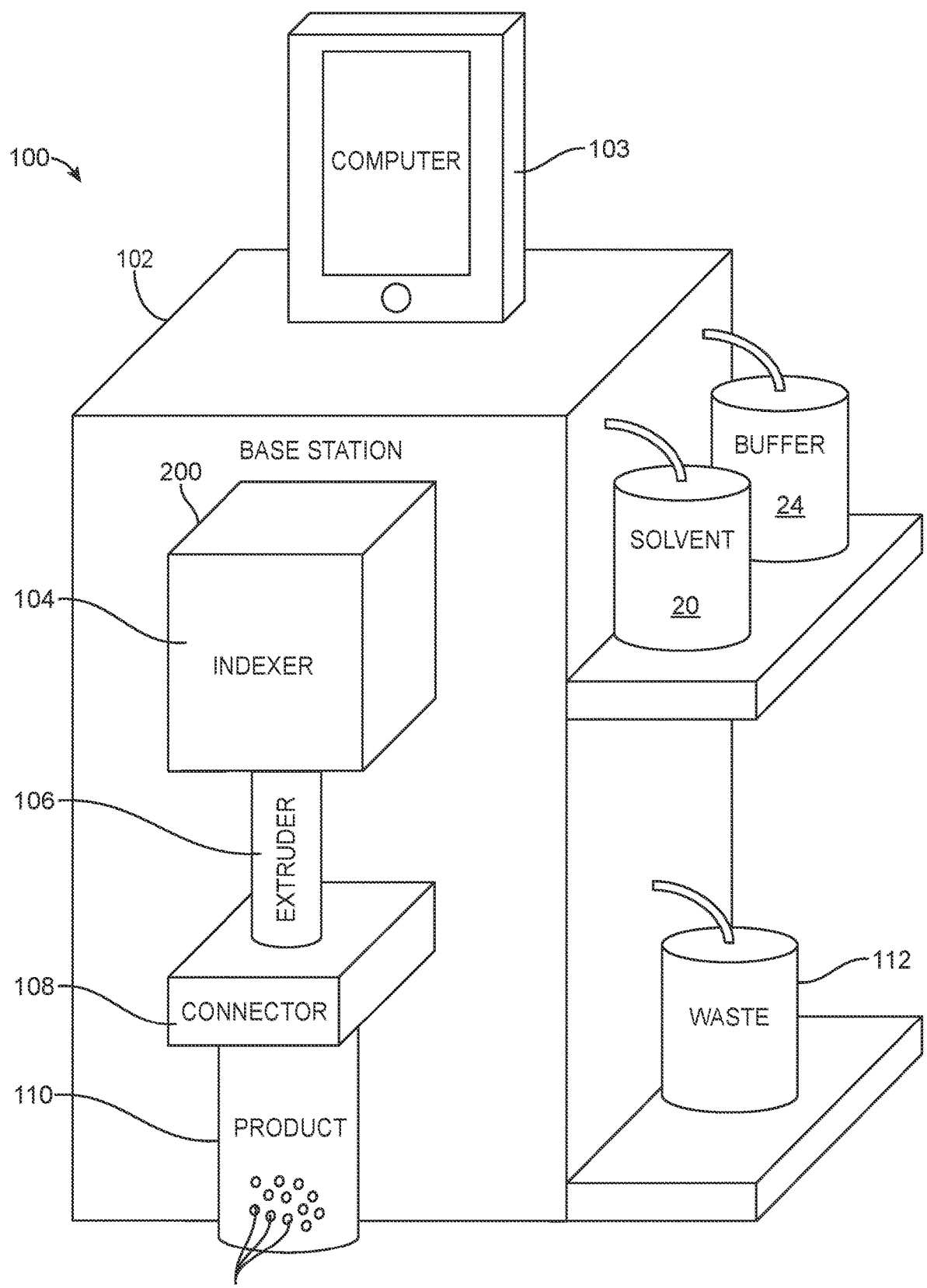
FIG. 12 illustrates the visible and accessible components of one embodiment of a microfluidic partitioning system.

FIG. 12 illustrates the visible and accessible components of one embodiment of a microfluidic partitioning system 100. The system 100 is utilized to form the quants 10 described hereinabove. In this embodiment, the system 100 includes a base station superstructure 102. The base station superstructure 102 includes a variety of internal components that will be described in later sections.

The superstructure 102 also includes a computer control unit 103 which monitors and controls key aspects of the partitioning process. The superstructure 102 includes inflow for the first solution (e.g. hydrophobic reagent solution 20) and inflow for the second solution (e.g. buffered aqueous solution 24). In this embodiment, the superstructure 102 also includes an indexer 104 mounted thereon. The indexer 104 is the location where the solutions 20, 24 come together for coaxial flow. An extruder 106 is connected to the indexer 104 as shown. Typically, the extruder 106 removable and disposable. In such instances, the extruder 106 is attachable such as with a reversible interlocking seal (not shown). The extruder 106 receives the coaxial flow of solutions 20, 24 in at least one microfluidic channel and forms the droplets. The extruder 106 is connected to a connector 108 which provides a fluidic connection between the distal end of the extruder 106 and a product container 110. Excess solution (e.g. solvent 22, aqueous solution 24, etc) is removed from the indexer 104 and/or connector 108 and diverted to a waste container 112. The product container 110 captures the quants 10 and any fluid output (e.g. aqueous solution 24) from the extruder 106.

Some conventional applications of microfluidic technology employ coaxial flow, where an inner core fluid flows within an outer core fluid. Microfluidic coaxial flow is a generally unstable physical arrangement of fluids and can be a first step in the production of droplets. However, initiating and sustaining a microfluidic coaxial flow is difficult to achieve using standard microfluidic components, particularly in regimens requiring very high pressures. Likewise, alternative systems, including microfluidic chips, tube-type droplet generators, and planar type droplet generators, are prone to clogging, require more complicated interfacing, cannot handle high pressures, or are less suitable for disposables. The microfluidic partitioning system 100 overcomes these deficiencies.

Figure 13:
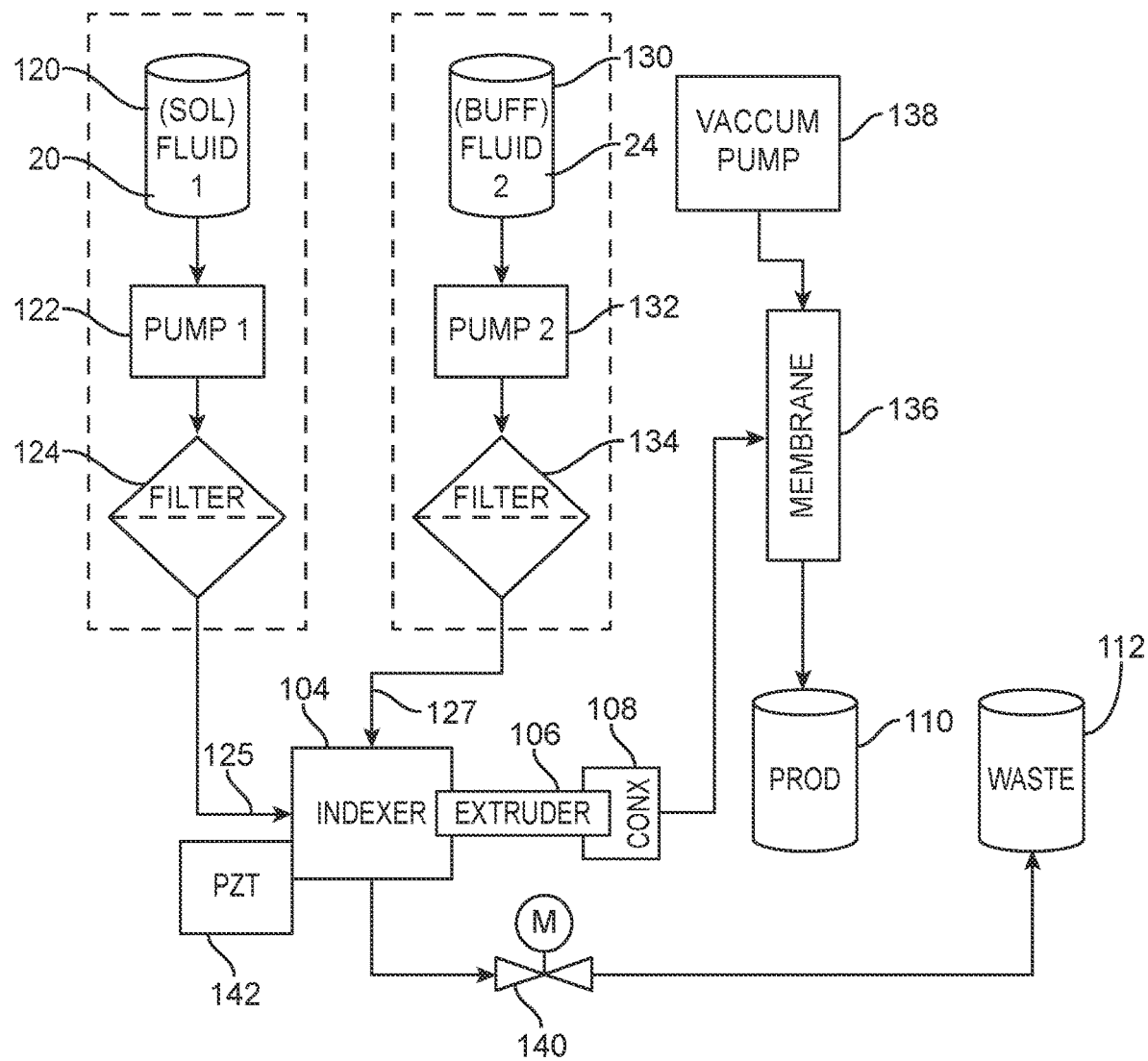
FIG. 13 is a schematic illustration of the fluid pathways of an embodiment of the microfluidic partitioning system of FIG. 12.

FIG. 13 is a schematic illustration of the fluid pathways of an embodiment of the microfluidic partitioning system 100 of FIG. 12. Here, the first solution (e.g. hydrophobic reagent solution 20) is contained in a first fluid reservoir 120 in fluid communication with a first pump 122 and a first filter 124 which is in fluid communication with a first fluid inlet 125 of the indexer 104. A second solution (e.g. buffered aqueous solution 24) is contained in a second fluid reservoir 130 in fluid communication with a second pump 132 and the second filter 134 which is in fluid communication with a second fluid inlet 127 of the indexer 104. The extruder 106 is connected with the indexer 104 and receives the first and second solutions. Typically, fluid flowing from the extruder 106 is in fluid communication with a membrane unit 136 via the connector 108. In some embodiments a vacuum pump 138 provides the extractive force to the membrane unit 136, which is in fluid communication with the product container 110. In this embodiment, a waste container 112 is connected to a waste gate on the indexer 104 via a motorized valve 140. In addition, in this embodiment, a piezo element 142 is shown attached to the indexer 104. The piezo element 142 is used to assist in controlling droplet formation as will be described in later sections.

Figure 14:
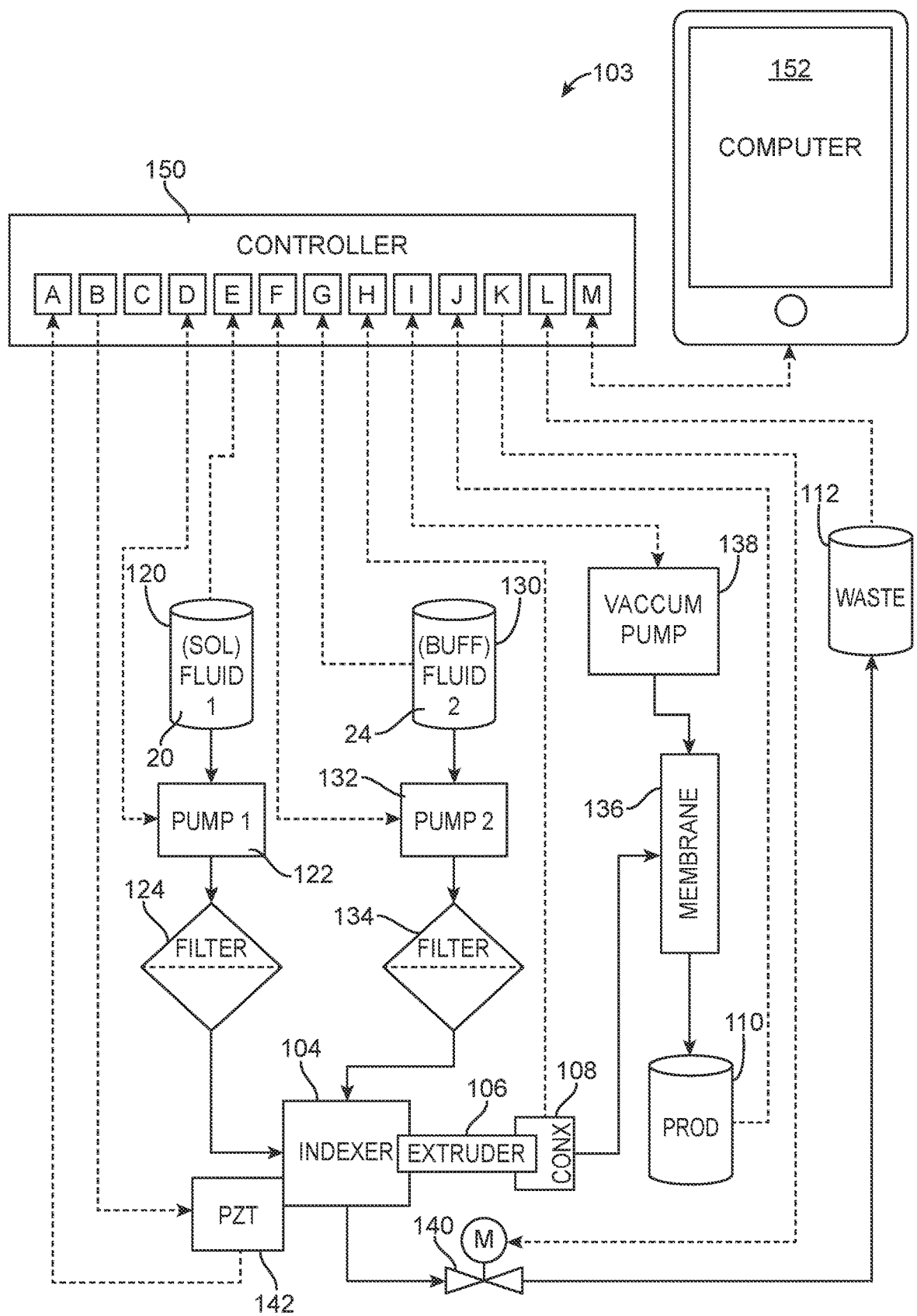
FIG. 14 is a schematic diagram of the fluid pathways of FIG. 13 with the inclusion of conductive pathways shown as dashed lines.

FIG. 14 is a schematic diagram of the fluid pathways of FIG. 13 with the inclusion of conductive pathways shown as dashed lines. In this embodiment, the addition of a computer control unit 103, comprising a controller terminal bus 150 and a computer 152, allow for a flow of data to monitor and control key aspects of the partitioning process. Solid lines represent fluidic connections; dashed lines represent conductive pathways used for digital and analog signals. Each connection is shown along a controller terminal bus 150. Connection A links a piezo actuator 142 feedback signal to the controller terminal bus 150. Connection B links a piezo actuator 142 to a signal source. Connection C is open. Connection D links two-way traffic between a first fluid pump 122 to the controller terminal bus 150. Connection E links a level sensor for the first fluid reservoir 120 to the controller terminal bus 150. Connection F links two-way traffic between a second fluid pump 132 to the controller terminal bus 150. Connection G links a level sensor for the second fluid reservoir 130 to the controller terminal bus 150. Connection H links a voltage and current supply to the distal end of the extruder 106. Connection I links a vacuum pump to the controller terminal bus 150. Connection J links the level sensor of a product container 110, or capture reservoir, to the controller terminal bus 150. Connection K links a motorized valve 140 to the controller terminal bus 150. Connection L links the level sensor of a waste container 112 to the controller. Terminal bus 150 Connection M links the controller terminal bus 150 to the computer 152.

In some embodiments, the microfluidic partitioning system 100 is a desktop-sized system with an interchangeable and disposable extruder, a real-time control system, and an intuitive user interface. Such a system 100 allows positioning near a patient wherein quants 10 can be produced and directly delivered to a patient, bypassing collection in a reservoir such a bottle, a vial, a syringe or an IV drip bag. The system 100 provides the repeatability and standardization necessary to build multicomponent drug particles to specification that can be utilized immediately in real time.

A. Pumps

With few exceptions, existing commercial microfluidic systems have evolved to meet the needs of basic sample preparation and complex assays. Perhaps for this reason, microfluidic development has remained focused on chips with attached reservoirs. Chips offer a broadly 2D format, which lends itself to various the colocation of optical and electronic interrogation techniques, as well as multichannel flowpaths. However, the potential for microfluidic systems as a means for nanodrug manufacturing suggest modular components and semi-continuous operation at much higher pressures than existing systems can support. Achieving such high pressures and sustained low-volume fluid flows is challenging.

In many embodiments, the microfluidic partitioning system 100 is designed to operate at high internal pressures, generating low-volume fluid flow but with high velocity fluid flow rates. High pressures are needed to drive fluids through smaller diameter orifices that are required to achieve the droplet production rate. In some embodiments, pressure within the indexer 104 is at least 100 psi (~689 kPa), or preferably 1000 psi (~6,890 kPa), or even more preferably, more than 10,000 psi (~68,900 kPa).

Various mechanisms of delivering fluids are known to the art and are commercially available. For example, positive displacement pumps can deliver fluids at a high pressure and at regular volumetric flow rates. Compressed gases, such as Helium, are also useful for the regular delivery of fluid. However, the very high pressures and positive digital control of flow rates generally mean that positive displacement pumps are preferred. Piston pumps move fluid by compressing it within a cylinder, usually powered by a stepper motor that makes small but distinct steps. These movements, even after transmitted through a gearbox, create small displacements, or pulses, of displaced fluid. Stepper motors offer the further convenience of offering digital control of volumetric fluid delivery. Piston type pumps can inject specific volumes of fluid into the coaxial flow generator over time to create a consistent coaxial flow of reagent fluids. Controlling the dimensions and linear flow rate is essential to producing dimensionally and functionally uniform quants.

Even small perturbations can introduce irregularity into the fluid flows and resultant partitions, and it is thus often desirable to use a pulse dampener between the pump and coaxial flow generator (indexer 104). Pulse dampeners are very small reservoirs with a slightly compressible structure that retain a small volume of pressurized fluid. A single pulse of fluid entering the internal volume of the dampener is accommodated by the compressible structure of the unit, and the fluid entering the coaxial flow generator (indexer 104) is thus maintained at a near constant flow rate and pressure.

High pressures and correspondingly high fluid flow rates necessitate a longer microfluidic flow channel than conventional microfluidic systems typically offer because the time required for droplet partitioning is independent of flow rate. In other words, it takes time for a perturbation in coaxial fluid flow to develop into a complete partition, and in that time the fluids will have travelled a relatively long distance (as opposed to typical microfluidic systems) from the point of coaxial flow ignition. The net result is that a longer continuous coaxial flow is required for higher flow rates, and more generally, for higher pressures. This is accommodated in the design of the extruder 106.

B. Indexer

The generation of quants 10 relies on the initiation of coaxial flow of two fluids by virtue of extrusion; specifically, by extruding two immiscible fluids perpendicular to their fluid interface. Coaxial flow is achieved by co-flowing two or more fluids along the same axis, one within the other, as core and sheath.

Extruding two fluids perpendicular to their interface to create a coaxial flow can be visualized simply by placing a straw into a jar filled with mineral oil and water. The relatively heavy water sinks to the bottom, and the oil floats on top to form a planar interface. If one open end of the straw is placed vertically and very near the fluid interface, and a vacuum applied to its opposite end, then both the water and oil are withdrawn into the straw as a coaxial flow wherein the water forms an inner core surrounded by an oil sheath. If the open jar is replaced with a sealed container, one that supplies the two fluids in the same proportion that they're flowing through the straw, then the fluid interface would remain in place, and the coaxial flow would continue indefinitely. And if the straw were attached to the jar lid, the system could be separated into two parts, and then reassembled. More than a mere analogy for operation, the straw and jar actually demonstrate the fluidic behaviors underlying this disclosure, and the means of separating the components is similar.

It is useful to consider this jar and straw analogy for basic understanding, but while the fundamental principles of operation may appear a simple and plainly illustrate a convenient means of dividing a microfluidic system into disposable (straw and lid) and non-disposable elements (jar and fluid supply), the realization of a functional microfluidic system for the high-speed production of nanoparticles is not straightforward.

The coaxial flow is initiated in the indexer 104. In some embodiments, the indexer 104 is housed in an indexer housing 200 mounted on the base station superstructure 102, as illustrated in FIG. 12. In some embodiments, it is desirable to include mounting features, such as through holes, or threaded ports, that are integrated into the indexer housing 200 as a means of attachment to a non-disposable structure, such as the base station superstructure 102. Usually, the indexer housing 200 will be mounted to some hard points because it will, in most instances, be considered a non-disposable component of an overall device and it will be connected to sources of pressurized fluids.

Figure 15A:
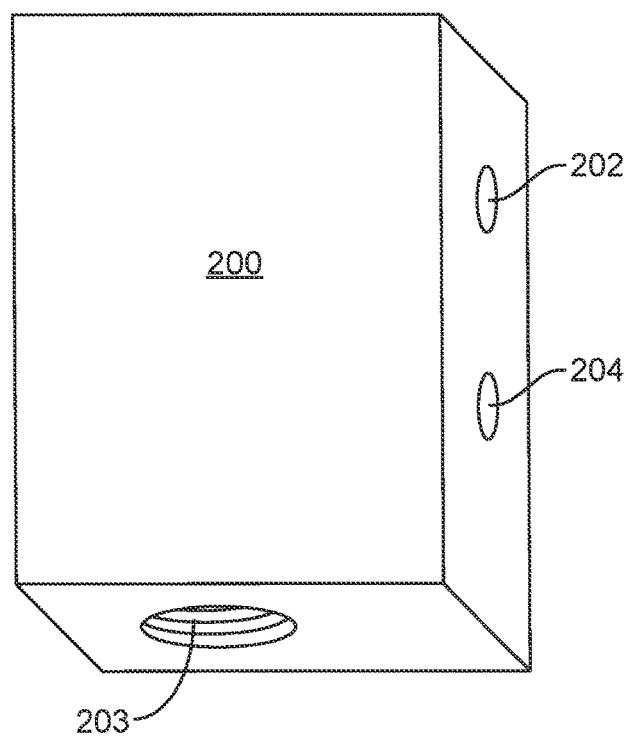
FIG. 15A provides a closer view of an embodiment of the indexer housing.
Figure 15B:
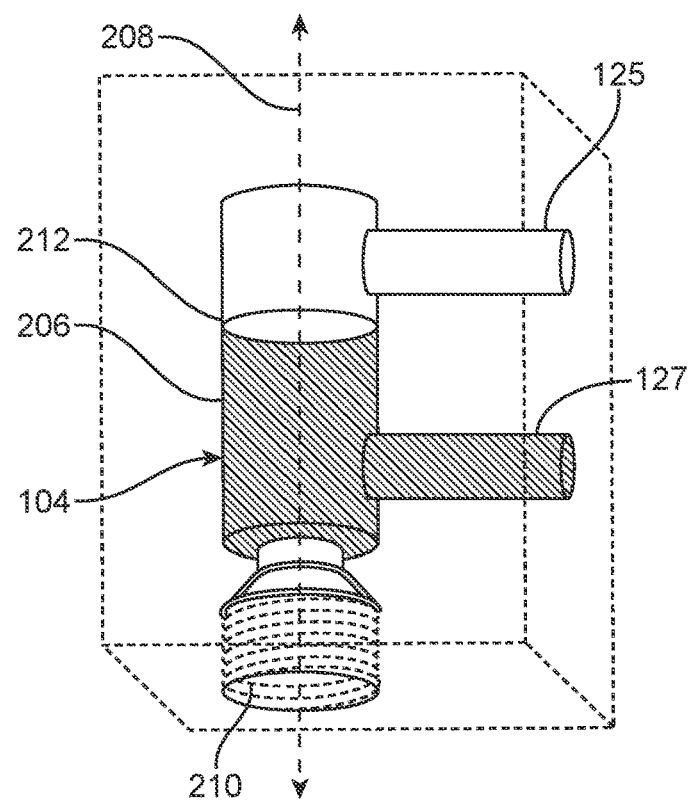
FIG. 15B illustrates an embodiment of an indexer positioned within the indexer housing.

FIG. 15A provides a closer view of an embodiment of the indexer housing 200. Likewise, FIG. 15B illustrates an embodiment of an indexer 104 positioned within the housing 200. Referring to both FIGS. 15A-15B, the housing 200 includes at least a first opening 202 to allow for passage of the first fluid inlet 125 and at least a second opening 204 to allow for passage of the second fluid inlet 127. Recall, in this embodiment, the first fluid inlet 125 passes the reagent solution 20 and the second fluid inlet 127 passes the aqueous solution 24.

The inlets 125, 127 connect with at least one indexing chamber 206. In this embodiment, the chamber 206 is comprised of a cylindrical cavity having a longitudinal axis 208 with one open end or outlet 210. The solutions 20, 24 enter the indexing chamber 206 so as to form a fluid interface 212 between the inlets 125, 127 which is perpendicular to the longitudinal axis 208. In this embodiment, the inlets 125, 127 enter the chamber 206 from the same side of the longitudinal axis 208, however it may be appreciated that the inlets 125, 127 may enter the chamber 206 from opposite sides of the longitudinal axis 208.

It may be appreciated that although the indexing chamber 206 is cylindrical in this embodiment, it is not necessary. In some embodiments, the indexing chamber 206 has a mean diameter of between 50 and 3,000 micrometers, or more preferably, between 200 and 1000 micrometers. In some embodiments, the indexing chamber 206 is comprised of one or more chemically inert material, such as stainless steel, titanium, aluminum, Polyphenelyene Sulphide (PPS), Polytetrafluoroethylene (PTFE), Polyetherether Ketone (PEEK), Polyoxymethylene (POM), Ethylene Propylene Diene (EPDM), Ethylene Tetrafluoroethylene (ETFE), Polypropylene (PP), or Chlorotrifluoroethylene (PCTFE/CTFE). Such materials are less likely to react with the reagent fluids. The materials selected will confer the desired structural, electrical, and chemical compatibilities.

It may be appreciated that the indexer 104 need not contain any microscale features or flow paths, although a narrow indexing chamber 206 allows for fluids to form a single interface because a more confined space is more likely to contain just one fluid interface whereas a larger chamber diameter would allow for a first and second fluid to rearrange themselves based on density or other factors contributing to fluid mixing. A narrow indexing chamber 206 also minimizes the potential for dead volumes and reduces the surface area of the fluid interface 212 where the fluids are in contact. This reduces the possibility that the fluid interface 212 may break down or otherwise diminish. A narrow indexing chamber 206 minimizes the area of the fluid interface 212 and therefore minimizes the time that the interface 212 is renewed with the flow of fluid.

Figure 16:
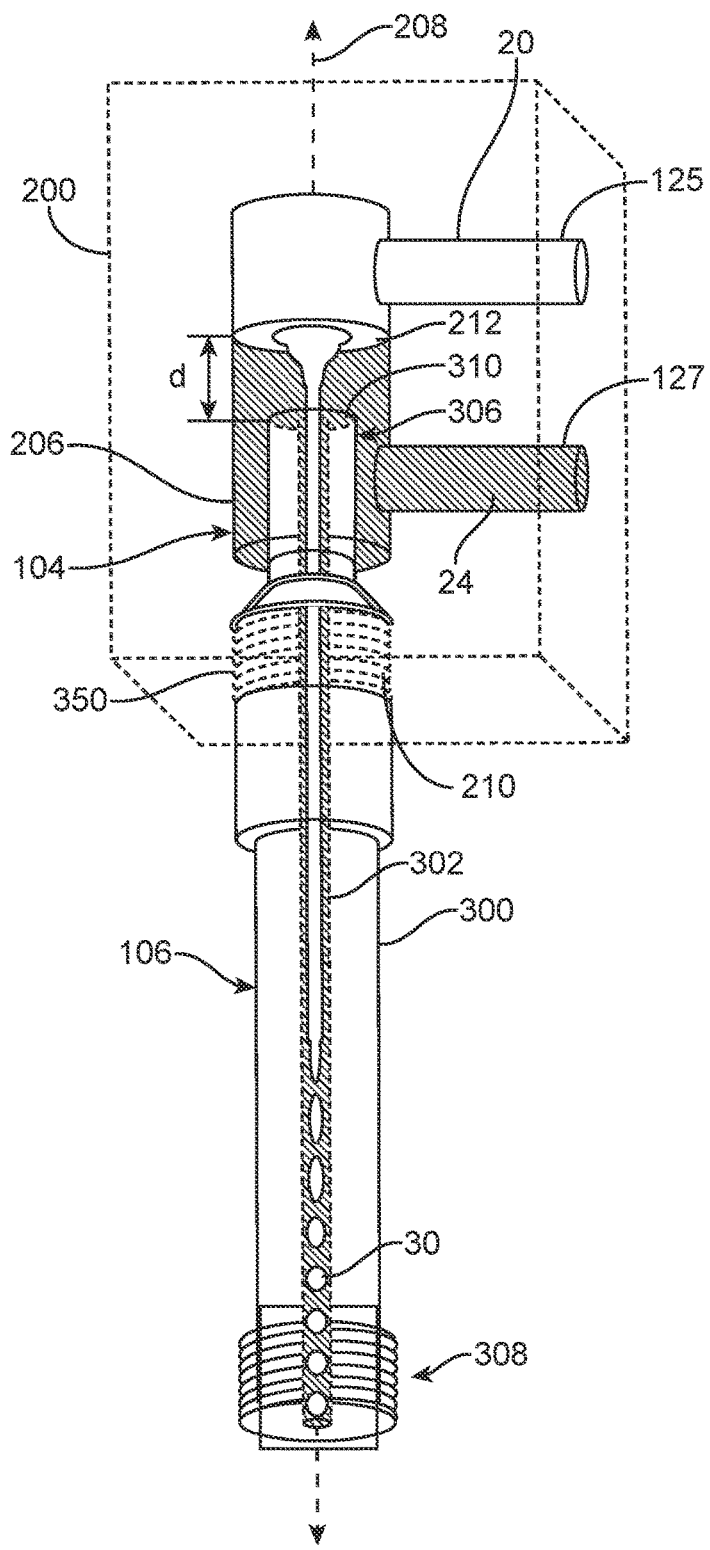
FIGS. 16-17 illustrate an embodiment of an extruder connected with the indexer (FIG. 16) and the extruder (FIG. 17) alone for clarity.
Figure 17:
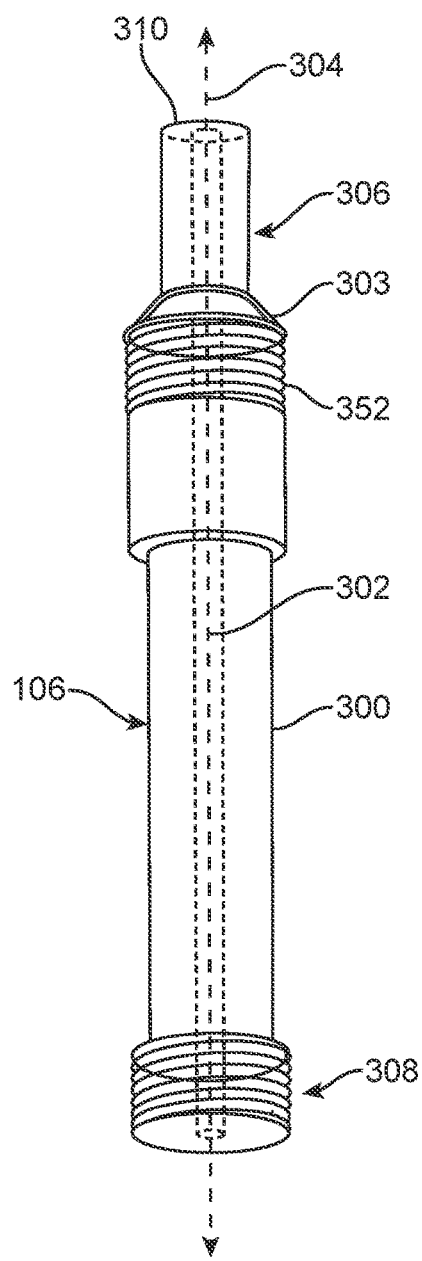

The outlet 210 of the indexing chamber 206 connects with the extruder 106. FIGS. 16-17 illustrate an embodiment of an extruder 106 connected with the indexer 104 (FIG. 16) and the extruder 106 (FIG. 17) alone for clarity. It may be appreciated that in some embodiments the extruder 106 is detachable from the indexer 104, thereby residing alone. Such detachment may be desired for cleaning purposes or to exchange the extruder 106 with one of a different size, shape, contour, material, or other difference.

In this embodiment, the extruder 106 comprises an elongate body 300 having a generally tube shape enclosing at least one microfluidic channel 302 that extends along its longitudinal axis 304. The extruder 106 has a proximal end 306 that connects with the indexer 104 to create coaxial flow, and a distal end 308 opposite the proximal end 306 for outflow. The at least one microfluidic channel 302 extends from the proximal end 306 to the distal end 308 of the extruder 106. In this embodiment, the proximal end 306 is shaped so as to be advanceable into the outlet 210 of the indexer 104, such as illustrated in FIG. 16. In particular, the proximal end 306 is shaped so as to enable coaxial flow from the indexer 104 into the at least one microfluidic channel 302 of the extruder 106 in a manner so as to generate desired droplets therein downstream. In this embodiment, the proximal end 306 has a tip 310 having a flat shape. Thus, the tip 310 is blunt, forming a flat surface that is substantially perpendicular to the longitudinal axis 304. In addition, the proximal end 306 has an outer diameter that is smaller than the inner diameter of the indexing chamber 206 to allow advancement therein. The extruder 106 is thus positioned so that its longitudinal axis 304 aligns with the longitudinal axis 208 of the indexer 104. In this embodiment, the proximal end 306 is positionable so that its tip 310 is below the fluid interface 212 and within a specified distance d of the fluid interface 212. In some embodiments, the specified distance d is up to 1 mm. The proximal end 306 of the extruder 106 is held in place, at the specified distance d, by an interlocking feature as will be described in more detail in later sections.

Thus, during operation, the indexer 104 retains the fluid interface 212 perpendicular to the longitudinal axis 208 of the indexing chamber 206, between the first and second fluid inlets 125, 127 fluidically connected thereto. The proximal end 306 of the extruder 106 is therefore located between the first and second fluid inlets 125, 127 when installed. Consequently, the first solution (e.g. hydrophobic reagent solution 20) is poised above the proximal end 306 and the second solution (e.g. buffered aqueous solution 24) fills up around the proximal end 306. As the two immiscible fluids are supplied volumetrically and in proportion at high pressures, they both flow into the proximal end 306 of the extruder 106. Their interface 212 will remain a small offset distance d from the proximal end 306 of the extruder 106 when in equilibrium, and both fluids will flow into the extruder 106 as a coaxial flow as the interface is withdrawn into the length of the extruder 106.

FIGS. 18A-18C are sectional views of an embodiment of an assembled indexer 104 and extruder 106 combination in three different states of fluid flow, demonstrating the variable position of the fluid interface 212 within the indexer 104 relative to the proximal end 306 of the extruder 106, and its effect on coaxial fluid flow. In each of the three instances (FIG. 18A, FIG. 18B, FIG. 18C), the indexing chamber 206 is in fluid communication with a first fluid via the first fluid inlet 125 and a second fluid via a second fluid inlet 127. The two fluids are immiscible. The first fluid is shown in black, and the second fluid is shown as white. The fluid interface 212 is positioned within the indexing chamber 206 between the first and second inlets 125, 127. The fluid interface 212 is perpendicular to the longitudinal axis 304 of the extruder 106. FIG. 18A illustrates fluidic action when the fluidic interface 212 is offset from the extruder proximal tip 310 so greatly that the first fluid does not flow into the extruder 106. FIG. 18B illustrates fluidic action when the fluidic interface 212 is positioned near the extruder proximal tip 310 (at a distance d) such that the first fluid and second fluids are coextruded; a coaxial flow occurs in the microfluidic channel 302 of the extruder 106, and a mixture of the first and second fluids exit the distal end of the extruder 106. FIG. 18C illustrates fluidic action when the fluidic interface 212 is positioned too close or below the extruder proximal tip 310 such that the second fluid is not extruded; a flow of the first fluid passes through the microfluidic channel 302 of the extruder 106 and exits the distal end 308 of the extruder 106. Thus, by comparing FIGS. 18A-18C, it is evident that FIG. 18B illustrates the flow condition when the system is in equilibrium and stable volumetric flow of both fluids results in coaxial flow.

FIG. 19 is a sectional view of an embodiment of an assembled indexer 104 and extruder 106 combination with three fluid ports, demonstrating the flow of three fluids to form a collection of droplets. Here, the indexing chamber 206 is in fluid communication with a first fluid inlet 125 and a second fluid inlet 127 containing a first and a second fluid, respectively, wherein the first and second fluids are immiscible. In this embodiment, the indexing chamber 206 is in fluid communication with a third inlet 129 which enters the indexing chamber 206 at the same level as the first inlet 125. The first and third fluids are miscible with each other. The first and third fluids arrange to form a fluid interface 212 with the second fluid that is extruded as it flows through the microfluidic channel 302 of the indexer 104. Such arrangement allows for the mixing of the first and third fluids immediately before being formed into a coaxial flow. This arrangement is preferred when the first and third fluids are mutually reactive or unstable when mixed. Typically, coaxial flow is extruded to create a thin, unstable filament of core as a means of droplet production as in flow focusing. However, extrusion is a process that does not require traditional microfluidic junctions; extrusion can be used to create a coaxial flow directly from a fluid interface. The mixture of the first and third fluids that forms the core of the coaxial flow breaks into droplets 30 before flowing out of the extruder distal end 308.

FIG. 20 is a sectional view of an embodiment of an assembled indexer 104 and extruder 106 combination with four fluid ports, demonstrating the flow of four fluids to form a collection of droplets. Here, an indexing chamber 206 is in fluid communication with a first fluid inlet 125 and a second fluid inlet 127 containing a first and a second fluid, respectively, wherein the first and second fluids are immiscible. As in FIG. 19, the indexing chamber 206 is in fluid communication with a third fluid inlet 129, containing a third fluid which is miscible with the first fluid but also immiscible with the second fluid. The first and third fluids arrange to form a fluid interface 212 that is extruded as it flows through the open proximal end of the microfluidic channel 302 of the indexer 104. The mixture of the first and third fluids that comprise the core of the coaxial flow breaks into droplets 30 before flowing out of the extruder distal end 308. The additional port 131, also in fluid communication with the indexing chamber 208 is connected to a waste line. A waste line allow for flushing the reagents between runs. This may be desired to remove the residual reagents either between runs to avoid cross contamination of reagents, to remove volatile or reactive materials between runs, or to rapidly replace reagents with another fluid used as a reagent or for cleaning, storage, or calibration. In some embodiments, the additional port 131 is combined with a valve as a waste gate.

C. Extruder

As described previously, particularly in relation to FIGS. 16-17, the extruder 106 is connectable to the indexer 104, to receive the coaxial flow and generate the droplets 30 which ultimately become quants 10.

Figure 21A:
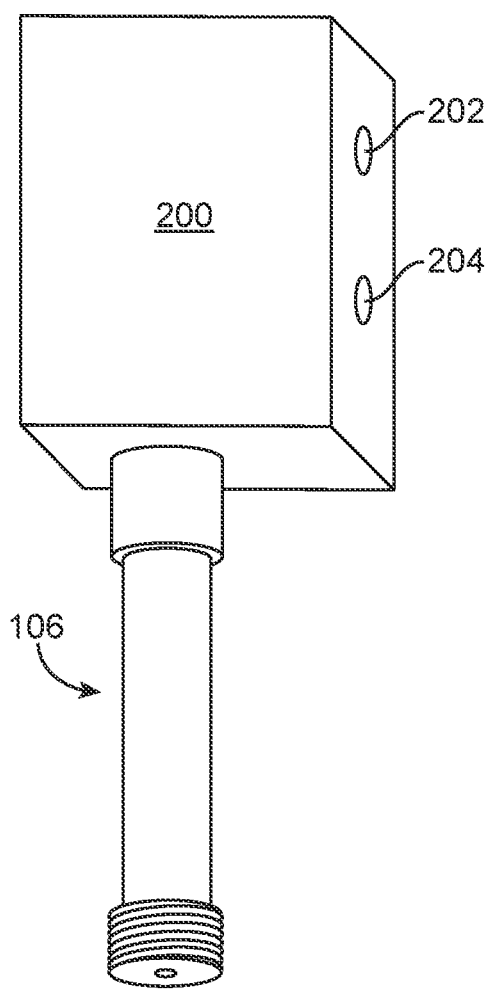
FIGS. 21A-21B provide an exterior view of an embodiment of an extruder insertable into an indexer housing.
Figure 21B:
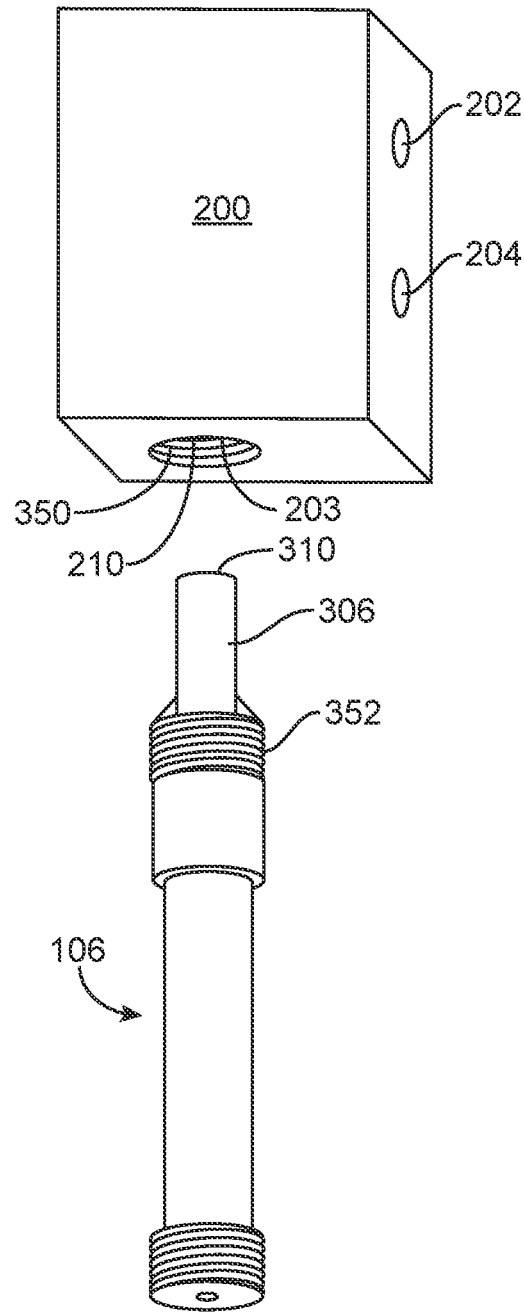

FIGS. 21A-21B provide an exterior view of an embodiment of an extruder 106 insertable into an indexer housing 200. The housing 200 includes at least a first opening 202 to allow for passage of the first fluid inlet 125 and at least a second opening 204 to allow for passage of the second fluid inlet 127. FIG. 21A illustrates the extruder 106 attached to the housing 200 and FIG. 21B illustrates the extruder detached from the housing 200. Such detachment reveals a distal opening 203 for passage of the proximal end 306 of the extruder 106. Thus, the proximal end 306 is advanceable into the distal opening 203 where it is received by the outlet 210 of the indexer 104 (see FIG. 16).

Together, the indexer 104 and extruder 106 may be considered a microfluidic coaxial flow initiator system. Thus, FIG. 21A illustrates the microfluidic coaxial flow initiator system in an assembled configuration and FIG. 21B illustrates the disassembled configuration. In some embodiments, the extruder 106 contains the most geometrically constrictive fluid flow path, namely the microfluidic channel 302. Disassembly of the two components allows for access and optional removal of this small orifice in the system 100, the open microfluidic channel 302 within the extruder 106. Removing the extruder 106 often removes any blockage in the system 100.

Removal of the extruder 106 allows for inspection, debris removal, cleaning, flushing, or renewal of an otherwise inaccessible portion of a microfluidic junction. The indexing chamber 206 is likewise exposed upon disassembly and may be similarly treated. Separating the microfluidic coaxial flow initiator system opens those spaces where fluid pathways meet to provide direct access to the most restrictive areas where blockages would most likely occur. Separating components allows for the blockages to be cleared, or the extruder 106, which may contain the only microfluidic channel 302 in the system 100, to be replaced.

In addition, this enables swapping one extruder type for another, which allows the geometries of the microfluidic channel(s) 302 to change. In some embodiments, the extruder 106 is disposable.

The indexer 104 and extruder 106 are connected and held in place by an interlocking feature. In FIGS. 21A-21B the interlocking feature is comprised of threaded features which are able to engage and disengage. Thus, in this embodiment, the distal opening 203, shown in FIG. 21B, reveals a first threaded feature 350. The first threaded feature 350 lines an inner portion of the outlet 210 of the indexer 104 (see FIG. 16), thus forming a threaded port. A second threaded feature 352 is located near the proximal end of the extruder 106 for engagement with the first threaded feature 350. Thus, in this embodiment, the extruder 106 is reversibly fixated to the indexer 104 by rotating the extruder 106 so as to engage the second threaded feature 352 with the first threaded feature 350. Consequently, one open end of the microfluidic channel 302 is thus positioned within the indexing chamber 206 such that the fluid interface 212 is positioned in a tangentially planar position relative to the longitudinal axis 304 of the channel 302 running a length of the extruder 106. In addition to holding the parts in place in a specific position, the threaded interface seals pressure. In some embodiments, the overall shape of the interface of the first and second threaded features 350, 352 is conical which centers the extruder 106 with respect to the indexing chamber 206. Threaded features can be easily manipulated by hand and are relatively easy to manufacture. In a preferred embodiment, an extruder 106 is attached and detached manually by rotation.

Various configurations of an interlocking feature are possible. In many cases, the threaded port design is convenient, at least in part because it can be combined with a conical sealing surface. Together, these features form a pressure tight seal that aligns the indexing chamber 206 and the extruder 106 and also allow for easy hand-tight installation and removal of the components. However, to achieve the same functional results, various combinations of sealing surface configurations, alignment features, and interlocking features may be used.

In some embodiments, the position of the interlocking feature sets the specified distance d of the tip 310 of the extruder 106 from the fluid interface 212. Referring back to FIGS. 16-17, the proximal end 306 of the extruder 106 penetrates the indexing chamber 206 by a depth set by a seating surface 303 (which is engages a seating portion of the outlet 210) and the interlocking feature (which is comprised of the first and second threaded features in this embodiment). In some embodiments, the placement of the interlocking feature and the sealing surfaces on both mating parts ensure that the proximal end 306 of the extruder 106 extends into the indexing chamber 206 by a set length such that the tip 310 of the extruder 106 is not more than a particular distance from the location of the fluid interface 212, between the first and second fluid inlets 125, 127. It may be appreciated that in some embodiments, the seating surface 303 has a conical shape that conveniently provides alignment along the longitudinal axis 208 of an indexing chamber 206. In other embodiments, the seating surface has a flat shape. Alternatively or in addition, polymers or deformable materials may be used to form a tight fit between the components. When assembled, the seating surfaces and interlocking feature forms a tight seal against pressure.

Figure 22:
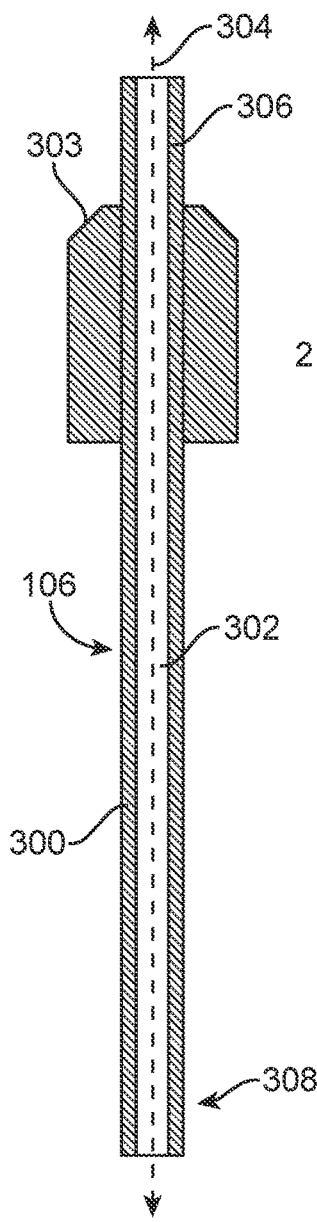
FIG. 22 provides a stylized illustration of a cross-section of an embodiment of an extruder.

FIG. 22 provides a stylized illustration of a cross-section of an embodiment of an extruder 106. As mentioned previously, the extruder 106 comprises an elongate body 300 having a generally tube shape enclosing at least one microfluidic channel 302 that extends along its longitudinal axis 304. The extruder 106 has a proximal end 306 that inserts at least partially within the indexer 104 and receives coaxial flow, and a distal end 308 opposite the proximal end 306 for outflow. The at least one microfluidic channel 302 extends from the proximal end 306 to the distal end 308 of the extruder 106. FIG. 22 also illustrates a seating surface 303 having a conical shape. This stylized illustration is also used throughout FIGS. 18A-18C and FIGS. 19-20 to represent the extruder 106.

Figure 23A:
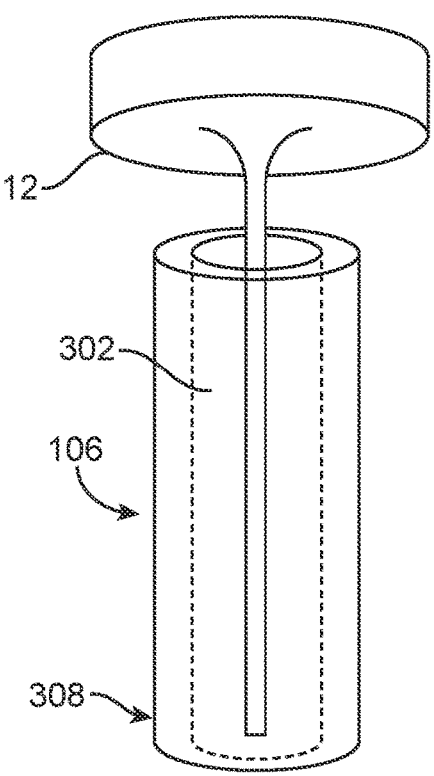
FIGS. 23A-23B illustrate a microfluidic channel that is too short (FIG. 23A) to allow for complete droplet formation while traveling through the channel and a lengthened microfluidic channel (FIG. 23B) which allows periodic perturbations to occur partway down the channel before breaking into droplets.
Figure 23B:
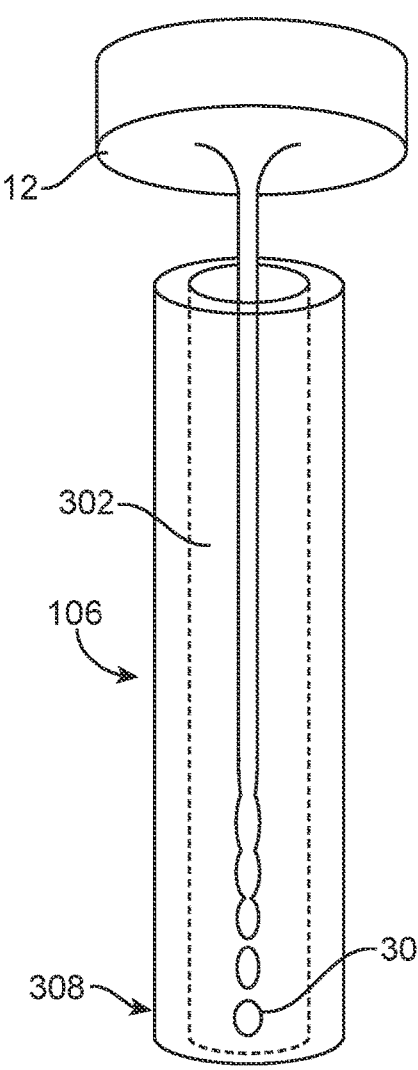

As mentioned previously, the extruder 106 receives the coaxial flow from the indexer 104 into the microfluidic channel 302 wherein droplet formation occurs. FIGS. 23A-23B illustrate the effect of the length of the microfluidic channel 302 on droplet formation. Here, the first fluid (which enters the first fluid inlet 125 and resides above the fluid interface 212) is shown in black and forms the "core fluid". The second fluid (which enters the second fluid inlet 127 and resides below the fluid interface 212) is transparent and flows down the channel 302 forming a sheath around the core fluid. FIG. 23A illustrates a microfluidic channel 302 that is too short to allow for complete droplet formation while traveling through the channel. The time for droplet formation is constant, so as flow rate increases, the distance along the channel 302 where the droplets form increases. Due to the high fluid flow rates generated by the base station 102, a longer channel 302 is needed to allow for droplet formation. By lengthening the channel 302, as illustrated in FIG. 23B, periodic perturbations occur partway down the channel 302 before breaking into droplets 30 before exiting the distal end 308 of the extruder 106. Typically, the microfluidic flow channel 302 has a length of between 5 and 100 millimeters. For most applications, this length allows for the formation of droplets 30 from a coaxial flow of fluids at most flow conditions.

It may be appreciated that the length of the microfluidic channel 302 should be reduced as much as possible, since the pressure drop along the microfluidic channel 302 is significant. However, it takes time for droplets 30 to form from the core of a stream of a continuous coaxial flow. In some embodiments, the linear flow rate in the microfluidic channel 302 is approximately 2 meters per second. Considering a case where the desired droplet size is set at 1 micrometer diameter, and the distance between each droplet is 2 micrometer center-to-center, then 2 linear micrometers of coaxial fluid flow is required to produce each droplet 30, and if the frequency of droplet production is set at 1 MHz, then the linear flow of fluid must be 2 meters per second in a laminar flow channel However, the microfluidic channel 302 does not need to be very long, since a microfluidic coaxial flow can be caused to form droplets within a fraction of a second. To determine the actual length of microfluidic channel 302 required, the time for a coaxial flow breakup as measured from its initiation point can be considered its time of flight (TOF). For example, if the TOF is ¹⁄₁₀ second and the linear flow is 2 meters per second, then the extruder channel 302 must extend a minimum of 20 centimeters. However, by coupling a pulsed energy source into the coaxial flow (as will be described in later sections), the TOF can be reduced, and the length of the microfluidic channel shortened. Using the same example, if the TOF can be reduced to ¹⁄₁₀₀ second, then the droplet formation channel can be reduced in length to 2 centimeters. It may be appreciated that such a reduction in microfluidic flow path allows for faster flow rates or a lower pressure regimen, and that adjusting the parameters of a coupled pulsed energy source into the coaxial fluid flow introduces yet another system variable that must be balanced against other variables in support of a specific quant production regimen.

In some embodiments, the channel 302 has a nominal cross-sectional area of between 0.1 square micrometers and 10,000 square micrometers with a preferred range of between 20 and 1000 square micrometers. These dimensions support laminar flow in a microfluidic channel 302. Typically, a cross-sectional area of up to 10,000 square micrometers is the maximum diameter channel 302 that would be considered to support laminar flow regime. Likewise, as the diameter increases, the proportion of sheath flow (e.g. aqueous solution 24) to core flow (e.g. reagent solution 20) increases. Practically speaking, it is desired to manage the total quantity of aqueous solution 24 when producing large quantities of quants so as to include a high concentration of quants per quantity of aqueous solution.

As mentioned, dimensional considerations are essential for proper quant preparation. In one embodiment, quants are produced in a microfluidic channel 302 that is approximately 30 micrometers in diameter, flowing an aqueous buffer sheath with an inner laminar coaxial flow is about 0.75 micrometers in diameter. When the inner flow is divided into partitions, the aforementioned geometries produce partitions that are about 1 micrometer in diameter with a center-to-center spacing of about 2 micrometers. Conveniently, the ratio of aqueous fluid to solvent in this regime is more than 5000:1, meaning that the solvent would be able to disperse into a relatively large volume of aqueous fluid. If, for example, the solvent was chloroform, which is about 0.5% soluble in water by volume, then the solvent-laden fluid partitions would dissolve into the aqueous fluid before reaching saturation, leaving quant particles behind.

Different coaxial fluid flow regimens are possible, wherein different fluid ratios are achieved, but practical limitations describe the useful geometric parameters for the system that go well beyond the consideration of solvent absorption into the aqueous sheath fluid. For example, many quant manufacturing regimes would seek to minimize the volumes of solvent and buffer in order to maximize quant titre, which is important in the context of preparing an intravenous dose which is practically limited at a few liters. Similarly, achieving a production rate of at least 1 MHz is an objective driven by the practical requirements of quantum dosing, and minimizing the dimensions of solvent flow, or increasing buffer flow dimensions, or increasing pressure, are but a few of the coaxial fluid flow regime parameters that can be adjusted to suit the application.

It may be appreciated that changing one variable, such as the dimensions of the microfluidic channel 302, impacts other aspects of the total system 100. For example, if the linear flow rate remains at 2 meters per second, and the diameter of the microfluidic channel 302 is reduced, then the pressures required to sustain that flow rate must increase. Similarly, if the diameter of the microfluidic channel 302 is increased, it is possible to increase the flow rate using the same pressures. For each application, practical limitations, such as the maximum volume of an intravenous drug delivery will define the coaxial flow dimensions.

Figure 24:
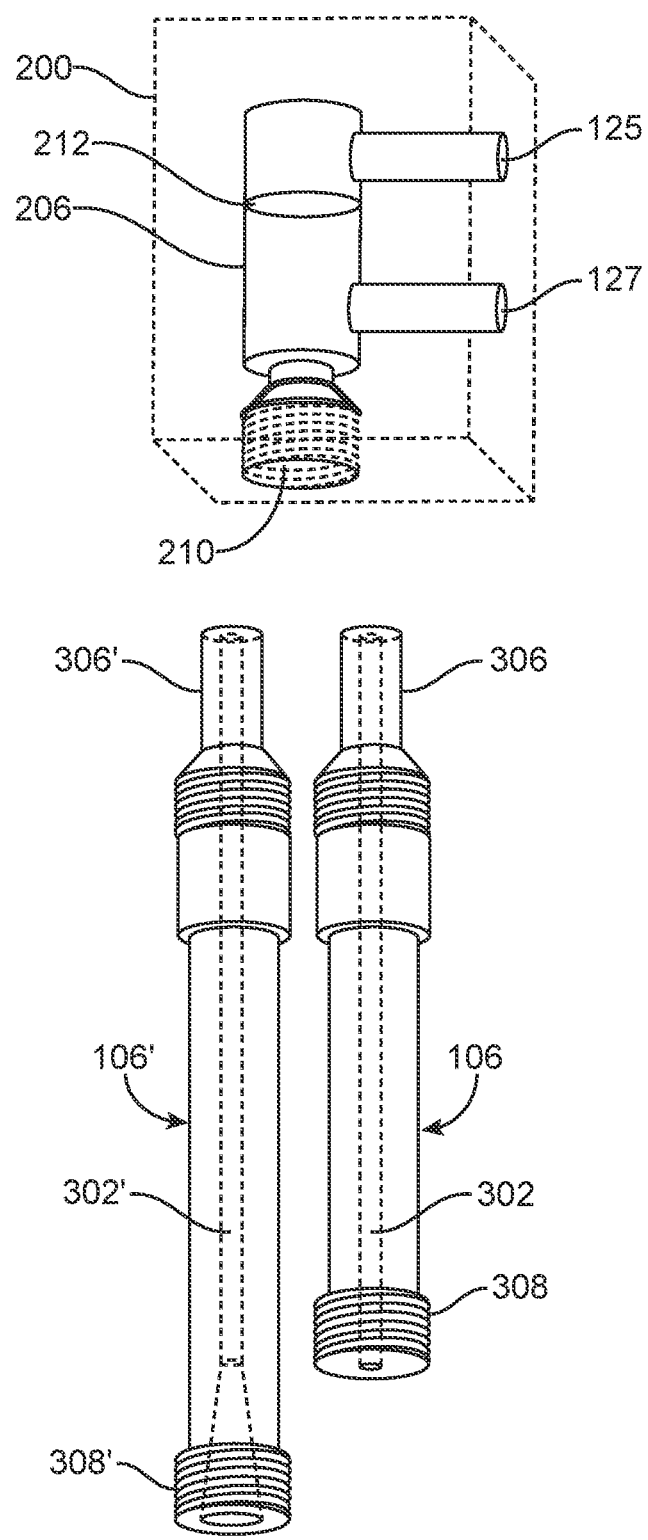
FIG. 24 illustrates the ability to remove an extruder from the indexer and exchange it for another extruder.

FIG. 24 illustrates the ability to remove an extruder 106 from the indexer 104 and exchange it for another extruder 106'. This is a convenient means for changing the operational parameters of the system 100 in much the same manner that a light fixture accepts different bulbs with different wattages. A standard base station may thus be used to operate disposable extruders 106 with different flow paths and other internal features. Examples of different disposable extruders 106 include extruders with multiple flow path channels, or channels with different dimensions, or comprised of different materials. Thus, in some embodiments, a plurality of extruders is available having standardized connection features/interlocking features for easy exchange. Thus, the plurality may include extruders designed for different purposes. In some embodiments it is desirable to slow the flow of fluids flowing out of the extruder 106. Thus, in FIG. 24 the another extruder 106' has a microfluidic channel 302' wherein the cross-sectional area of the channel 302' is larger toward its distal end 308' than it is near its proximal end 306'. For example, if fluids are traversing the microfluidic channel 302' at a rate of 2 meters per second, then they will exit the distal end 308' at the same velocity. However, if the diameter of the microfluidic channel is tapered such that it is larger at the exiting, distal end, then the fluid flow will slow proportionally to the area of the channel diameter. Since the droplets 30 have already formed prior to entering the portion of the channel 302 having an expanded diameter, laminar flow is not needed in this portion. In addition, slower flow may be beneficial to avoid unwanted shear forces that could damage the droplets by causing merging or breaking up.

It is understood that any number of extruder 106 variants can be accommodated by the same base station 102, and that the operating parameters of the base station 102 can be set to different fluid flow settings. In some embodiments, the extruder 106 is identified to the computer control unit 103 using a bar code, RF tag, other means of recognition. Recognizing a specific type of disposable component can enable the electronics aboard to change the base station settings to match the disposable. In some embodiments, the settings are uploaded via a network connection. For example, a disposable vendor may make the appropriate settings available to the base station for download.

Figure 25:
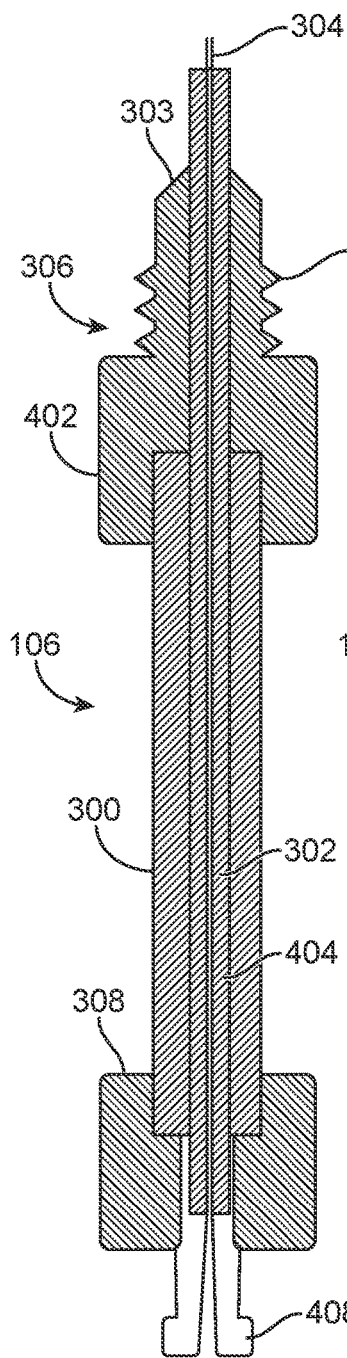
FIG. 25 is a cross-sectional illustration of an embodiment of an extruder.

FIG. 25 is a cross-sectional illustration of another embodiment of an extruder 106. Here, the proximal end 306 comprises a conical portion which penetrates the indexing chamber 206 by a depth set by a seating surface 303 (which is engages a seating portion of the outlet 210). The conical portion also includes an interlocking feature 400 (which is comprised of a threaded feature in this embodiment). Typically, the interlocking feature is able to be engaged by finger tightening. In this embodiment, the proximal end also includes a gripping feature 402 to assist in gripping for finger tightening the interlocking feature. In this embodiment, the microfluidic channel 302 is comprised in part of a semipermeable membrane 404 which extends along the longitudinal axis 304 of the extruder 106. In this embodiment, the distal end 308 of the extruder 106 has a distal interlocking mechanism 408 that is used to link the distal end of the extruder to a downstream collection container or receptacle. In this embodiment, the distal interlocking mechanism 408 comprises a luer fitting.

Figure 26:
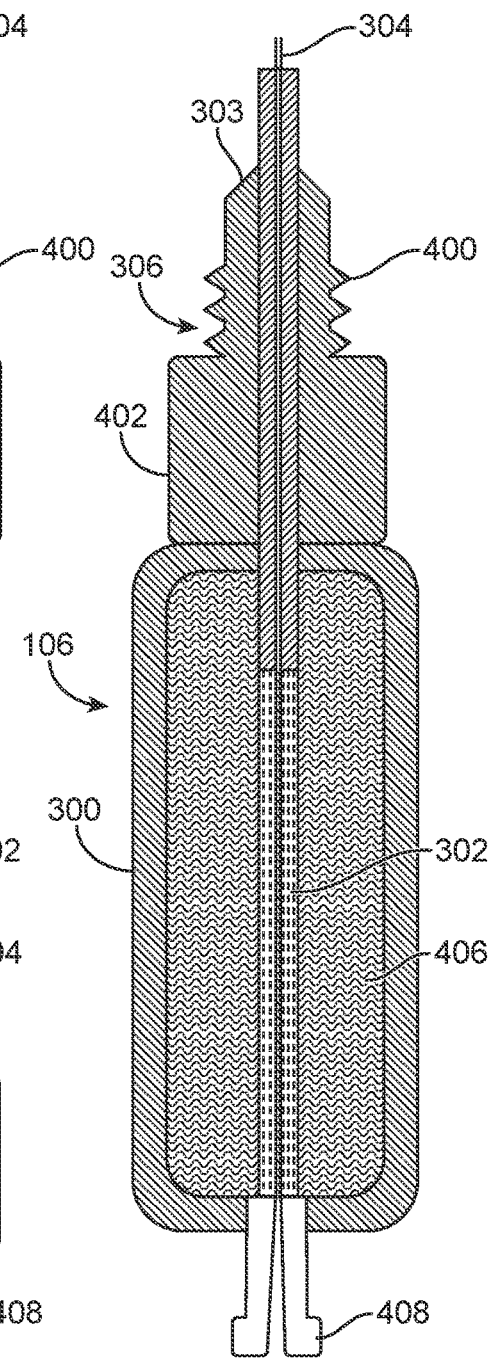
FIG. 26 is a cross-sectional illustration of another embodiment of an extruder.

FIG. 26 is a cross-sectional illustration of yet another extruder 106. Here, the proximal end of the extruder 106 extends beyond the seating surface 303. An interlocking feature 400 (e.g. threads) serves to secure the extruder 106 to an indexer. In this embodiment, the proximal end 306 also includes a gripping feature 402 to assist in gripping for finger tightening the interlocking feature 400. In this embodiment, the microfluidic channel 302 is comprised in part of a semipermeable membrane 404 which extends along the longitudinal axis 304 of the extruder 106. A solvent absorbing material 406 is in contact with the semipermeable membrane 404 and housed between the microfluidic channel 302 and the body 300 of the extruder 106. In this embodiment, the distal end 308 of the extruder 106 has a distal interlocking mechanism 408 that is used to link the distal end of the extruder to a downstream collection container or receptacle. In this embodiment, the distal interlocking mechanism 408 comprises a luer fitting.

Figure 27:
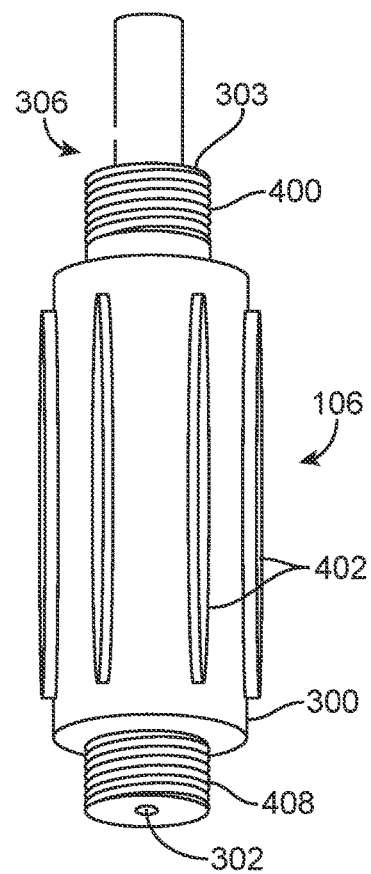
FIG. 27 is an external view of an embodiment of an extruder.
Figure 28:
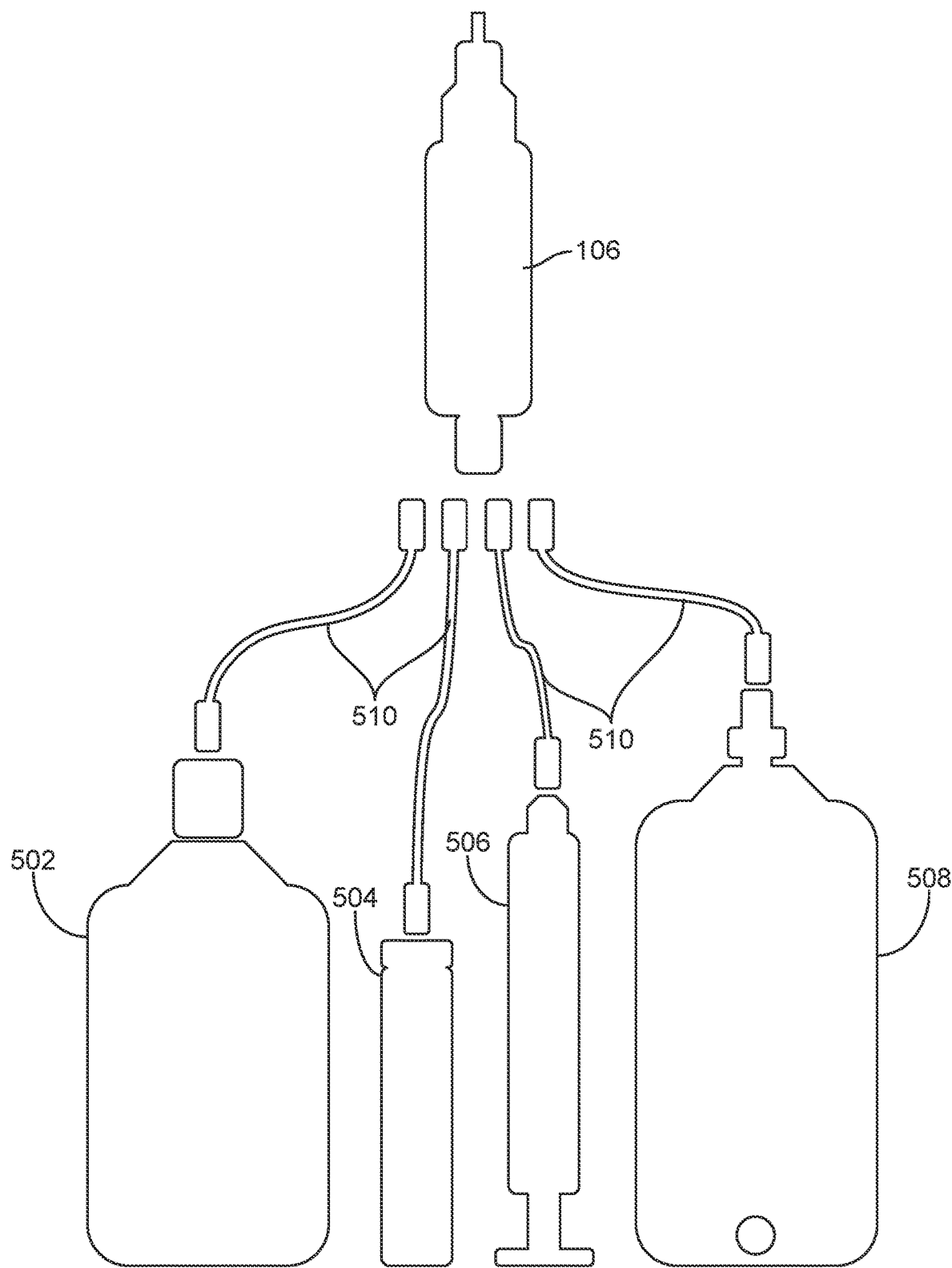
FIG. 28 illustrates a variety of example reservoirs which may be connected to the extruder.
Figure 29A:
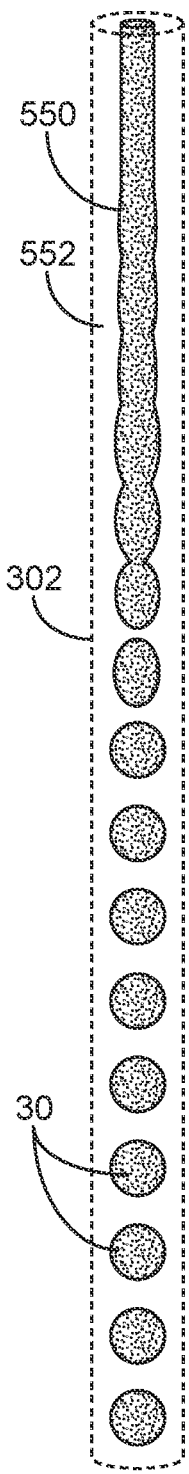
Figure 29B:
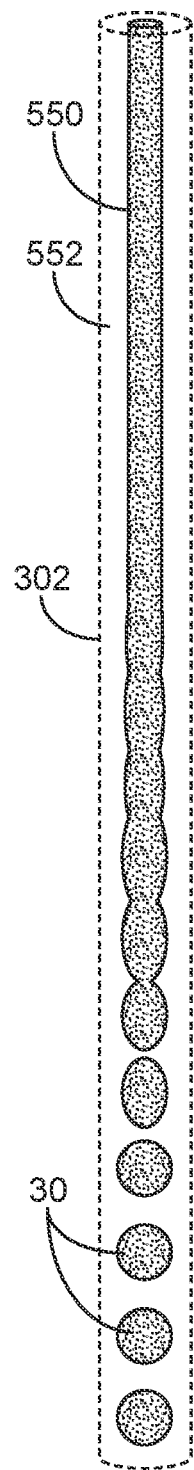
Figure 29C:
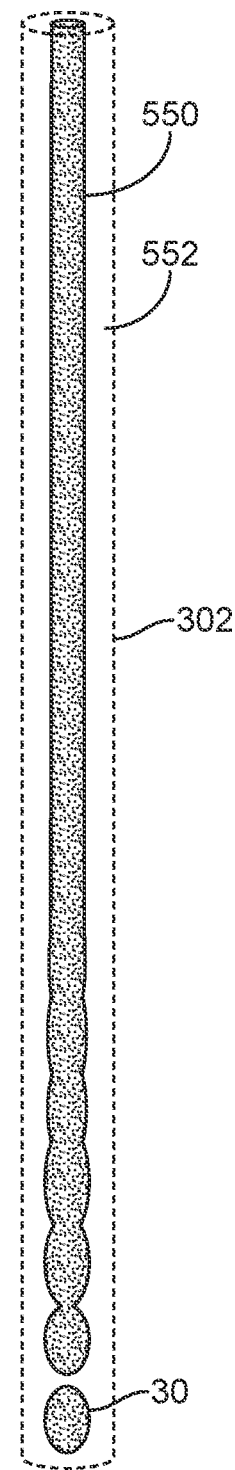
Figure 30D:
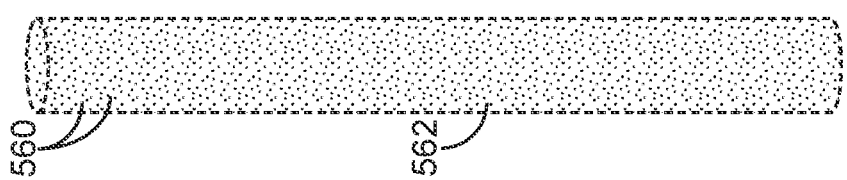
FIGS. 30A-30P illustrates various additional example fluid flow conditions that could occur in a microfluidic pathway, such as microfluidic channel
Figure 30C:
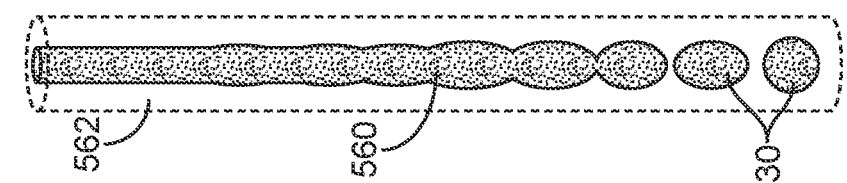
Figure 30B:
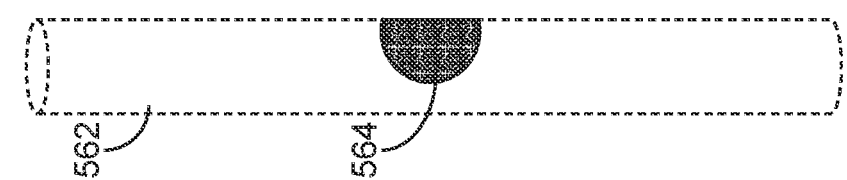
Figure 30A:
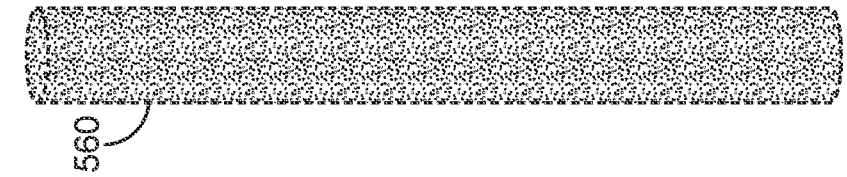
Figure 30H:
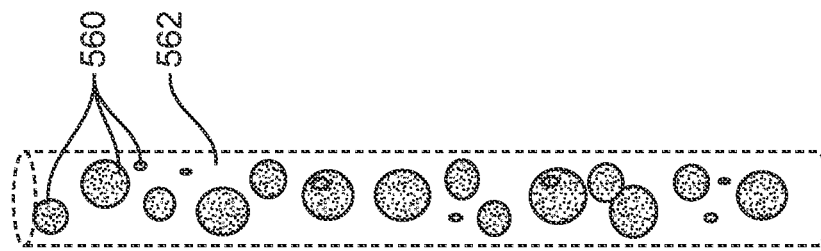
Figure 30G:
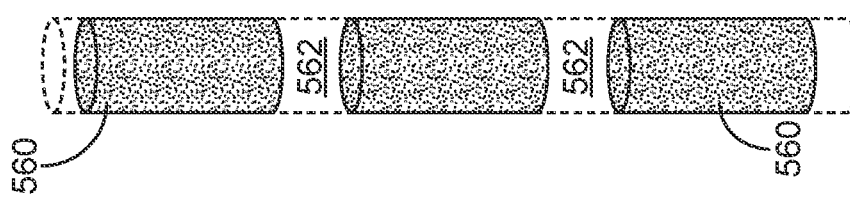
Figure 30F:
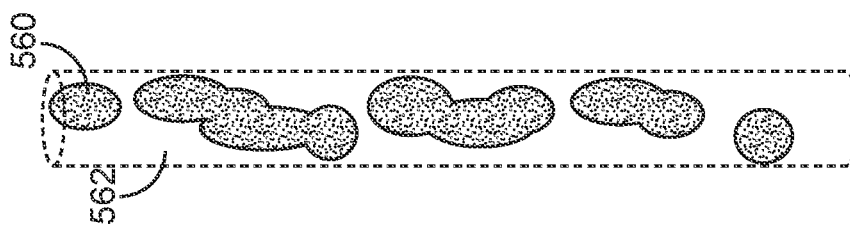
Figure 30E:
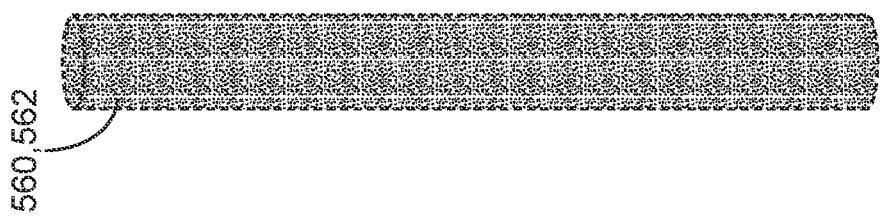
Figure 30L:
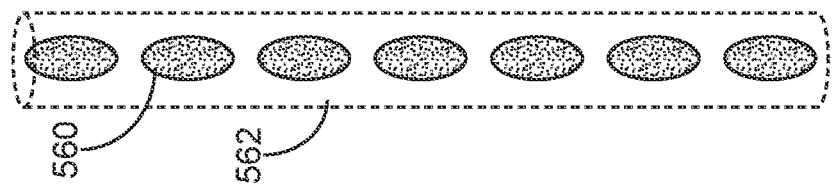
Figure 30K:
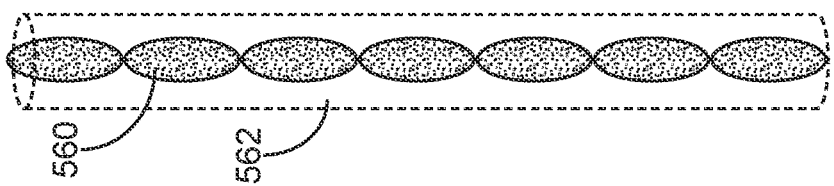
Figure 30J:
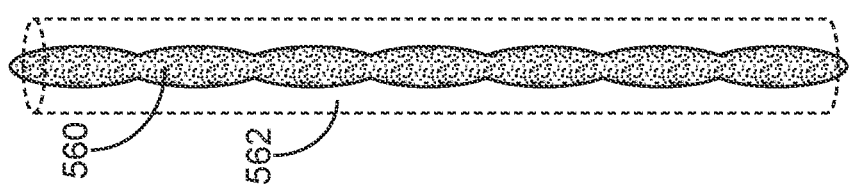
Figure 30I:
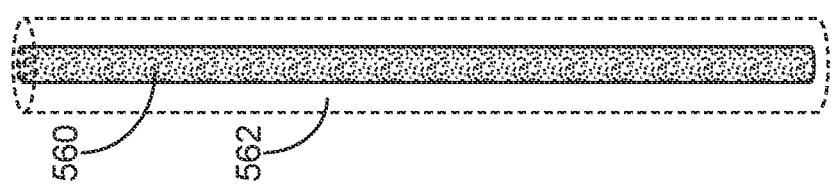
Figure 30P:
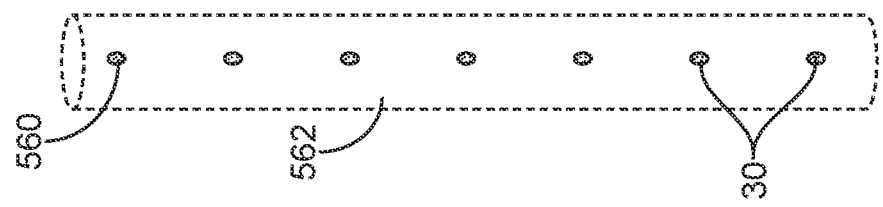
Figure 30O:
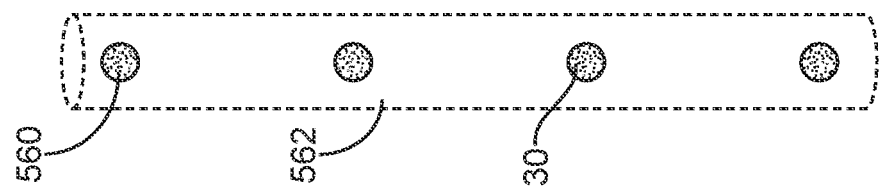
Figure 30N:
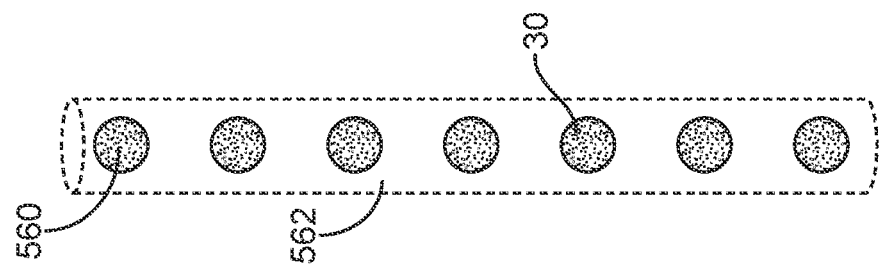
Figure 30M:
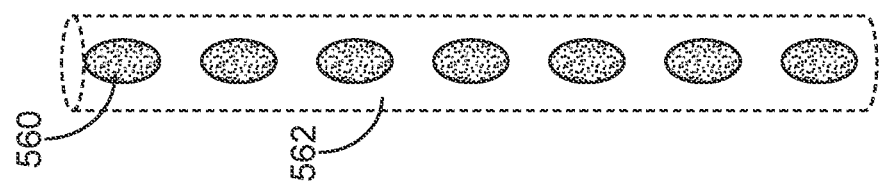

FIG. 27 is an external view of another embodiment of an extruder 106. Here, the proximal end 306 of the extruder 106 extends beyond the seating surface 303. An interlocking feature 400 (e.g. threads) serves to secure the extruder 106 to an indexer. In this embodiment, body 300 includes gripping features 402 to assist in gripping for finger tightening the interlocking feature 400. In this embodiment, the distal end 308 of the extruder 106 has a distal interlocking mechanism 408 (e.g. threads) that is used to link the distal end of the extruder to a downstream collection container or receptacle.

In some instances, it may be convenient to remove solvent from the outflowing fluid product. In some embodiments, this is accomplished by incorporating a membrane or a media bed into the extruder 106 that separates and absorbs solvent. In some embodiments, the extruder contains a semipermeable membrane or a solvent absorptive material.

In another embodiment, the extruder further comprises at least one reagent reservoir containing the type and volume of fluid reagent corresponding a particular assay or function. Like a printer cartridge, it can be preloaded with the relevant chemistries onboard. For example, a vendor could supply a cartridge that contained drug laden solvent. Loading the cartridge into the machine would generate those drug particles in a point-of-care setting.

Quant size will vary according to function, but in general quants are typically on the order of about 100 nanometers in diameter. Size control is essential to function. Droplets 30 are therefore produced with a mean diameter as measured as a population coefficient of standard deviation (% CV) of not more than 50%, more preferably 40%, or 30% or 20% or even more preferably, not more than 10%. There is a linear relationship between droplet size and finished particle size. Therefore, if droplets are produced to a specific size control standard as previously disclosed, then the drug particles are likewise produced with a coefficient of variation of not more than 50%, more preferably 40%, or 30% or 20% or even more preferably, not more than 10%. Consistent and controlled production methods allow for drug particles to be created and collected in a known quantity, which is an essential aspect of accurate dosing.

In some embodiments, the distal end 308 of the extruder 106 is mechanically and fluidly connected to a reservoir or other fluid conduit that receives the outflow from the microfluidic channel 302. FIG. 28 illustrates a variety of example reservoirs 500 which may be connected to the extruder 106. In some embodiments, the reservoir comprises a bottle 502, a vial 504, a syringe 506 or an IV drip bag 508. In some embodiments, the extruder 106 connects directly to the reservoir 500 and in other embodiments the extruder 106 connects to a conduit 510 leading to the reservoir 500. Alternatively, in other embodiments, the extruder 106 has a connection arranged such that the outflow is delivered directly to the patient, such as via an intravenous connection. It may be appreciated that in some embodiments, the extruder 106 contains an additional interlocking feature near its distal end 308, such as a Luer lock, threaded feature, mechanical, or interference fit port, that seals the extruder 106 to a fixture associated with the reservoir 500 or other receiving device or accessory.

In some embodiments, solvent removal or particle characterization steps occur downstream of the extruder. For example, a vacuum membrane unit may be coupled to the outflow of the extruder 106 so that solvent is extracted from the nanoparticle suspension. This also facilitate the downstream movement of output fluid for further processing.

D. Measurement and Control of Droplet Formation

FIGS. 29A-29F illustrates various example fluid flow conditions that could occur in a microfluidic pathway, such as the microfluidic channel 302, some of which lead to successful droplet formation and some of which do not. A first fluid 550 is depicted as black, and a second fluid 552 is transparent. In each case, the flow direction is top to bottom. FIG. 29A depicts an unbroken coaxial flow extending approximately ⅓ the length of the flow path with droplets thereafter. FIG. 29B depicts an unbroken coaxial flow extending approximately ⅔ the length of the flow path with droplets thereafter. FIG. 29C depicts an unbroken coaxial flow extending approximately ⅞ the length of the flow path with droplets thereafter. FIG. 29D depicts an unbroken coaxial flow occupying approximately ⅓ of the cross-sectional area of the flow channel FIG. 29E depicts an unbroken coaxial flow occupying approximately ⅙ of the cross-sectional area of the flow channel FIG. 29F depicts an unbroken coaxial flow occupying approximately ⅒ of the cross-sectional area of the flow channel FIGS. 30A-30P illustrates various example fluid flow conditions that could occur in a microfluidic pathway, such as microfluidic channel 302, many of which do not lead to successful droplet formation. A first non-conductive fluid 560 is black and a second conductive fluid 562 is transparent. In each case, the flow direction is top to bottom. FIG. 30A illustrates is a flow channel flowing the first fluid 560 only. FIG. 30B illustrates the second fluid 562 flowing past a blockage 564 comprised of a different fluid. FIG. 30C illustrates a coaxial flow breaking into regular droplets 30. FIG. 30D illustrates a flowing mixture of the first and second fluid 560, 562. FIG. 30E illustrates a flowing mixture similar to that of FIG. 30D, but with a greater concentration of the first fluid 560. FIG. 30F illustrates an irregular flow of first fluid 560 with large droplets forming. FIG. 30G illustrates a regular flow of slugs of the first fluid 560 and the second fluid 562. FIG. 30H illustrates an irregular flow of and emulsion as in FIG. 30F, but with smaller droplets. FIG. 30I illustrates an unbroken coaxial flow. FIG. 30J illustrates an unbroken perturbed coaxial flow. FIG. 30K illustrates an unbroken coaxial flow with marked perturbations. FIG. 30L illustrates a regular periodic flow of separated droplets 30 with a pronounced linear deformation along the channel central axis. FIG. 30M illustrates a regular periodic flow of separated droplets 30 as in FIG. 30L but with a lesser linear deformation along the longitudinal axis of the microfluidic channel 302. FIG. 30N illustrates a regular periodic flow of droplets 30. FIG. 30O illustrates a regular periodic flow of droplets 30 as in FIG. 30N but with a smaller diameter and twice the period of FIG. 30N. FIG. 30P illustrates a regular periodic flow of droplets 30 as in FIG. 30N but with a smaller diameter.

It is important to monitor and recognize irregular fluid flow conditions during operation because those irregularities will be translated into inconsistent droplet size and inconsistent nanoparticle characteristics. Successful quant production requires regular and consistent fluid flow and the ability of a manufacturing system to recognize and respond to the failure modes which is an important aspect of ensuring that the quants are produced to specification. Conventional microfluidic systems are generally bereft of active control; their operation is assumed to remain stable based on external factors, including a steady fluid supply, proper reagent filtration and degassing, and a stable ambient temperature. Indeed, controlling external factors is adequate for some in-house manufacturing processes and disposable batch sample prep applications. However, high-titre production of nanoparticles rely on continuous or semi-continuous operation, modular disposables, and integrated quality assurance. These demands highlight the need to measure and correct microfluidic flow conditions in real time.

Electrical impedance is a common means of counting and characterizing particles in a fluid suspension. Devices using this approach, such as particle size analyzers and cell counters, determine particle size by measuring the electrical impedance as they pass through an orifice filled with a conductive fluid. But while this method is well suited to measure discrete events passing through a physical constriction, it is ill suited to measure the steady flow conditions in a linear uniform channel as required for coaxial flow and high speed droplet formation. Likewise, there are conventional methods to measure particles and discrete events in microfluidic circuits, but nothing to measure continuous events, such as characterization of a coaxial flow, or the frequency of microdroplet production. What is needed is a system that gives immediate feedback to the rest of the system such that target measurements are kept in specification. Methods and devices are provided herein to conveniently measure the state of a coaxial flow.

As mentioned previously, in some embodiments the system 100 includes a computer control unit 103, comprising a controller bus 150 and a computer 152, which allows for a flow of data to monitor and control key aspects of the partitioning process. The control unit 103 uses the electrical characteristics of the fluid filled conduits while the fluids are flowing. Each flow state will reveal itself through changes in conductivity along the flow path with respect to time and frequency. Suitable measurement methods include resistance, current, and voltage.

In some embodiments, the core fluid (e.g. reagent fluid 20) is non-conductive and the sheath fluid (e.g. aqueous buffer solution 24) is conductive. In some embodiments, changes to an electrical signal passing through the conductive fluid filling a length of a microfluidic channel 302 are measured to characterize the coaxial flow. A combination of two or more fluids with different conductance flowing in such a circuit will occupy varying proportions of the channel cross section, and the electrical properties of said circuit will thus change in proportion to the relative area occupied. Every flow condition will have an electronic fingerprint and recognizing the electrical characteristics of such a circuit provides feedback for its control, in terms of its physical dimensions, conformation, and breakup.

Figure 31A:
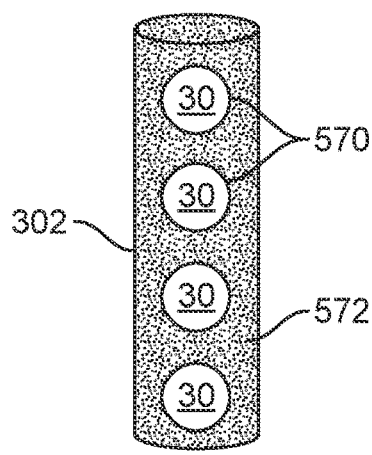
FIGS. 31A-31C illustrates a flow channel, such as a microfluidic flow channel, having a regular periodic stream of uniform droplets flowing therethrough.
Figure 31B:
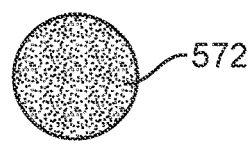
Figure 31C:
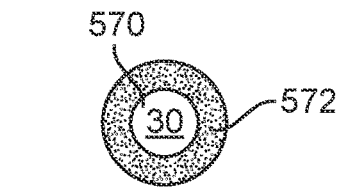

FIGS. 31A-31C illustrates a flow channel, such as a microfluidic flow channel 302, having a regular periodic stream of uniform droplets 30 flowing therethrough. The droplets 30 are formed from a non-conductive fluid 570 shown in white and a continuous conductive fluid 572 is shown in black. FIGS. 31B-31C illustrate two conductive cross-sections of the same flow channel 302. FIG. 31B illustrates a maximum conductive cross-section comprised entirely of conductive fluid 572 which occurs between droplets 30. FIG. 31C illustrates a minimum conductive cross-section through the maximum circumference of a droplet 30.

In some embodiments, a complete circuit is formed by passing an electric current between two electrodes, one at each end of the microfluidic channel 302. Such arrangement permits the measurement of the conductive path formed by a conductive fluid flowing therein. A change in the shape of the fluids flowing through the channel alters the cross section of the conductive path, and the dimensions and conformation of the fluids flowing in the circuit can be ascertained by virtue of their electrical properties at a given point in time.

Figure 32:
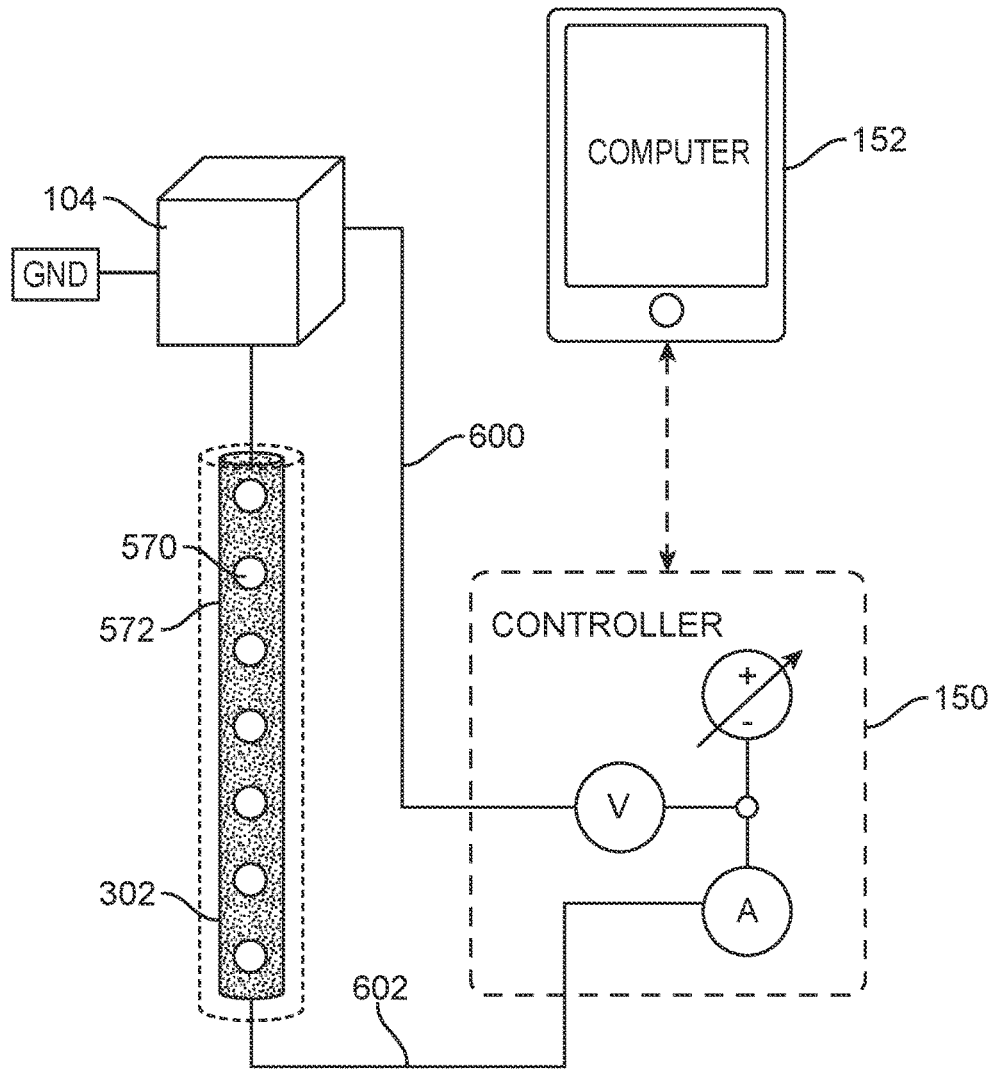
FIG. 32 is a schematic illustration of a microfluidic circuit.

FIG. 32 is a schematic illustration of a microfluidic circuit. Here, a conductor 600 supplies a common grounded source to an indexer 104 and a controller bus 150 connected to a computer 152. The microfluidic channel 302 is depicted with a non-conductive fluid 570 (indicated as white), and a conductive fluid 572 (indicated as black). Another conductor 602 completes the circuit by connecting the channel 302 to the controller bus 150.

A complete microfluidic circuit as disclosed herein can be characterized in terms of voltage (Volt), current (Ampere), resistance (Ohm), conductance (Siemen), capacitance (Farad), charge (Coulomb), inductance (Henry), power (Watt), impedance (Ohm), and/or frequency (Hertz). Such parameters and their means of measurement across a circuit are well known to the arts. Significantly, each of these measurement types can reveal the conditions of a flowing circuit independently or in combination, when compared to a corresponding control measurement.

In some embodiments, the controller bus 150 is connected to both ends of the microfluidic channel 302, as illustrated in FIG. 32, so as to measure electrical signals across the circuit, as well as receive data, store data, and perform logical functions as output signals. Electronic systems of the type described herein are broadly described as computers, are well known to the arts, and are thus depicted as a box connected showing the flow of signals as inputs and outputs in a schematic diagram. Connections are shown at each of the microfluidic channel 302 where conductive electrodes/conductors make contact with the flow path, but these signals are ultimately connected by virtue of logical functions to each of the other aspects of the system 100. In this way, pressure sensors, stepper motors, pulse generators, and other electronic aspects of the apparatus are connected, and can be affected using external inputs by negotiating a communications protocol to additional devices, like RS-232.

In some embodiments, the controller bus 150 is comprised of a collection of electronic components that may optionally comprise a camera, real time customer services, data logging, and a wireless connection. Such additional use of information obtained from real time measurement of a microfluidic circuit may have additional uses such as quality control, batch control, user tracking and monitoring, disposable element management, internal diagnostics, device time and sundry other useful features that are common to "connected" devices.

In some embodiments, the controller bus 150 is also capable of uploading new software and be used to unlock new features that enable the system 100 to operate in a different predefined mode. In some instances, some of the computing processes are performed externally, using a laptop, desktop, iPad, or cloud network.

Figure 33:
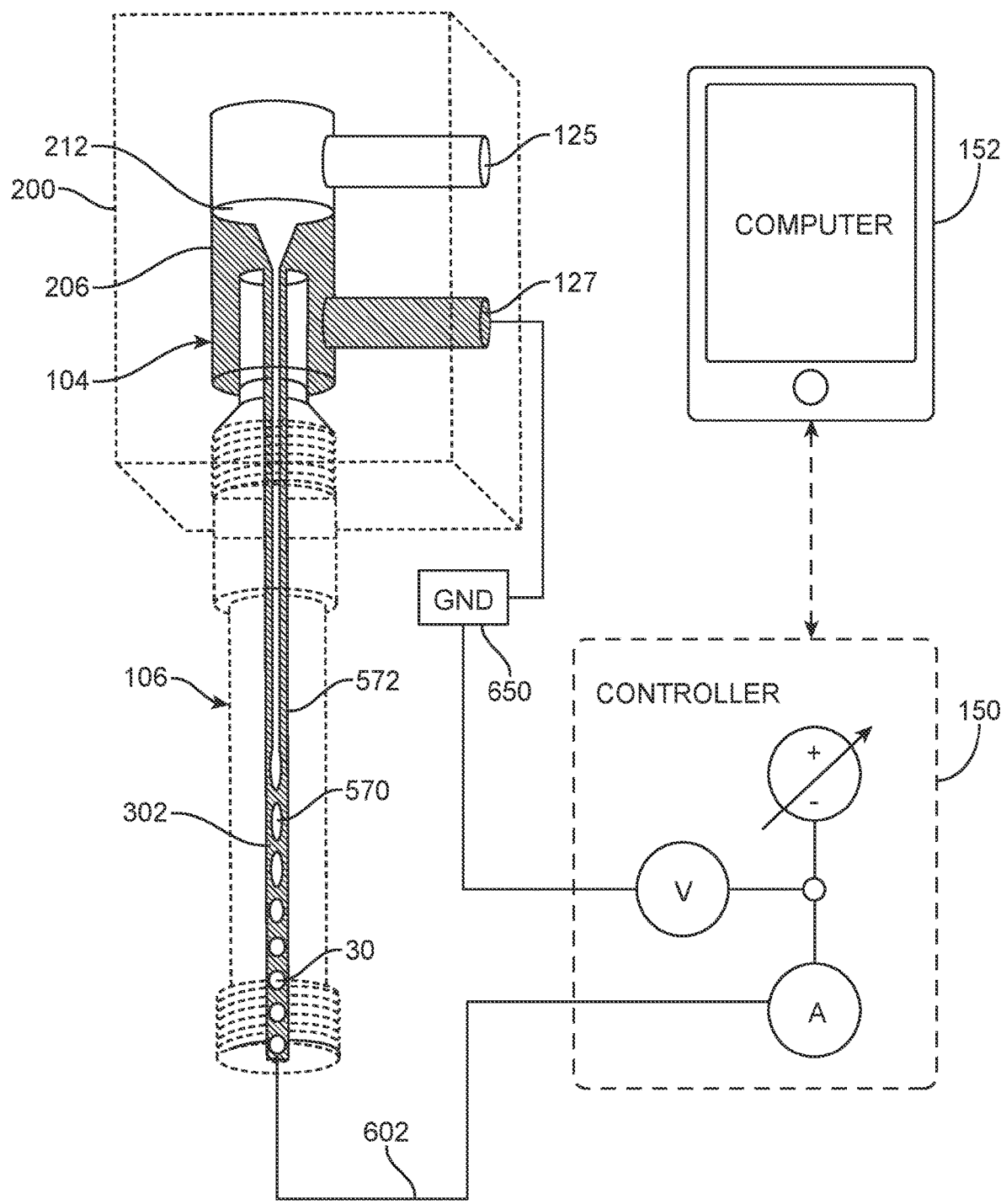
FIG. 33 is a schematic illustration of a microfluidic circuit as in FIG. 32 but applied to an assembled coaxial flow initiator comprised of an indexer and extruder.

FIG. 33 is a schematic illustration of a microfluidic circuit as in FIG. 32 but applied to an assembled coaxial flow initiator comprised of an indexer 104 and extruder 106. Again, conductive fluid 572 within the coaxial flow initiator are shown in black and non-conductive fluid 570 is shown in white. In this embodiment, an indexing chamber 206 encloses the two fluids 570, 572. The non-conductive fluid 570 maintains an unbroken conductive path as it flows into the first fluid inlet 125 of the indexer 104, fills the indexing chamber 206, and enters the channel 302. The non-conductive fluid 572 then breaks up into droplets and exits the channel 302 at the another conductive pathway 602 that leads to the controller bus 150, which is in turn connected to the computer 152. In this embodiment, a grounding wire 650 completes the circuit by connecting the controller bus 150 to the conductive fluid 572 entering the indexer 104 at the second fluid inlet 127.

Not only is droplet formation able to be measured, droplet formation can be controlled by a variety of mechanisms, including induced perturbations. Perturbations in the core flow may be induced by pulsed energy. Thus, in some embodiments, the system 100 additionally comprises mechanisms of coupling pulsed mechanical or thermal energy into the fluid interface 212. Examples of such mechanisms include a laser diode, a piezo ceramic, and/or a voltage source coupled or directed into the fluid flow. Pulsed energy can be used to create regular perturbations in a coaxial flow, and by adjusting the waveform, frequency, and amplitude, it is possible to control the rate of droplet formation with pulsed energy. By inducing regular perturbations into a coaxial flow at an appropriate frequency range and amplitude, the formation of droplets can be induced to correspond to that frequency. In particular, by adding pulsed energy into fluid flow, the time to form droplets from a coaxial flow can be reduced, allowing the length of the microfluidic channel 302 to be reduced by equal measure. Moreover, by reducing the length of the channel 302, the fluid pressure in the indexer 104 may also be reduced. Therefore, adding a pulsed energy into the system 100 can reduce the system pressure requirements. And, although it is contemplated that pulsed energy hardware could be placed within or in contact with the extruder 106, such arrangement does not significantly reduce the complexity or cost of the overall system 100.

Coupling a pulsed energy into the coaxial fluid flow also has the added benefit of improving droplet and thus particle uniformity, which is directly related to the quality of quants produced. While it may be possible to generate functionally uniform quants without a coupled pulsed energy source, the additional ability to control coaxial flow breakup is preferred.

Figures 34, 35:
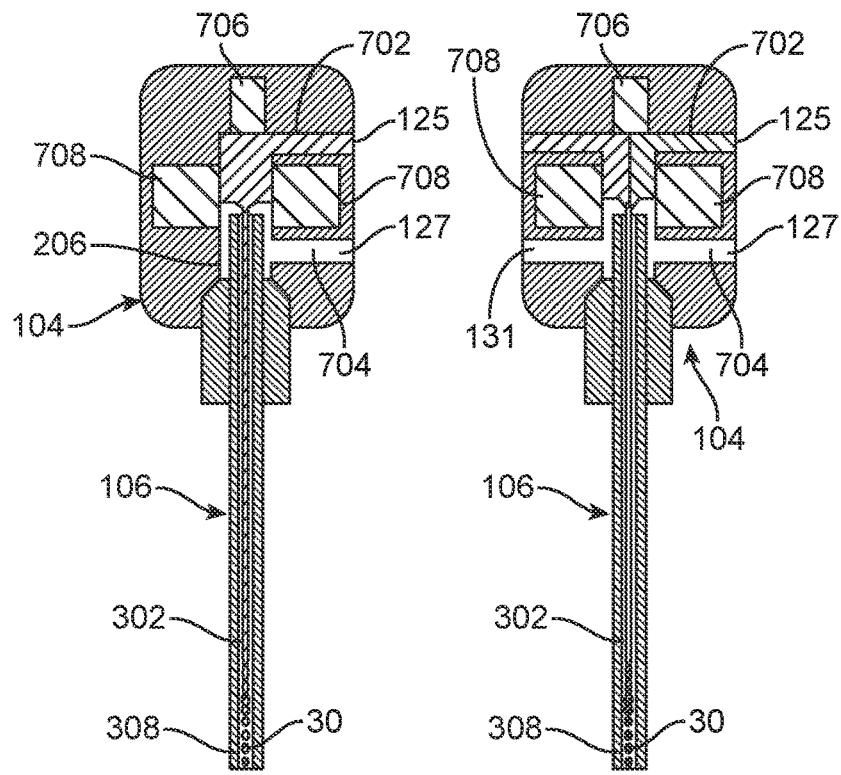
FIG. 34 illustrates an embodiment of an assembled separable microfluidic coaxial flow initiator system in a sectional view including piezo elements in the indexer, demonstrating the flow of a first fluid and a second fluid to form a collection of droplets.
FIG. 35 illustrates a sectional view of an embodiment of an assembled exemplary separable microfluidic coaxial flow initiator system with four fluid ports and including piezo elements in the indexer, demonstrating the flow of three fluids to form a collection of droplets with the additional port available as a waste gate.

FIG. 34 illustrates an embodiment of an assembled separable microfluidic coaxial flow initiator system in a sectional view including piezo elements in the indexer 104, demonstrating the flow of a first fluid 702 and a second fluid 704 to form a collection of droplets 30. Here, the indexing chamber 208 is in fluid communication with the first fluid inlet 125 (containing the first fluid 702) and the second fluid inlet 127 (containing the second fluid 704), wherein the first and second fluids 702, 704 are immiscible. The top of the indexing chamber 206 is in mechanical communication with a cylindrical piezo element 706, and the side walls of the indexing chamber 206 are in mechanical communication with a ring-shaped piezo element 708. The fluids 702, 704 arrange to form the fluid interface 212 that is extruded as it flows through the open proximal end of the microfluidic channel 302 of the indexer 104. The mixture of the first and second fluids 702, 704 that comprise the coaxial flow breaks into droplets 30 before flowing out of the distal end 308 of the extruder 106.

FIG. 35 illustrates a sectional view of an embodiment of an assembled exemplary separable microfluidic coaxial flow initiator system with four fluid ports and including piezo elements in the indexer 104, demonstrating the flow of three fluids to form a collection of droplets 30 with the additional port available as a waste gate. Here, the indexing chamber 206 is in fluid communication with the first fluid inlet 125 and the second fluid inlet 127 containing a first fluid 702 and a second fluid 704, respectively, wherein the first and second fluids are immiscible. The indexing chamber 206 is in fluid communication with a third fluid inlet 129, containing a third fluid 710 which is miscible with the first fluid 702 but also immiscible with the second fluid 704. A cylindrical piezo element 706 is in mechanical communication with the upper surface of the indexing chamber 206, and a ring-shaped piezo element 708 is in mechanical communication with the side walls of the indexing chamber 206. The first and third fluids 702, 710 arrange to form a fluid interface 212 that is extruded as it flows through the open proximal end of the microfluidic channel 302 of the indexer 104. The mixture of the first and third fluids 702, 710 that comprise the core of the coaxial flow breaks into droplets 30 before flowing out of the extruder distal end 308. The additional port 131, also in fluid communication with the indexing chamber 208 is connected to a waste line.

Figures 36, 37:
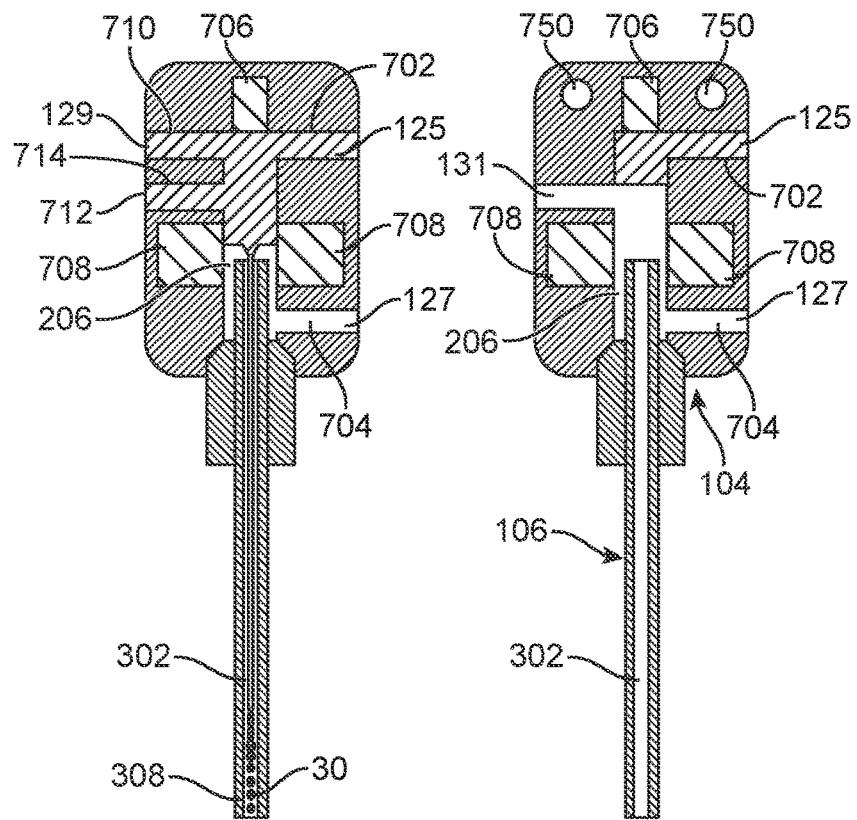
FIG. 36 illustrates a sectional view of a different embodiment of an assembled exemplary separable microfluidic coaxial flow initiator system with four fluid ports and including piezo elements in the indexer, demonstrating the flow of four fluids to form a collection of droplets with the additional port available as a waste gate.
FIG. 37 is a sectional view of an assembled exemplary separable microfluidic coaxial flow initiator system with three fluid ports and including piezo elements and an additional pair of mounting holes in the indexer, demonstrating the flow of two fluids to form a collection of droplets with the additional port available as a waste gate.

FIG. 36 illustrates a sectional view of an embodiment of an assembled exemplary separable microfluidic coaxial flow initiator system with four fluid ports and including piezo elements in the indexer, demonstrating the flow of four fluids to form a collection of droplets with the additional port available as a waste gate. Here, the indexing chamber 206 is in fluid communication with a first fluid inlet 125, a second fluid inlet 127, and a third fluid inlet 129 containing a first fluid 702, a second fluid 704, and a third fluid 710, respectively. In this embodiment, fourth inlet 712 is present containing a fourth fluid 714. In this embodiment, the first fluid 702, third fluid 710 and fourth fluid 714 are at least partially miscible. In this embodiment, the second fluid 704 is an immiscible fluid. A cylindrical piezo element 706 is in mechanical communication with the upper surface of the indexing chamber 206, and a ring-shaped piezo element 708 is in mechanical communication with the side walls of the indexing chamber 206. The fluids arrange to form a fluid interface 212 that is extruded as it flows through the open proximal end of the microfluidic channel 302 of the indexer 104. The mixture of the first, third and fourth fluids that comprise the core of the coaxial flow breaks into droplets 30 before flowing out of the distal end 308 of the extruder 106.

FIG. 37 is a sectional view of an assembled exemplary separable microfluidic coaxial flow initiator system with three fluid ports and including piezo elements and an additional pair of mounting holes in the indexer, demonstrating the flow of two fluids to form a collection of droplets with the additional port available as a waste gate. The indexing chamber 206 is in fluid communication with a first fluid inlet 125 and a second fluid inlet 127 containing a first fluid 702 and a second fluid 704, respectively, wherein the first and second fluids 702, 704 are at least partially immiscible. The indexing chamber 206 is also in fluid communication with an additional port 131 which can be combined with a valve as a waste gate. A cylindrical piezo element 706 is in mechanical communication with the upper surface of the indexing chamber 206, and a ring-shaped piezo element 708 is in mechanical communication with the side walls of the indexing chamber. The fluids 702, 704 arrange to form a fluid interface 212 that is extruded as it flows through the open proximal end of the microfluidic channel 302 of the indexer. In this embodiment, the indexer 104 includes a fixturing or surface mounting feature, illustrated here as a pair of through holes 750.

It may be appreciated that any combination of conductive and non-conductive fluids can be used to create a conductive microfluidic circuit as described above. Preferred conductive fluids include aqueous buffers, and preferred non-conductive fluids include organic solvents. Either or both of the fluids may have one or more molecular species dissolved or particulates, including cells or beads, suspended therein.

It may be appreciated that the above described compositions and methods of providing a circuit for the measurement and control of microfluidic partitioning are merely examples. It should be apparent, to those skilled in the art that many more modifications besides those already described are possible without departing from the inventive concepts herein.

Dosing

Drugs are traditionally considered soluble molecules that are characterized in terms of concentration when determining their therapeutic effect and toxicity. Assessing these parameters is the role of pharmacokinetics which considers a variety of concentration-based measurements. One such measurement is "area under the curve" (AUC). The area under the curve (AUC) is the definite integral in a plot of drug concentration in blood plasma vs. time. In practice, the drug concentration is measured at certain discrete points in time and the trapezoidal rule is used to estimate AUC.

Another measurement is peak concentration (Cmax). Cmax is the maximum (or peak) serum concentration that a drug achieves in a specified compartment or test area of the body after the drug has been administrated and before the administration of a second dose. The time to reach Cmax is the time to peak concentration (Tmax). It is expressed in hours and is useful in estimating the rate of absorption. Onset time and onset of action are dependent upon Tmax. An additional measurement is absorption lag time (tlag). Absorption lag time is a reflection of the processes associated with the absorption phase such as drug dissolution and/or release from the delivery system and drug migration to the absorbing surface. Failure to specify the lag time can lead to inappropriate or erroneous estimates of pharmacokinetic parameters, Thus, traditional dosing is concerned with achieving or maintaining specific molecular concentrations over time. Factoring in physiological patient variables provides the clinician with guidelines for drug concentration and clearance tailored to the individual. Importantly, quantifying the actual target of the therapeutic drug, the targeted tissues or cells, is generally not considered. For example, most cytotoxic cancer drugs are prescribed with respect to patient body surface area as measured in square meters as opposed to the actual target, as in, for example, the number of cells comprising a tumor. A case in point, paclitaxel, may be dosed at 100 mg per square meter for a given number of cycles. Measuring a patient's body surface area approximates a number of other patient variables, such as organ size, that are important proxies for drug clearance. However, traditional dosing calculations do not attempt to measure the number of target cells present. These dosing calculations illustrate the clinical perspective that a maximal safe dose is best, and the real objective of established dosing parameters is to limit unacceptable side effects. In other words, traditional dosing assumes equal access to all tissues as it attempts to achieve a specific concentration of drug over time whereas targeted drug dosing is an asymmetric approach that delivers drug particles to a specific target. Improved drug targeting technology shifts the emphasis of drug dosing regimens from managing side effects to statistically overwhelming targeted cells.

As medical imaging and other diagnostic technologies allow for a more complete picture of patient condition, detailed target information at the cellular level is becoming more available. Likewise, as medical technology evolves closer to cellular resolution, even more detailed target information, and yet more opportunities for targeting those cells, will be revealed.

A. Drugs as Quants

Quants are a working assembly of disparate chemical species, and as such, the division between the biologically active 'drug' and inert 'excipient' loses its meaning. Consider a tripartite nanodrug particle (quant) comprised of structural lipids, an antineoplastic agent, and tumor targeting moieties. In this example, each molecular component comprising the quant synergistically enables the biological activity of the other—and each ingredient is arguably a biologically active compound. Excipients are traditionally considered biologically inert additives, which are used merely to improve the physical properties of a drug prior to patient delivery or improve the performance of the active ingredient. Indeed, the lipid cholesterol may be used in one context as an excipient but is arguably more than that if it is an integral part of a nanodrug assembly that provides structural integrity to a particle that remains intact through target cell uptake. These composite drugs are inherently indivisible molecular blends that cannot be expressed in terms of mass, nor arbitrary election of an "active" ingredient. Quants are typically delivered as emulsions that are best described as the number of particles delivered. For example, 100 mg of a drug may be distributed into any number of discrete quants. Describing an emulsion by drug mass per volume works well for soluble drugs. But for a uniform emulsion of quants wherein all drug particles are the same size, dosing by mass is inappropriate and potentially harmful. After all, a drug particle is either absorbed by a targeted cell, or not. A quant's sundry molecular components perform specific behaviors at their site of action, or not. Just as viruses are measured by 'titre' and TFUs' rather than by mass, quant dosing is best measured in discrete particle numbers. Describing a drug dose in terms of particle number provides for a measure of tumor targeting efficiency at the cellular level. Just as measuring the relative success of tissue targeting is a matter of determining the proportion or number of drug particles in a given location, the best measure of overall cytotoxic drug success is tracking absorption at the cellular level. For most cytotoxic drug applications, drug particles are designed such that a single target cell will be destroyed upon absorbing a single drug particle. This simple calculation allows for a target-centric dosing formula that measures the statistical success of a particular quant dosing regimen in relation to the number of target cells present.

B. Quantum Dosing formula

Quantum dosing assumes that each quant or particle is uniform to the extent that they are interchangeable and can thus only be applied to monodisperse drug emulsions. To determine a statistically significant dose, an equation is applied for each quant design under consideration along with its targeted cell subpopulation. The purpose of the calculation is to determine the number of quants needed to treat a collection of targeted cells with a statistical certainty that every targeted cell has been treated. Using this formula, a dosing plan can be created for an individual patient:

$$T - C = \sum_{n=1}^{Q} \left[ \left( \frac{T}{M} \right) KE \right]_n$$

Where:
T=target cells
C=cumulative target cells treated
Q=number of quants (dose)
M=number of non-target cells
E=effectivity
K=number of cells encountered per second The number of target cells (T) represents the number of cells at which a specific population of quants is directed. For example, (T) may be an estimate of the number of cells in a tumor. Or, given that many tumors are actually comprised of a complex population of different cell types, (T) may represent a subpopulation of a tumor. Importantly, (T) relates only to the population of a particular type of cell at which a population of quants has been directed. (C) is a number that increases with each cycle of the equation and simply keeps a running sum of the targeted cells treated or destroyed. (Q) is the number of a single quant type delivered for a given dose. (M) is the number of non-target cells. These can be thought of as the hay in the haystack, the cells that comprise the bulk of a patient. Effectivity (E) is a value that captures the statistical likelihood that a single quant particle of a particular design will effectively enter a targeted cell. It is a number that is less than one, and can be considered approximately as 1/X, where X is the likelihood that it will enter a targeted cell if it encounters one. The value (E) is an intrinsic characteristic of a specific quant design. (K) is the number of cells encountered during the half-life of a quant. This is an estimate of the number of cells that a single quant will encounter in adequate proximity to recognize as a target or non-target cell while the quant is in circulation.

Figure 38:
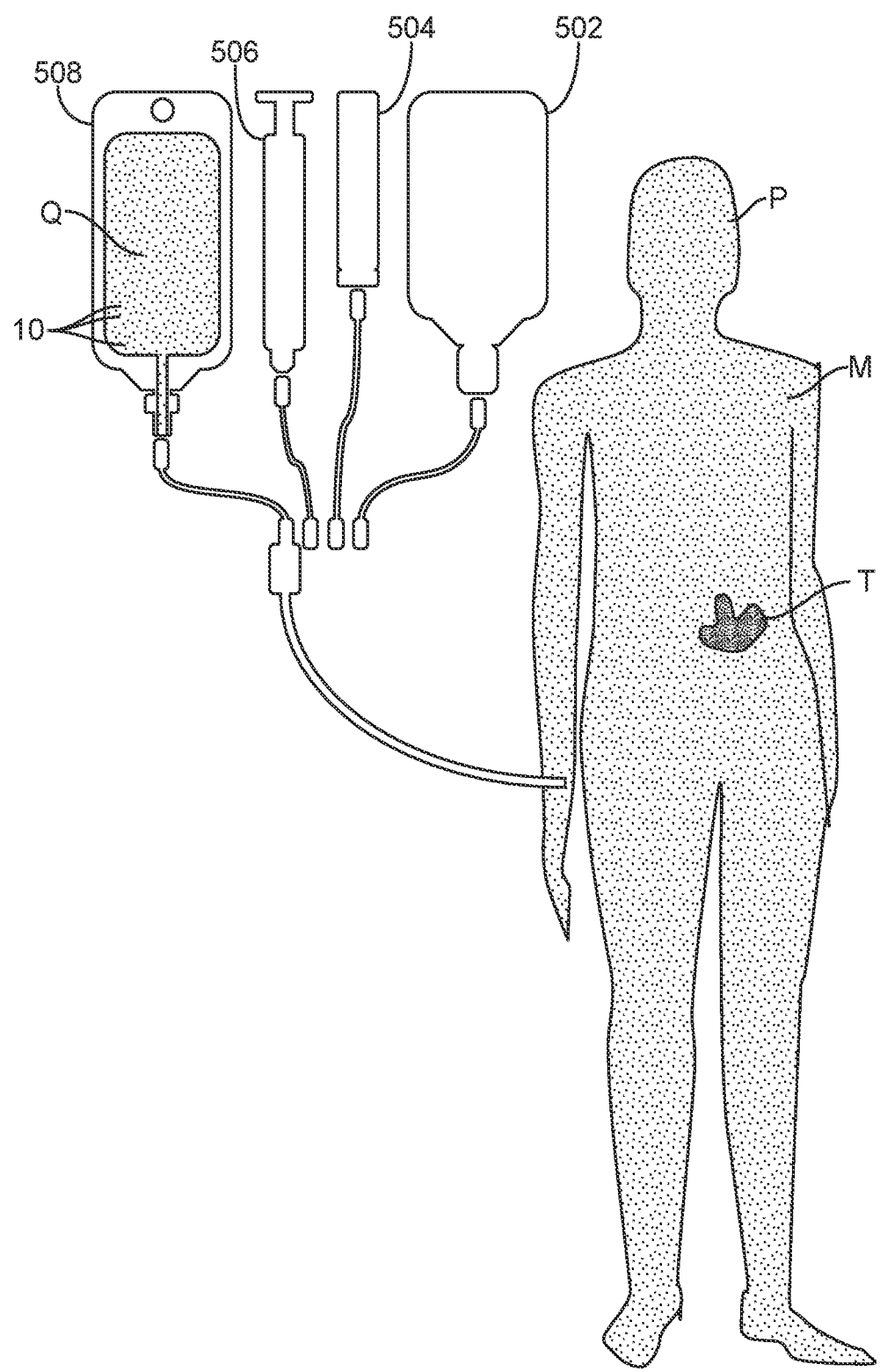
FIG. 38 visualizes three of these quantum dosing parameters: 1) target cells (T), 2) number of off-target cells (M), and 3) number of quants (Q).

FIG. 38 visualizes three of these quantum dosing parameters: 1) target cells (T), 2) number of off-target cells (M), and 3) number of quants (Q). In this example, target cells (T) are visualized as a tumor within a patient P. However, it may be appreciated that target cells (T) may be any type. Example target cells include a tumor cell in the treatment of cancer, or a neuron in the treatment of amyotrophic lateral sclerosis (ALS), a progressive neurodegenerative disease that affects nerve cells in the brain and the spinal cord. The number of target cells (T) is typically small in contrast to the number of non-targeted cells (M) which often comprise the bulk of an organism. In this example, the remainder of the patient's body is considered the non-targeted cells (M). In this example, the quants 10 are illustrated in an IV drip bag 508 ready for distribution into the patient P. Thus, the number of quants (Q) is shown as residing within the bag 508. Alternative delivery methods are shown, including a syringe 506, a vial 504 and a bottle 502. These vessels represent common drug distribution and administration modes. Successful quantum dosing involves a knowledge of (Q), (T), and (M).

Figures 39, 40:
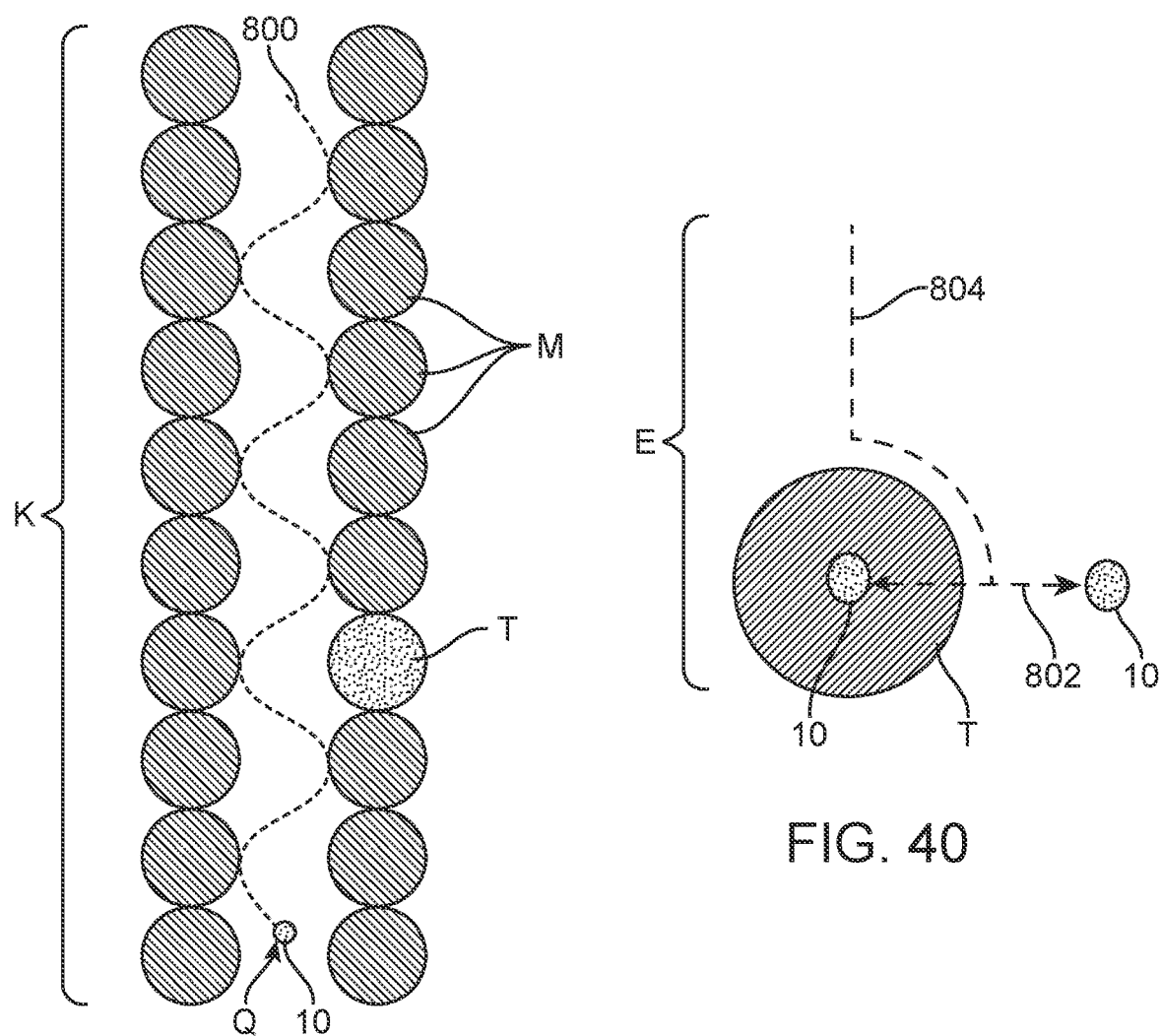
FIG. 39 visualizes the dosing parameter constant (K) which is the number of cells encountered per second.
FIG. 40 visualizes one aspect of the quantum dosing, effectivity (E).

FIG. 39 visualizes the dosing parameter constant (K) which is the number of cells encountered per second. The constant (K) is based on the relationship between the number of target cells (T), the number of non-target cells (M). FIG. 39 illustrates a quant 10 passing through the milieu of tissue as in the example of systemic delivery. The quant 10 comes into contact with the surface of multiple cells as it passes through capillaries and interstitial fluids represented here by non-targeted cells (M) and a single targeted cell (T). The path of the quant 10 is indicated by a dashed line 800 as it passes some cells while making physical contact with others. It may be appreciated that in this example a single quant 10 is shown for simplicity, however the organization of tissues and proportion of targeted cells (T) relative to non-targeted cells (M) would be different. The quant 10 encounters a number of non-targeted cells (M), each of which is an opportunity for an error in discrimination and an off-target absorption of the quant 10. The number of cells that a single quant 10 can be expected to encounter per second (K) is a factor of time in circulation and the rate of flow. The constant (K) is a fundamental characteristic of the quant 10 and represents the number of total cells (targeted and non-targeted) that a quant will encounter during its lifetime. In many embodiments, the quants 10 remain circulating in the patient P until they encounter a target cell (T).

FIG. 40 visualizes one aspect of the quantum dosing, effectivity (E). Effectivity (E) is the likelihood of a quant 10 entering a targeted cell (T) when encountering it. A dashed line 802 traces the path of a quant 10 as it makes contact with the surface of a single target cell (T). In this case the quant 10 enters the target cell (T). A dashed line 804 traces the path of a quant 10 as it misses the target cell (T). Thus, effectivity (E) is a term that accounts for the likelihood that a quant will perform as expected when a target cell is encountered. Cells that are accessed and successfully treated by quants are counted as cumulative target cells treated (C). The number of quants (Q) is the number of nano-drug particles needed to achieve a specific count of target cells remaining.

A quick look at the formula describing quantum dosing provides valuable insights, including key challenges. Perhaps most significantly, it makes plain that killing the last few tumor cells is difficult to achieve. Put simply, even a very well conceived quant particle is not likely to encounter a targeted cell within its lifetime. And as the therapy progresses, and the number of target cells is further reduced, the few remaining targeted cells become even less likely to be found. From a practical standpoint, that means more quants are necessary. Within that context, the more highly selective quants with long half-lives in circulation become more desirable; higher performance quants indicate a lower dose. Consider that there are about 10 trillion cells in the human body. We can estimate the number of cells that a single drug particle will encounter during its lifetime before it is resolved as an instance of dissolution or off-targeting. Interestingly, the same formula suggests that cancer, and other cellular disease conditions may be treated as chronic conditions, by maintaining target cell counts below a critical level.

All cells, including cancer cells, cannot exist in pure isolation. Despite their diseased condition, they must maintain the basics functions of metabolism and reproduction. Perhaps most significantly, all cells must absorb energy containing particles. In these ways and more, all cells interface with their environment and can thus be accessed and targeted by nanoscale particles. And whereas drug resistance is a common challenge to traditional soluble medicines, the broader approach of particle absorption is largely beyond the reach of evolutionary forces of adaptation that can confound the delivery of traditional chemotherapeutics.

Like other common and useful approximations, such as those used for traditional mass-based drug dosing and for radiation treatment, this formula is built upon several assumptions. However, the simplicity of the model justifies its utility, and the basic approach to determining a dose of particle-based drugs will remain a series function of the number of targets, and a factor that captures the likelihood that the particle will treat a target. Still, improvements can be made. Additional non-linear factors can be introduced to the general formula, such as biodistribution, and changes over time, such tumor cell replication. Also, a toxicity index could account for the relative impact of off-targeted quants. Many variations on the essential formula are possible, but the core elements remain intact.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A microfluidic partitioning system comprising:
 a base station superstructure comprising
  a first fluid inlet receiving a first fluid, the first fluid comprising a component molecule, an amphiphilic interface molecule having a hydrophilic portion and a hydrophobic portion, and a solvent system comprising a solvent;

a second fluid inlet receiving a second fluid, the second fluid comprising an aqueous solution;

an indexer configured to receive and arrange amounts of the first and second fluids along a longitudinal axis, the arranged amounts of first and second fluids having a core flow comprised of first fluid surrounded by a sheath flow comprised of second fluid;

an extruder connected with the indexer so as to receive flow of the first and second fluids therein, wherein the extruder includes at least one microfluidic channel configured to allow the core flow, while in laminar flow, to form droplets of the first fluid within the sheath flow and wherein the extruder enables each droplet to self-arrange into a fluid partition comprising a plurality of the amphiphilic interface molecules encapsulating an amount of the solvent system and one or more of the component molecules, the plurality of amphiphilic interface molecules arranged with their hydrophilic portions in contact with the aqueous solution of the sheath flow; and a mechanism configured to extract a quantity of the solvent system from each fluid partition so that each fluid partition forms a quant which is without the solvent.

2. A system as in claim 1, wherein the base station superstructure further comprises at least one mechanism for transporting the first and second fluids to the indexer so that pressure within the indexer is at least 100 psi.

3. A system as in claim 1, wherein each quant has a diameter of 20 to 300 nanometers.

4. A system as in claim 1, wherein each quant is of the same size so that any grouping of quants are uniform in size with a population coefficient of standard deviation of less than 20%.

5. A system as in claim 1, wherein the microfluidic channel has length of between 5 and 100 millimeters.

6. A system as in claim 1, wherein a linear flow rate of the coaxial flow in the microfluidic channel is approximately 1-20 meters per second.

7. A system as in claim 1, wherein the core flow is not more than 2 micrometers in diameter.

8. A system as in claim 1, wherein an outer diameter of the sheath flow is approximately 3-40 micrometers.

9. A system as in claim 1, wherein a ratio of the core flow to the sheath flow is approximately 1:1000.

10. A system as in claim 1, wherein the base station superstructure is configured so that the first and second fluids form a fluid interface within the indexer which is perpendicular to the longitudinal axis.

11. A system as in claim 10, wherein the first fluid inlet is disposed above the second fluid inlet and wherein the fluid interface is disposed between the first and second fluid inlets.

12. A system as in claim 1, wherein the extruder is removable from the indexer.

13. A system as in claim 12, further comprising another extruder which is attachable to the indexer in place of the extruder, wherein the extruder and the another extruder are comprised of different materials or have at least one differing microfluidic channel from each other.

14. A system as in claim 1, wherein the base station superstructure includes a computer control unit which controls at least the at least one mechanism for transporting the first and second fluids to the indexer.

15. A system as in claim 14, wherein the at least one microfluidic channel comprises a single microfluidic channel having a first end and a second end, the system further comprising a first electrode disposed near the first end of the microfluidic channel and a second electrode disposed near the second end of the microfluidic channel, wherein the computer control unit monitors an electronic signal generated by an electric current passing between the first and second electrodes.

16. A system as in claim 15, wherein the computer control unit is able to reprogram at least the at least one mechanism for transporting the first and second fluids to the indexer based on the electronic signal.

17. A system as in claim 1, wherein the base station superstructure further comprises a third fluid inlet for receiving a third fluid so as to combine the third fluid within the first fluid, wherein the third fluid is miscible with the first fluid so that the core flow is comprised of the first and third fluids.

18. A system as in claim 1, wherein the indexer further comprises a pulsed energy source configured to introduce controlled perturbations to the coaxial flow.

19. A system as in claim 1, wherein the first and second fluids within the indexer define a fluid interface that (i) is perpendicular to a longitudinal axis of a chamber of the indexer, (ii) is perpendicular to a longitudinal axis of the extruder, and (iii) is configured to enable coextrusion of the first and second fluids into the extruder.

20. A system as in claim 1, wherein the component molecule comprises comprise a drug, a lipid, a protein, an antibody, an isotope, a radioactive isotope, a nucleic acid sequence, or any combination thereof.

* * * * *